US012435107B2

(12) United States Patent
Mudd et al.

(10) Patent No.: US 12,435,107 B2
(45) Date of Patent: Oct. 7, 2025

(54) HETEROTANDEM BICYCLIC PEPTIDE COMPLEX

(71) Applicant: BicycleTx Limited, Cambridge (GB)

(72) Inventors: Gemma Mudd, Lexington, MA (US); Punit Upadhyaya, Lexington, MA (US); Kevin McDonnell, Cambridge (GB); Johanna Lahdenranta, Lexington, MA (US)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 18/424,386

(22) Filed: Jan. 26, 2024

(65) Prior Publication Data

US 2024/0336656 A1 Oct. 10, 2024

Related U.S. Application Data

(63) Continuation of application No. 17/592,966, filed on Feb. 4, 2022, now Pat. No. 11,970,553, which is a continuation of application No. 16/941,614, filed on Jul. 29, 2020, now Pat. No. 11,306,123.

(60) Provisional application No. 63/024,715, filed on May 14, 2020, provisional application No. 63/022,667, filed on May 11, 2020, provisional application No. 62/931,442, filed on Nov. 6, 2019, provisional application No. 62/910,088, filed on Oct. 3, 2019, provisional application No. 62/880,191, filed on Jul. 30, 2019.

(51) Int. Cl.

| | |
|---|---|
| ***C07K 7/08*** | (2006.01) |
| ***A61K 9/00*** | (2006.01) |
| ***A61K 38/12*** | (2006.01) |
| ***A61K 47/64*** | (2017.01) |
| ***A61P 35/00*** | (2006.01) |
| ***C07K 11/02*** | (2006.01) |
| ***C07K 14/00*** | (2006.01) |
| ***C07K 14/705*** | (2006.01) |
| *A61K 38/00* | (2006.01) |

(52) U.S. Cl.

CPC .............. *C07K 7/08* (2013.01); *A61K 9/0019* (2013.01); *A61K 38/12* (2013.01); *A61K 47/641* (2017.08); *A61P 35/00* (2018.01); *C07K 11/02* (2013.01); *C07K 14/001* (2013.01); *C07K 14/70578* (2013.01); *A61K 38/00* (2013.01)

(58) Field of Classification Search

CPC ......... C07K 7/08; A61P 35/00; A61K 9/0019; A61K 38/12

See application file for complete search history.

(56) References Cited

U.S. PATENT DOCUMENTS

| | | | |
|---|---|---|---|
| 2,642,514 | A | 6/1953 | Herkenhoff |
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,595,756 | A | 1/1997 | Bally et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,326,144 | B1 | 12/2001 | Bawendi et al. |
| 6,468,808 | B1 | 10/2002 | Nie et al. |
| 7,151,047 | B2 | 12/2006 | Chan et al. |
| 7,192,785 | B2 | 3/2007 | Nie et al. |
| 8,138,347 | B2 | 3/2012 | Knight et al. |
| 8,680,022 | B2 | 3/2014 | Gregory et al. |
| 8,685,890 | B2 | 4/2014 | Winter et al. |
| 8,778,844 | B2 | 7/2014 | Winter et al. |
| 8,986,655 | B2 | 3/2015 | Weiss et al. |
| 9,518,081 | B2 | 12/2016 | Winter et al. |
| 9,644,201 | B2 | 5/2017 | Winter et al. |
| 9,657,288 | B2 | 5/2017 | Winter et al. |
| 9,670,482 | B2 | 6/2017 | Winter et al. |
| 9,670,484 | B2 | 6/2017 | Winter et al. |
| 9,670,521 | B2 | 6/2017 | Grabstein et al. |
| 9,868,767 | B2 | 1/2018 | Pei et al. |
| 9,932,367 | B2 | 4/2018 | Stace et al. |
| 9,994,617 | B2 | 6/2018 | Tite et al. |
| 10,118,947 | B2 | 11/2018 | Teufel et al. |
| 10,294,274 | B2 | 5/2019 | Teufel et al. |
| 10,441,663 | B2 | 10/2019 | Bennett et al. |
| 10,532,106 | B2 | 1/2020 | Teufel et al. |
| 10,624,968 | B2 | 4/2020 | Bennett et al. |
| 10,626,147 | B2 | 4/2020 | Pei et al. |

(Continued)

FOREIGN PATENT DOCUMENTS

| | | | |
|---|---|---|---|
| CN | 101497878 | A | 5/2009 |
| EP | 3192802 | A1 | 7/2017 |

(Continued)

OTHER PUBLICATIONS

"Bicycle Therapeutics Investor Presentation", Retrieved from: https://investors.bicycletherapeutics.com/static-files/f456c054-95c8-4e19-a62a-fcf5feb0650b, Aug. 2024, 61 pages.

(Continued)

*Primary Examiner* — Amber D Steele
(74) *Attorney, Agent, or Firm* — Wolf, Greenfield & Sacks, P.C.

(57) ABSTRACT

The present invention relates to a heterotandem bicyclic peptide complex which comprises a first peptide ligand, which binds to Nectin-4, conjugated via a linker to two second peptide ligands, which bind to CD137. The invention also relates to the use of said heterotandem bicyclic peptide complex in preventing, suppressing or treating cancer.

21 Claims, 13 Drawing Sheets

Specification includes a Sequence Listing.

(56) References Cited

U.S. PATENT DOCUMENTS 10,792,368 B1 10/2020 Teufel et al.
10,800,813 B2 10/2020 Tite et al.
10,857,196 B2 12/2020 Beswick et al.
10,870,679 B2 12/2020 Teufel et al.
10,875,894 B2 12/2020 Chen et al.
10,894,808 B2 1/2021 Teufel et al.
10,899,798 B2 1/2021 Bennett et al.
10,919,937 B2 2/2021 Beswick et al.
10,994,019 B2 5/2021 Teufel et al.
11,103,591 B2 8/2021 Teufel et al.
11,180,531 B2 11/2021 Beswick et al.
11,241,473 B2 2/2022 Beswick et al.
11,261,214 B2 3/2022 Chen et al.
11,306,123 B2 4/2022 Mudd et al.
11,312,749 B2 4/2022 Mudd et al.
11,332,500 B2 5/2022 Mudd et al.
11,396,530 B2 7/2022 Beswick et al.
11,414,488 B2 8/2022 Bennett et al.
11,433,137 B2 9/2022 Bennett et al.
11,453,702 B2 9/2022 Beswick et al.
11,453,703 B2 9/2022 Keen et al.
11,484,602 B2 11/2022 Chen et al.
11,542,304 B2 1/2023 Chen et al.
11,613,560 B2 3/2023 Stephen et al.
11,623,012 B2 4/2023 Chen et al.
11,672,868 B2 6/2023 Teufel et al.
11,696,956 B2 7/2023 Chen et al.
11,730,819 B2 8/2023 Teufel et al.
11,746,126 B2 9/2023 Bennett et al.
11,814,447 B2 11/2023 Teufel et al.
11,833,211 B2 12/2023 Chen et al.
11,912,792 B2 2/2024 Beswick et al.
11,946,041 B2 4/2024 Chen et al.
11,970,553 B2 4/2024 Mudd et al.
12,049,520 B2 7/2024 Chen et al.
2002/0164788 A1 11/2002 Ellis et al.
2005/0169931 A1 8/2005 Kinch et al.
2009/0222937 A1 9/2009 Arnould et al.
2009/0304721 A1 12/2009 Kinch et al.
2012/0101253 A1 4/2012 Heinis et al.
2012/0172235 A1 7/2012 Winter et al.
2013/0064791 A1 3/2013 Poelstra et al.
2013/0072598 A1 3/2013 Yang et al.
2014/0163201 A1 6/2014 Winter et al.
2014/0249292 A1 9/2014 Tite et al.
2014/0256596 A1 9/2014 Tite et al.
2014/0274759 A1 9/2014 Walker et al.
2015/0038434 A1 2/2015 Yang et al.
2015/0087810 A1 3/2015 Moore et al.
2016/0031939 A1 2/2016 Stace et al.
2016/0046721 A1 2/2016 Qian et al.
2016/0122430 A1 5/2016 Gish et al.
2016/0256579 A1 9/2016 Shalom
2016/0326232 A1 11/2016 Rosa et al.
2017/0067045 A1 3/2017 Winter et al.
2017/0190743 A1 7/2017 Pei et al.
2017/0204150 A1 7/2017 Liu et al.
2017/0304342 A1 10/2017 Cox et al.
2017/0306032 A1 10/2017 Gehlsen
2017/0360952 A1 12/2017 Schwartz et al.
2018/0311300 A1 11/2018 Beswick et al.
2018/0318451 A1 11/2018 Skerra et al.
2018/0362585 A1 12/2018 Teufel et al.
2018/0371020 A1 12/2018 Bennett et al.
2019/0134213 A1 5/2019 Teufel et al.
2019/0184025 A1 6/2019 Chen et al.
2019/0263866 A1 8/2019 Chen et al.
2019/0307836 A1 10/2019 Keen et al.
2019/0389906 A1 12/2019 Beswick et al.
2019/0389907 A1 12/2019 Teufel et al.
2020/0129630 A1 4/2020 Koehler et al.
2020/0190213 A1 6/2020 Preyer et al.
2020/0255477 A1 8/2020 Chen et al.
2020/0283482 A1 9/2020 Keen et al.
2020/0291096 A1 9/2020 Keen et al.
2020/0338203 A1 10/2020 Chen et al.
2020/0354406 A1 11/2020 Stephen et al.
2021/0040154 A1 2/2021 Mudd et al.
2021/0069287 A1 3/2021 Mudd et al.
2021/0079045 A1 3/2021 Bennett et al.
2021/0101932 A1 4/2021 Chen et al.
2021/0101933 A1 4/2021 Chen et al.
2021/0101937 A1 4/2021 Mudd et al.
2021/0122785 A1 4/2021 Teufel et al.
2021/0122804 A1 4/2021 Teufel et al.
2021/0147484 A1 5/2021 Beswick et al.
2021/0147485 A1 5/2021 Teufel et al.
2021/0261620 A1 8/2021 Teufel et al.
2021/0269480 A1 9/2021 Beswick et al.
2021/0299210 A2 9/2021 Keen et al.
2022/0024982 A1 1/2022 Chen et al.
2022/0031858 A1 2/2022 Mcdonnell et al.
2022/0054646 A1 2/2022 Chen et al.
2022/0064218 A1 3/2022 Baldassarre et al.
2022/0064221 A1 3/2022 Lani et al.
2022/0072140 A1 3/2022 Stace et al.
2022/0088118 A1 3/2022 Baldassarre et al.
2022/0088207 A1 3/2022 Chen et al.
2022/0119488 A1 4/2022 Lani et al.
2022/0133732 A1 5/2022 Baldassarre et al.
2022/0133733 A1 5/2022 Baldassarre et al.
2022/0135614 A1 5/2022 Teufel et al.
2022/0184222 A1 6/2022 Bennett et al.
2022/0194983 A1 6/2022 Teufel et al.
2022/0227811 A1 7/2022 Mudd et al.
2022/0242911 A1 8/2022 Mudd et al.
2022/0257784 A1 8/2022 Upadhyaya et al.
2022/0275053 A1 9/2022 Upadhyaya et al.
2022/0281918 A1 9/2022 Van Rietschoten et al.
2022/0306689 A9 9/2022 Chen et al.
2022/0306694 A1 9/2022 Mudd et al.
2022/0362390 A1 11/2022 Stace et al.
2022/0387611 A1 12/2022 Bennett et al.
2023/0002596 A1 1/2023 Zhang et al.
2023/0008076 A1 1/2023 Keen et al.
2023/0025916 A1 1/2023 Bennett et al.
2023/0025971 A1 1/2023 Bennett et al.
2023/0086865 A1 3/2023 Balmford et al.
2023/0106511 A1 4/2023 Balmforth et al.
2023/0129258 A1 4/2023 Upadhyaya et al.
2023/0144799 A1 5/2023 Chen et al.
2023/0165966 A1 6/2023 Koehler et al.
2023/0181749 A1 6/2023 Dickson et al.
2023/0220008 A1 7/2023 Chen et al.
2023/0233698 A1 7/2023 Bennett et al.
2023/0340020 A1 10/2023 Teufel et al.
2024/0000957 A1 1/2024 Chen et al.
2024/0082410 A1 3/2024 Teufel et al.
2024/0108738 A1 4/2024 Keen et al.
2024/0158444 A1 5/2024 Bennett et al.
2024/0173422 A1 5/2024 Beswick et al.
2024/0189436 A1 6/2024 Chen et al.
2024/0197897 A1 6/2024 Keen et al.
2024/0240255 A1 7/2024 Blakemore et al.
2024/0325554 A1 10/2024 Keen et al.

FOREIGN PATENT DOCUMENTS

FR 2932189 A1 11/2009
GB 1239978 A 7/1971
JP 2006514104 A 4/2006
JP 2011513298 A 4/2011
JP 2011522794 A 4/2011
WO WO1997008320 A1 6/1997
WO WO1998019705 A1 5/1998
WO WO-2001042246 A2 6/2001
WO WO-2002088112 A1 11/2002
WO WO-2003063794 A2 8/2003
WO WO-2004005348 A1 1/2004
WO WO-2004019973 A1 3/2004
WO WO-2004077062 A2 9/2004
WO WO-2004089925 A1 10/2004
WO WO-2005007623 A2 1/2005
WO WO-2005103083 A2 11/2005

(56) References Cited

FOREIGN PATENT DOCUMENTS

| | | | |
|---|---|---|---|
| WO | WO-2005113554 | A2 | 12/2005 |
| WO | WO-2006078161 | A1 | 7/2006 |
| WO | WO-2006078846 | A1 | 7/2006 |
| WO | WO2006101187 | A1 | 9/2006 |
| WO | WO-2006122806 | A2 | 11/2006 |
| WO | WO-2007016176 | A2 | 2/2007 |
| WO | WO-2007044729 | A2 | 4/2007 |
| WO | WO-2007053452 | A1 | 5/2007 |
| WO | WO-2007070514 | A1 | 6/2007 |
| WO | WO-2007084786 | A1 | 7/2007 |
| WO | WO-2007129161 | A2 | 11/2007 |
| WO | WO-2008033561 | A2 | 3/2008 |
| WO | WO-2008039218 | A2 | 4/2008 |
| WO | WO2008134761 | A2 | 6/2008 |
| WO | WO2008089627 | A1 | 7/2008 |
| WO | WO-2008109943 | A1 | 9/2008 |
| WO | WO-2008157490 | A1 | 12/2008 |
| WO | WO-2009098450 | A2 | 8/2009 |
| WO | WO-2009114512 | A1 | 9/2009 |
| WO | WO-2010089115 | A1 | 8/2010 |
| WO | WO2010089117 | A1 | 12/2010 |
| WO | WO-2011018227 | A2 | 2/2011 |
| WO | WO2011079015 | A1 | 6/2011 |
| WO | WO-2011090760 | A1 | 7/2011 |
| WO | WO-2012057624 | A1 | 5/2012 |
| WO | WO2013050615 | A1 | 4/2013 |
| WO | WO-2013050617 | A1 | 4/2013 |
| WO | WO2013050616 | A1 | 11/2013 |
| WO | WO2014044872 | A1 | 3/2014 |
| WO | WO2014063012 | A1 | 4/2014 |
| WO | WO-2014164693 | A2 | 10/2014 |
| WO | WO2014167122 | A1 | 10/2014 |
| WO | WO2014190257 | A2 | 11/2014 |
| WO | WO2015116904 | A1 | 6/2015 |
| WO | WO-2015171938 | A1 | 11/2015 |
| WO | WO2015179691 | A2 | 11/2015 |
| WO | WO2016046574 | A1 | 3/2016 |
| WO | WO2016050361 | A1 | 4/2016 |
| WO | WO-2016067035 | A1 | 5/2016 |
| WO | WO-2016171242 | A1 | 10/2016 |
| WO | WO2016171272 | A1 | 10/2016 |
| WO | WO-2016174103 | A1 | 11/2016 |
| WO | WO2017046658 | A1 | 3/2017 |
| WO | WO2017102906 | A1 | 6/2017 |
| WO | WO-2017161069 | A1 | 9/2017 |
| WO | WO-2017173408 | A1 | 10/2017 |
| WO | WO-2017182672 | A1 | 10/2017 |
| WO | WO-2017191460 | A1 | 11/2017 |
| WO | WO2017205738 | A1 | 11/2017 |
| WO | WO2018096365 | A1 | 5/2018 |
| WO | WO-2018115203 | A1 | 6/2018 |
| WO | WO-2018115204 | A1 | 6/2018 |
| WO | WO2018222987 | A1 | 6/2018 |
| WO | WO-2018127699 | A1 | 7/2018 |
| WO | WO-2018156740 | A1 | 8/2018 |
| WO | WO-2018197509 | A1 | 11/2018 |
| WO | WO2018197893 | A1 | 11/2018 |
| WO | WO-2019002842 | A1 | 1/2019 |
| WO | WO-2019025811 | A1 | 2/2019 |
| WO | WO-2019034866 | A1 | 2/2019 |
| WO | WO-2019034868 | A1 | 2/2019 |
| WO | WO2019084060 | A1 | 5/2019 |
| WO | WO2019094395 | A2 | 5/2019 |
| WO | WO-2019122860 | A1 | 6/2019 |
| WO | WO-2019122861 | A1 | 6/2019 |
| WO | WO-2019122863 | A1 | 6/2019 |
| WO | WO-2019136442 | A1 | 7/2019 |
| WO | WO-2019162682 | A1 | 8/2019 |
| WO | WO-2019193328 | A1 | 10/2019 |
| WO | WO-2019226617 | A1 | 11/2019 |
| WO | WO-2019243313 | A1 | 12/2019 |
| WO | WO2019243329 | A1 | 12/2019 |
| WO | WO2019243353 | A1 | 12/2019 |
| WO | WO2019243455 | A1 | 12/2019 |
| WO | WO-2019243832 | A1 | 12/2019 |
| WO | WO-2019243833 | A1 | 12/2019 |
| WO | WO-2020084305 | A1 | 4/2020 |
| WO | WO2020089627 | A1 | 5/2020 |
| WO | WO2020120980 | A1 | 6/2020 |
| WO | WO2020120981 | A1 | 6/2020 |
| WO | WO2020120983 | A1 | 6/2020 |
| WO | WO-2020120984 | A1 | 6/2020 |
| WO | WO-2020128526 | A1 | 6/2020 |
| WO | WO2020128527 | A1 | 6/2020 |
| WO | WO2020148525 | A1 | 7/2020 |
| WO | WO2020148526 | A1 | 7/2020 |
| WO | WO2020148527 | A1 | 7/2020 |
| WO | WO2020148528 | A1 | 7/2020 |
| WO | WO2020148529 | A1 | 7/2020 |
| WO | WO2020148530 | A1 | 7/2020 |
| WO | WO2020165600 | A1 | 8/2020 |
| WO | WO2020178574 | A1 | 9/2020 |
| WO | WO-2020201753 | A1 | 10/2020 |
| WO | WO-2020225577 | A1 | 11/2020 |
| WO | WO2020229803 | A1 | 11/2020 |
| WO | WO-2021019243 | A1 | 2/2021 |
| WO | WO-2021019244 | A1 | 2/2021 |
| WO | WO-2021019245 | A1 | 2/2021 |
| WO | WO-2021019246 | A1 | 2/2021 |
| WO | WO-2021028686 | A1 | 2/2021 |
| WO | WO2021171028 | A1 | 2/2021 |
| WO | WO2021171029 | A1 | 2/2021 |
| WO | WO2021038232 | A1 | 3/2021 |
| WO | WO-2021064428 | A1 | 4/2021 |
| WO | WO2021074622 | A1 | 4/2021 |
| WO | WO2021074647 | A1 | 4/2021 |
| WO | WO-2021105694 | A1 | 6/2021 |
| WO | WO2021148974 | A1 | 7/2021 |
| WO | WO2021234391 | A1 | 11/2021 |
| WO | WO-2021250418 | A1 | 12/2021 |
| WO | WO-2022038158 | A1 | 2/2022 |
| WO | WO2022148969 | A1 | 7/2022 |
| WO | WO2022148974 | A2 | 7/2022 |
| WO | WO-2022148975 | A1 | 7/2022 |
| WO | WO-2022148979 | A1 | 7/2022 |
| WO | WO2022029420 | A1 | 10/2022 |
| WO | WO2023089308 | A1 | 5/2023 |
| WO | WO2023031623 | A2 | 9/2023 |

OTHER PUBLICATIONS

"Figure 3.8: Antigens can bind in pockets or groves, or an extended surfaces in the binding sites of antibodies", Immunobiology: The Immune System in Health and Disease, Garland Science, 2001, 1 page.

Adley et al., "Expression of membrane type 1 matrix metalloproteinase (MMP-14) in epithelial ovarian cancer: High level expression in clear cell carcinoma", Gynecologic Oncology, 2009, 112(2):319-324.

Akanuma et al., "MicroRNA-133a regulates the mRNAs of two invadopodia-related proteins, FSCN1 and MMP14, in esophageal cancer", British Journal of Cancer, 2014, 110(1):189-198.

Angelini et al., "Bicyclic Peptide Inhibitor Reveals Large Contact Interface with a Protease Target", ACS Chemical Biology, 2012, 7(5):817-821.

Anonymous, "Bicycle Therapeutics 2023 R&D Day Deck", Retrieved from: https://investors.bicycletherapeutics.com/static-files/46599fde-67dc-40a8-9dcb-10ed8444f31e, Dec. 14, 2023, 155 pages.

Anonymous, "Bicycle Therapeutics BT8009 Regulatory Update", Retrieved from: https://investors.bicycletherapeutics.com/static-files/265210c3-233f-4dd8-af32-d34592398d85, Sep. 11, 2023, 23 pages.

Anonymous, "UPI000011DEEB", Retrieved from: https://www.uniprot.org/uniparc/UPI000011DEEB, 2014, 2 pages.

Anthony et al., "Recapitulation of IVIG Anti-Inflammatory Activity with a Recombinant IgG Fc", Science, Apr. 18, 2008, 320(5874):373-376.

Arkadash et al., "Development of High Affinity and High Specificity Inhibitors of Matrix Metalloproteinase 14 through Computational Design and Directed Evolution", Journal of Biological Chemistry, Feb. 24, 2017, 292(8):3481-3495.

(56) References Cited

OTHER PUBLICATIONS

Arnon et al., "The mechanisms controlling the recognition of tumor- and virus-infected cells by NKp46", Blood, Jan. 15, 2004, 103(2):664-672.
Arnould et al., "Trastuzumab-based treatment of HER2-positive breast cancer: an antibody-dependent cellular cytotoxicity mechanism?", British Journal of Cancer, 2006, 94(2):259-267.
Askoxylakis et al., "A New Peptide Ligand for Targeting Human Carbonic Anhydrase IX, Identified through the Phage Display Technology", PLoS ONE, Dec. 2010, 5(12), pp. 1-10.
Augoff et al., "Upregulated expression and activation of membrane-associated proteases in esophageal squamous cell carcinoma", Oncology Reports, 2014, 31(6):2820-2826.
Bader et al., "Abstract 3088: Breaking from the paradigm of antibody-drug conjugates: Evaluation of clinical pharmacokinetics and safety of Bicycle Toxin Conjugates® (BTCs)", American Society of Clinical Oncology Annual Meeting, May 31-Jun. 4, 2024, pp. 1-9.
Baek et al., "Effects of Histidine and Sucrose on the Biophysical Properties of a Monoclonal Antibody", Pharmaceutical Antibody, Dec. 29, 2016, 34(3):629-639.
Baldini et al., "Abstract 498: BT8009-100: A Phase I/II Study of Novel Bicyclic Peptide and MMAE Conjugate BT8009 in Patients (pts) with Advanced Malignancies Associated with Nectin-4 Expression, Including Urothelial Cancer (UC)", ASCO Genitourinary (GU) Cancers Symposium Conference, Feb. 17, 2023, pp. 1-6.
Banerji et al., "A Cancer Research UK Phase I/IIA Trail of BT1718 (a first in class Bicycle Drug Conjugate) Given Intravenously in Patients with Advanced Solid Tumours", Journal of Clinical Oncology, Jun. 1, 2018, 36(15):PS2610, 2 pages.
Banerji et al., "A Cancer Research UK phase I/IIa trial of BT1718 (a first in class Bicycle Toxin Conjugate) given intravenously in patients with advanced solid tumours", ASCO, Jun. 5, 2018, pp. 1-4.
Banerji et al., "A Cancer Research UK phase I/IIa trial of BT1718 (a first in class Bicycle Toxin Conjugate) given intravenously in patients with advanced solid tumours", NCRI, Oct. 1, 2018, 1 page.
Banerji et al., "Abstract 178: Preliminary pharmacokinetic assessment of BT1718: A phase I/IIa trial of BT1718 (a first in class Bicycle Toxin Conjugate) in patients with advanced solid tumours", European Journal of Cancer, 2018, pp. 1-4.
Barbas III et al., "Semisynthetic combinatorial antibody libraries: A chemical solution to the diversity problem", Proc. Natl. Acad. Sci., May 1992, 89(10):4457-4461.
Barbolina et al., "Microenvironmental Regulation of Membrane Type 1 Matrix Metalloproteinase Activity in Ovarian Carcinoma Cells via Collagen-induced EGR1 Expression", Journal of Biological Chemistry, Feb. 16, 2007, 282(7):4924-4931.
Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer", Journal of Clinical Oncology, Jul. 1, 2017, 35(19):2141-2148.
Battula et al., "Abstract 4613: A novel fully synthetic dual targeted EphA2/CD137 Bicycle® peptide induces tumor localized CD137 agonism", American Association of Cancer Research, Jun. 22, 2020, pp. 1-4.
Battula et al., "Abstract P794: A novel fully synthetic dual targeted EphA2/4-1BB Bicycle® peptide induces tumor localized 4-1BB agonism", SITC, Nov. 9, 2019, pp. 1-4.
Bech et al., "Chemical Strategies for Half-Life Extension of Biopharmaceuticals: Lipidation and Its Alternatives", ACS Medicinal Chemistry Letters, Jun. 15, 2018, 9(7):577-580.
Bendell et al., "TPS3655: BT5528-100 Phase I/II Study; Safety, Pharmacokinetics & Preliminary Clinical Activity of BT5528 in Patients with Advanced Malignancies Associated with EphA2 Expression", ASCO, May 29, 2020, 1 page.
Bennett et al., "Abstract 1167/2: Development of BT1718, a novel Bicycle Drug Conjugate for the treatment of lung cancer", American Association of Cancer Research, Apr. 1, 2017, pp. 1-4.
Bennett et al., "Abstract 164: BT5528, an EphA2-targeting Bicycle Toxin Conjugate (BTC): profound efficacy without bleeding and coagulation abnormalities in animal models", EORTC, Nov. 13, 2018, pp. 1-6.
Bennett et al., "Abstract 5854: BT5528, a Bicycle Toxin Conjugate (BTC) targeting EphA2 has potent antitumour activity without bleeding or coagulation abnormalities in animal models", American Association of Cancer Research, Apr. 14, 2018, pp. 1-6.
Bennett et al., "Abstract 5855: Bicycle Toxin Conjugates (BTCs) targeting EphA2 for the treatment of solid tumours: Discovery and selection of BT5528", American Association of Cancer Research, Apr. 14, 2018, pp. 1-8.
Bennett et al., "Abstract B135: The Mechanism of Action of BT1718, a Novel Small-Molecule Drug Conjugate for the Treatment of Solid Tumors Expressing MT1-MMP", AACR-NCI-EOrTC International Conference: Molecular Targets and Cancer Therapeutics, Jan. 2018, 17(1 Suppl), 4 pages.
Bennett et al., "Abstract C066: BT5528, a Bicycle Toxin Conjugate targeting EphA2: mechanism of action and clinical translation", AACR-NCI-EORTC, Oct. 29, 2019, pp. 1-6.
Bennett, "Abstract 4481: BT5528, an EphA2-targeting Bicycle® Toxin Conjugate (BTC): Profound efficacy without bleeding and coagulation abnormalities in animal models", AACR Annual Meeting, Apr. 4, 2019, 11 pages.
Bennett, "Bicycle Conjugates to Target Solid Tumors", Next Generation Conjugates Summit, Feb. 27, 2023, 23 pages.
Bennett, "BT5528: A Bicycle Toxin Conjugate Targeting EphA2 for the Treatment of Solid Tumours", 9th Annual World ADC Conference, Mar. 6, 2019, 13 pages.
Ben-Shmuel et al., "Unleashing Natural Killer Cells in the Tumor Microenvironment—The Next Generation of Immunotherapy?", Frontiers in Immunology, Feb. 21, 2020, 11(Article 275), pp. 1-23.
Berenson, "Multiple Myeloma (Myelomatosis; Plasma Cell Myeloma)", Merck Manual Consumer Version, 2020, 6 pages.
Berenson, "Multiple Myeloma", Merck Manual, Retrieved from: https://www.merckmanuals.com/home/blood-disorders/plasma-cell-disorders/multiplemyeloma?query=multiple%20myeloma, Sep. 2022, 5 pages.
Berkel et al., "Binding of (5S)-Penicilloic Acid to Penicillin Binding Protein 3", ACS Chemical Biology, 2013, 8(10):2112-2116.
Bernhagen, "Design, synthesis and characterization of different bicyclic peptides with enhanced binding and selectivity for various integrins", BIOGEL, Apr. 1, 2015, pp. 1-6.
Bicycle Therapeutics, "Bicycle Therapeutics and Cancer Research UK announce initiation of first clinical study of a bicyclic peptide (Bicycle®)", Press Release, Retrieved from: https://investors.bicycletherapeutics.com/node/6651/pdf, Feb. 13, 2018, 2 pages.
Bilsky, "Gliomas", Merck Manual, Retrieved from: https://www.merckmanuals.com/professional/neurologic-disorders/intracranial-and-spinal-tumors/gliomas, May 2023, 8 pages.
Biron et al., "Improving Oral Bioavailability of Peptides by Multiple N-Methylation: Somatostatin Analogues", Angew. Chem. Int. Ed., 2008, 47(14):2595-2599.
Blank et al., "Absence of Programmed Death Receptor 1 Alters Thymic Development and Enhances Generation of CD4/CD8 Double-Negative TCR-Transgenic T Cells", The Journal of Immunology, 2003, 171(19):4574-4581.
Bogaerts et al., "Individual patient data analysis to assess modifications to the RECIST criteria", European Journal of Cancer, 2009, 45(2):248-260.
Bolland et al., "Spontaneous Autoimmune Disease in Fc(gamma)RIIB-Deficient Mice Results from Strain-Specific Epistasis", Immunity, Aug. 2000, 13(2):277-285.
Borghaei et al., "Nivolumab versus Docetaxel in Advanced Non-squamous Non-small Cell Lung Cancer", N Engl J Med., Oct. 22, 2015, 373(17):1627-1639.
Borrelli et al., "Cell Penetrating Peptides as Molecular Carriers for Anti-Cancer Agents", Molecules, Jan. 31, 2018, 23(2):295, pp. 1-28.
Boruchov et al., "Activating and inhibitory IgG Fc receptors on human DCs mediate opposing functions", The Journal of Clinical Investigation, Oct. 2005, 115(10):2914-2923.

(56) References Cited

OTHER PUBLICATIONS

Bouchard et al., "Antibody-drug conjugates-a new wave of cancer drugs", Bioorganic & medicinal chemistry letters, 2014, 24(23):5357-5363.
Bournakas et al., "PBP inhibitors discovered using a modified phage display platform (Bicycles)", ESCMID, Oct. 11, 2022, 1 page.
Brahmer et al., "Nivolumab versus Docetaxel in Advanced Squamous-Cell Non-Small-Cell Lung Cancer", New England Journal of Medicine, Jul. 9, 2015, 373(2):123-135.
Brandish, "Bicycle Therapeutics: Precision-guided immune agonism for the treatment of cancer", Immuno UK meeting, Sep. 30, 2022, 25 pages.
Bristol-Myers Squibb, "An Investigational Immuno-Therapy Study to Investigate the Safety and Effectiveness of Nivolumab, and Nivolumab Combination Therapy in Virus-Associated Tumors", ClinicalTrials.gov Identifier: NCT02488759, 2022, 9 pages.
Brown et al., "Blockade of Programmed Death-1 Ligands on Dendritic Cells Enhances T Cell Activation and Cytokine Production", The Journal of Immunology, 2003, 170(3):1257-1266.
Cabanillas et al., "Phase I study of maytansine using a 3-day schedule", Cancer Treat Rep., Mar. 1978, 62(3):425-428 (English Abstract Only).
Campbell et al., "Poster 1197: A multi tumor survey of Nectin-4 expression to guide BT8009 indication selection", American Association of Cancer Research, Apr. 12, 2021, pp. 1-4.
Campbell et al., "Poster 5300: A survey of EphA2 expression by immunohistochemistry (IHC) in tumor tissue microarrays (TMAs) to support BT5528 indication selection", American Association of Cancer Research, Jun. 22, 2020, pp. 1-6.
Cancer Research UK, "Soft Tissue Sarcomas", Retrieved from: http://aboutcancer.cancerresearchuk.org/about-cancer/soft-tissue-sarcoma, Apr. 21, 2021, 4 pages.
Cancer Research UK, "Triple Negative Breast Cancer", Retrieved from: https://www.cancerresearchuk.org/about-cancer/breast-cancer/stages-types-grades/types/triplenegative-breast-cancer#, Jun. 22, 2023, 7 pages.
Cancer Research UK, "Types of Lung Cancer", Retrieved form: https://www.cancerresearchuk.org/about-cancer/lung-cancer/stages-types-grades/types#, Dec. 30, 2022, 5 pages.
Cancer Research UK, "Your Mouth and Cancer Drugs", Retrieved from: https://www.cancerresearchuk.org/about-cancer/cancer-in-general/treatment/cancer-drugs/sideeffects/your-mouth, Jan. 22, 2020, 6 pages.
Carabateas et al., "Strong Analgesics, Some 1-Substituted 4-Phenyl-4-Propionoxypiperidines", Journal of Medicinal and Pharmaceutical Chemistry, Sep. 1962, 5:913-919.
Caratelli et al., "FCGamma Chimeric Receptor-Engineered T Cells: Methodology, Advantages, Limitations, and Clinical Relevance", Frontiers in Immunology, Apr. 27, 2017, 8(Article ID457), pp. 1-8.
CAS No. 18226-42-1, "1,3,5-Tris(bromomethyl)benzene", Chemical Book, Retrieved from: https://www.chemicalbook.com/ProductChemicalPropertiesCB0500171_EN.htm, 2023, 2 pages.
Center for Pancreatic and Biliary Diseases, "Bile Duct Cancer", University of Southern California, Department of Surgery, Dec. 7, 2017, Retrieved from: https://web.archive.org/web/20171207023733/http://www.surgery.usc.edu:80/divisions/tumor/PancreasDiseases/web%20pages/BILIARY%20SYSTEM/cholangiocarcinoma.html, 3 pages.
Chabner et al., "Initial Clinical Trials of Maytansine, an Antitumor Plant Alkaloid", Cancer Treat Reports, Mar. 1978, 62(3):429-433.
Chahinian et al., "Phase I Study of Weekly Maytansine Given by Iv Bolus or 24-Hour Infusion", Cancer Treatment Reports, Nov./Dec. 1979, 63(11-12):1953-1960.
Challita-Eid et al., "Enfortumab Vedotin Antibody-Drug Conjugate Targeting Nectin-4 Is a Highly Potent Therapeutic Agent in Multiple Preclinical Cancer Models", Cancer Research, May 15, 2016, 76(10):3003-3013.
Chandrasekar, "Bladder Cancer", Merck Manual, Retrieved form: https://www.merckmanuals.com/professional/genitourinary-disorders/genitourinary-cancers/bladder-cancer, Oct. 2023, 6 pages.
Chandrasekar, "Kidney Cancer", Merck Manual, Retrieved from: https://www.merckmanuals.com/home/kidney-and-urinary-tract-disorders/cancers-of-the-kidney-and-genitourinary-tract/kidney-cancer, Sep. 2022, pp. 1-4.
Chandrasekar, "Prostate Cancer", Merck Manual, Retrieved from: https://www.merckmanuals.com/professional/genitourinary-disorders/genitourinary-cancers/prostate-cancer, Oct. 2023, 11 pages.
Chang et al., "Subtiligase: A tool for semisynthesis of proteins", Proc. Natl. Acad. Sci., Dec. 1994, 91(26):12544-12548.
Chemnitz et al., "RNA fingerprints provide direct evidence for the inhibitory role of TGFBeta and PD-1 on CD4+ T cells in Hodgkin lymphoma", Blood, Nov. 1, 2007, 110(9):3226-3233.
Chen et al., "Abstract A8: Novel Multimers of Bicyclic Peptides Cluster and Activate CD137 (4-1BB): A Costimulatory T-Cell Checkpoint Receptor", PEGS, Nov. 12, 2018, pp. 1-7.
Chen et al., "Association of FCGR3A and FCGR3B Copy Number Variations With Systemic Lupus Erythematosus and Rheumatoid Arthritis in Taiwanese Patients", Arthritis & Rheumatology, Nov. 2014, 66(11):3113-3121.
Chen et al., "Cell-penetrating peptides in drug development: enabling intracellular targets", Biochemical Society Transactions, 2007, 35(4):821-825.
Chen et al., "The Bicycle Platform: an efficient technology to generate high affinity, high selectivity molecules (Bicycles®) with unique drug like properties that are amenable to conjugation", Retrieved from: https://www.bicycletherapeutics.com/wp-content/uploads/16_PEGS-Bicycle_-30-04-2017-poster.pdf, Apr. 30, 2017, pp. 1-10.
Cheng et al, "Memorial Sloan Kettering-Integrated Mutation Profiling of Actionable Cancer Targets (MSK-Impact): A Hybridization Capture-Based Next-Generation Sequencing Clinical Assay for Solid Tumor Molecular Oncology", The Journal of Molecular Diagnostics, May 2015, 17(3):251-264.
Chinnery et al., "Viral antigen mediated NKp46 activation of NK cells results in tumor rejection via NK-DC crosstalk", Oncoimmunology, Sep. 2012, 1(6):874-883.
Chung et al., "Bicycle synthesis through peptide macrocyclization using aziridine aldehydes followed by late stage disulfide bond installation", Med. Chem. Commun., 2013, 4(7):1124-1128.
Clarkson et al., "Treatment of Refractory Immune Thrombocytopeniaurpura with an Anti-Fc Gamma-Receptor Antibody", The New England Journal of Medicine, May 8, 1986, 314(19):1236-1239.
Claus et al., "Tumor-targeted 4-1BB agonists for combination with T cell bispecific antibodies as off-the-shelf therapy", Science Translational Medicine, Jun. 12, 2019, 11(496):eaav5989, pp. 1-12.
Clynes et al., "Inhibitory Fc receptors modulate in vivo cytotoxicity against tumor targets", Nature Medicine, Apr. 2000, 6(4):443-446.
Cohen et al., "Abstract 2: Quantitation of CD137 and Nectin-4 expression across multiple tumor types to support indication selection for BT7480, a Bicycle tumor-targeted immune cell agonist™M (Bicycle TICA™)", SITC, Nov. 12, 2021, pp. 1-7.
Cohen et al., "Abstract 5555: Development of a CD137 receptor occupancy assay to support the phase I/II study of BT7480, a Bicycle® tumor-targeted immune cell agonist (Bicycle TICA™)", American Association of Cancer Research, Apr. 8, 2022, pp. 1-6.
Cohen et al., "Abstract A65: Development of a CD137 receptor occupancy assay to support the phase I/II study of BT7480, a Bicycle tumor-targeted immune cell agonist® (Bicycle TICA®)", AACR-BC-EORTC, Oct. 26, 2022, pp. 1-7.
Cohen, "Translating preclinical findings into clinical biomarker assays to support the Phase I/II study of BT7480, a Bicycle tumor-targeted immune cell agonist®", World Clinical Biomarkers & CDx Summit, Sep. 28, 2022, 21 pages.
Cohen, "Turning preclinical findings into clinic-ready biomarker assays to support BT7480 development", Markets and Markets Biomarker and Companion Diagnostics Conference, Feb. 15, 2023, 21 pages.
Committee for Medicinal Products for Human Use (CHMP), "Assessment Report: Kadcyla; International non-proprietary name: Trastuzumab emtansine; Procedure No. EMEA/H/C/002389/0000", European Medicines Agency, Sep. 19, 2013; EMA/749228/2013, pp. 1-121.

(56) References Cited

OTHER PUBLICATIONS

Cook et al., “Abstract 5764: Pharmacokinetic (PK) assessment of BT1718 : A phase 1/2a study of BT1718, a first in class bicycle toxin conjugate (BTC), in patients with advanced solid tumours”, EMSO, Sep. 28, 2019, pp. 1-4.
Cook et al., “Pharmacokinetic (PK) assessment of BT1718: A Phase 1/II a study of BT1718, a first in class bicycle toxin conjugate (BTC), in patients (pts) with advanced solid tumours”, Annals of Oncology, Oct. 2019, 30(supplement 5):v174, 1 page.
Cooke, “Bicycles as precision guided therapeutics”, UK Symposium: Advancing Drug Discovery for Oncology, Mar. 13, 2023, 15 pages.
Cortes et al., “Phase II study of the Halichondrin B Analog Eribulin Mesylate in Patients With Locally Advanced or Metastatic Breast Cancer Previously Treated With an Anthracycline, a Taxane, and Capecitabine”, Journal of Clinical Oncology, Sep. 1, 2010, 28(25):3922-3928.
Costello et al., “Defective expression and function of natural killer cell-triggering receptors in patients with acute myeloid leukemia”, Blood, May 15, 2002, 99(10):3661-3667.
Crameri et al., “Construction and evolution of antibody-phage libraries by DNA shuffling”, Nature Medicine, Jan. 1996, 2(1):100-102.
Cui, “A New Challenging and Promising Era of Tyrosine Kinase Inhibitors”, ACS Medicinal Chemistry Letters, 2014, 5(4):272-274.
Curiel et al., “Blockade of B7-H1 improves myeloid dendritic cell-mediated antitumor immunity”, Nature Medicine, May 2003, 9(5):562-567.
Davies et al., “Antibody VH Domains as Small Recognition Units”, Biotechnology, May 13, 1995, 13(5):475-479.
Davis et al., “Natural Killer Cells Unleashed: Checkpoint receptor blockade and BiKE/TriKE utilization in NK-mediated anti-tumor immunotherapy”, Semin Immunol., Jun. 2017, 31:64-75.
Dawson et al., “Synthesis of Proteins by Native Chemical Ligation”, Science, Nov. 4, 1994, 266(5186):776-779.
De Kruif et al., “Selection and Application of Human Single Chain Fv Antibody Fragments from a Semi-synthetic Phage Antibody Display Library with Designed CDR3 Regions”, Journal of Molecular Biology, 1995, 248(1):97-105.
De la Pena et al., “Expression of the Matrix Metalloproteases 2, 14, 24, and 25 and Tissue Inhibitor 3 as Potential Molecular Markers in Advanced Human Gastric Cancer”, Disease Markers, 2014, 2014(Article ID 285906), pp. 1-9.
Debre et al., “Infusion of Fc Gamma fragments for treatment of children with acute immune thrombocytopeniaurpura”, Lancet, 1993, 342(8877):945-949.
Derossi et al., “The Third Helix of the Antennapedia Homeodomain Translocates Through Biological Membranes”, The Journal of Biological Chemistry, Apr. 8, 1994, 269(14):10444-10450.
Dharmadhikari et al., “CD137 and CD137L signals are main drivers of type 1, cell-mediated immune responses”, Oncoimmunology, 2016, 5(4):e1113367, pp. 1-8.
Diamantis et al., “Antibody-drug conjugates—An emerging class of cancer treatment”, British Journal of Cancer, 2016, 114(4):362-367.
Diaz-Perlas et al., “Branched BBB-shuttle peptides: chemoselective modification of proteins to enhance blood-brain barrier transport”, Chemical Science, 2018, 9(44):8409-8415.
Dong et al., “Tumor-associated B7-H1 promotes T-cell apoptosis: A potential mechanism of immune evasion”, Nature Medicine, Aug. 2002, 8(8):793-800.
Dorfman etal., “Programmed Death-1 (PD-1) is a Marker of Germinal Center-associated T cells and Angioimmunoblastic T-cell Lymphoma”, Am J Surg Pathol., Jul. 2006, 30(7):802-810.
Drumm et al., “Genetic Variation and Clinical Heterogeneity in Cystic Fibrosis”, Annu. Rev. Pathol. Mech. Dis., 2012, 7:267-282.
Dubois et al., “New ways to image and target tumour hypoxia and its molecular responses”, Radiotherapy and Oncology, 2015, 116(3):352-357.
Dufort et al., “Abstract 1340: Modulation of the natural killer cell immune response to tumor with a synthetic tumor-immune cell agonist, NK-TICA®”, American Association for Cancer Research Annual Meeting, Apr. 8, 2024, pp. 1-6.
Dufort et al., “Abstract 15699: Generation of a Bicycle NK-TICATM, a novel NK cell engaging molecule designed to induce targeted tumor cytotoxicity”, SITC, Nov. 12, 2022, pp. 1-5.
Dufort et al., Abstract 1806: Modulation of the natural killer (NK) cell immune response to tumor with novel synthetic tumor-immune cell agonist, NK-TICA™, American Association for Cancer Research Annual Meeting, Apr. 17, 2023, pp. 1-7.
Dufort et al., “Abstract 4233: Generation of a Bicycle NK-TICA™, a novel NK cell engaging molecule designed to induce targeted tumor cytotoxicity”, American Association for Cancer Research, Apr. 8, 2022, pp. 1-5.
Dufort, “Bicycles: Bispecific, Precision-guided NK Cell Activators for the Treatment of Solid Tumors”, Innate Killer Summit, Mar. 29, 2023, 23 pages.
Eagan et al., “Early Clinical Study of an Intermittent Schedule for Maytansine (NSC-153858): Brief Communication”, Journal of the National Cancer Institute, Jan. 1978, 60(1):93-96.
Eder et al., “Bicyclic Peptides as a New Modality for Imaging and Targeting of Proteins Overexpressed by Tumors”, Cancer Res., Feb. 15, 2019, 79(4):841-852.
Eder et al., “OP337: A phage display derived stabilised bicyclic peptide targeting MMP-14 shows high imaging contrast in small animal PET imaging”, In European Journal of Nuclear Medicine and Molecular Imaging, 2015, 42 (Suppl 1):S140-S141.
Eisenhauer et al., “New response evaluation criteria in solid tumours: Revised RECIST guideline (version 1.1)”, European Journal of Cancer, 2009, 45(2):228-247.
Ellenrieder et al., “Role of MT-MMPs and MMP-2 in Pancreatic Cancer Progression”, International Journal of Cancer, 2000, 85(1):14-20.
Elson-Schwab et al., “Guanidinylated Neomycin Delivers Large, Bioactive Cargo into Cells through a Heparan Sulfate-Dependent Pathway”, The Journal of Biological Chemistry, May 4, 2007, 282(18):13585-13591.
Evans et al., “Abstract CT253: Phase 1/2 study of the safety, pharmacokinetics, and preliminary clinical activity of BT7480 in patients with Nectin-4 associated advanced malignancies”, American Association for Cancer Research Annual Meeting, Apr. 18, 2023, pp. 1-5.
Fauriat et al., “Deficient expression of NCR in NK cells from acute myeloid leukemia: evolution during leukemia treatment and impact of leukemia cells in NCRdull phenotype induction”, Blood, Jan. 1, 2007, 109(1):323-330.
Fehrenbacher et al., “Atezolizumab versus docetaxel for patients with previously treated non-small-cell lung cancer (Poplar): A multicentre, open-label, phase 2 randomised controlled trial”, The Lancet, Apr. 30, 2016, 387(10030):1837-1846.
Felices et al., “Generation of BiKEs and TriKEs to Improve NK Cell-Mediated Targeting of Tumor Cells”, Chapter 28, Methods Molecular Biology, 2016, 1441:333-346.
Felices et al., “Novel CD19-targeted TriKE restores NK cell function and proliferative capacity in CLL”, Blood Advances, Mar. 26, 2019, 3(6):897-907.
Fiacco et al., “N-Methyl Scanning Mutagenesis Generates Protease-Resistant G Protein Ligands with Improved Affinity and Selectivity”, ChemBioChem, Sep. 22, 2008, 9(14):2200-2203.
Flaherty et al., “Nonclinical Evaluation of GMA161—An Antihuman CD16 (FcGammaRIII) Monoclonal Antibody for Treatment of Autoimmune Disorders in CD16 Transgenic Mice”, Toxicological Sciences, 2012, 125(1):299-309.
Forsberg et al., “CD137 Plays Both Pathogenic and Protective Roles in Type 1 Diabetes Development in NOD Mice”, The Journal of Immunology, 2017, 198(10):3857-3868.
Francis et al., “Bone and Soft Tissue Sarcomas: UK Incidence and Survival: 1996-2010”, National Cancer Intelligence Network, Nov. 2013, 17 pages.
Frigerio, “Expanding the Potential of ADCs: Bicyclic Peptide (Bicycle®) Toxin Conjugates May Offer Advancements Over Traditional ADCs”, World ADC, Mar. 20, 2023, 28 pages.
Frigerio, “Targeting Tumors with Bicycle Conjugates”, PEGS Boston, May 17, 2023, 31 pages.

(56) References Cited

OTHER PUBLICATIONS

Fumet et al., "Phase Ib/II trial evaluating the safety, tolerability and immunological activity of durvalumab (MEDI4736) (anti-PD-L1) plus tremelimumab (anti-CTLA-4) combined with FOLFOX in patients with metastatic colorectal cancer", ESMO open, 2018, 3(4):e000375, pp. 1-9.
Galsky et al., "Phase I Trial of the Prostate-Specific Membrane Antigen-Directed Immunoconjugate MLN2704 in Patients With Progressive Metastatic Castration-Resistant Prostate Cancer", Journal of Clinical Oncology, May 1, 2008, 26(13):2147-2154.
Garcia-Iglesias et al., "Low NKp30, NKp46 and NKG2D expression and reduced cytotoxic activity on NK cells in cervical cancer and precursor lesions", BMC Cancer, 2009, 9:186, pp. 1-8.
Gauthier et al., "Multifunctional Natural Killer Cell Engagers Targeting NKp46 Trigger Protective Tumor Immunity", Cell, Jun. 13, 2019, 177(7):1701-1713.
Gelb et al., "Abstract 391: Molecular-based enrichment strategy for Nectin-4 targeted Bicycle toxin conjugate BT8009", Cancer Res., Jul. 1, 2021, 81(13 suppl):391, pp. 1-8.
Gelb et al., "Abstract A047: MT1-MMP Immunohistochemistry (IHC) analysis of tumor microarrays (TMAs) using a novel scoring system guides patient selection for BT1718 expansion cohorts", AACR-NCI-EORTC, Oct. 27, 2019, pp. 1-7.
Gelb et al., "Abstract A047: MT1-MMP Immunohistochemistry (IHC) analysis of tumor microarrays(TMAs) using a novel scoring system guides patient selection for BT1718 expansion cohorts", Molecular Cancer Therapeutics, 2019, 18(12_Supplement):A047, 2 pages.
GenBank Accession No. CZR33441.1, "uncharacterized protein FPRO_01747 [Fusariurn proliferatum ET1]", National Center for Biotechnology Information, Retrieved from: https://www.ncbi.nlm.nih.gov/protein/1111492376, Dec. 6, 2016, 1 page.
GenPath Diagnostics, "Solid Tumors", Retrieved from: https://genpathdiagnostics.com/patients/oncology/solid-tumors/, 2023, pp. 1-3.
Gentilucci et al., "Chemical Modifications Designed to Improve Peptide Stability: Incorporation of Non-Natural Amino Acids, Pseudo-Peptide Bonds, and Cyclization", Current Pharmaceutical Design, 2010, 16:3185-3203.
Gfeller et al., "Current tools for predicting cancer-specific T cell immunity", Oncoimmunology, 2016, 5(7):e1177691, 9 pages.
Gleason et al., "CD16xCD33 bispecific killer cell engager (BiKE) activates NK cells against primary MDS and MDSC CD33+ targets", Blood, May 8, 2014, 123(19):3016-3026.
Gokel et al., "Crown Ethers: Sensors for Ions and Molecular Scaffolds for Materials and Biological Models", Chem. Rev., 2004, 104(5):2723-2750.
Gradishar et al., "Significantly Longer Progression-Free Survival With nab-Paclitaxel Compared With Docetaxel as First-Line Therapy for Metastatic Breast Cancer", Journal of Clinical Oncology, Aug. 1, 2009, 27(22):3611-3619.
Gresh, "Neuroblastoma", Merck Manual., Retrieved from: https://www.msdmanuals.com/en-in/professional/pediatrics/pediatric-cancers/neuroblastoma, Sep. 2022, 4 pages.
Griffiths et al., "Isolation of high affinity human antibodies directly from large synthetic repertoires", EMBO Journal, 1994, 13(14):3245-3260.
Grisold et al., "Peripheral neuropathies from chemotherapeutics and targeted agents: diagnosis, treatment, and prevention", Neuro-Oncology, Sep. 2012, 14(suppl_4):iv45-iv54.
Gu et al., "The influence of the penetrating peptide iRGD on the effect of paclitaxel-loaded MT1-AF7p-conjugated nanoparticles on glioma cells", Biomaterials, 2013, 34(21):5138-5148.
Gupta et al, "Intracellular delivery of large molecules and small particles by cell-penetrating proteins and peptides", Advanced Drug Delivery Reviews, 2005, 57(4):637-651.
Hacker et al., "Highly-constrained bicyclic scaffolds for the discovery of protease-stable peptides via mRNA display", ACS Chem. Biol., Mar. 17, 2017, 12(3):795-804.
Hadjicharalambous et al., "Investigating Penetration and Antimicrobial Activity of Vector Bicycle Conjugates", ACS Infectious Diseases, Jun. 12, 2024, 10(7):2381-2389.
Hamanishi et al., "Programmed cell death 1 ligand 1 and tumor-infiltrating CD8+ T lymphocytes are prognostic factors of human ovarian cancer", PNAS, Feb. 27, 2007, 104(9):3360-3365.
Han et al., "Altered NKp30, NKp46, NKG2D, and DNAM-1 Expression on Circulating NK Cells Is Associated with Tumor Progression in Human Gastric Cancer", Journal of Immunology Research, Sep. 3, 2018, 2018(Article ID 6248590), 9 pages.
Hanna et al., "Randomized Phase III Trial of Pemetrexed Versus Docetaxel in Patients With Non-Small-Cell Lung Cancer Previously Treated With Chemotherapy", Journal of clinical oncology, May 1, 2004, 22(9):1589-1597.
Harrison et al., "Abstract 5144: BT1718, a novel bicyclic peptide-maytansinoid conjugate targeting MT1-MMP for the treatment of solid tumours: Design of bicyclic peptide and linker selection", AACR Annual meeting, Apr. 1, 2017, pp. 1-7.
Harrison et al., "Discovery and development of BT1718, a novel bicyclic peptidemaytansinoid conjugate targeting MT1-MMP for the treatment of solid tumours: In vitro and in vivo activities", PEGS, Apr. 30, 2017, 1 page.
Hart et al., "Cell Binding and Internalization by Filamentous Phage Displaying a Cyclic Arg-Gly-Asp-containing Peptide", The Journal of Biological Chemistry, Apr. 29, 1994, 269(17):12468-12474.
Hart et al., "De novo identification of lipid II binding lipopeptides with antibacterial activity against vancomycin-resistant bacteria", Chemical Science, 2017, 8(12):7991-7997.
Hasmim et al., "Critical role of tumor microenvironment in shaping NK cell functions: implication of hypoxic stress", Frontiers in Immunology, Sep. 23, 2015, 6(Article 482), pp. 1-9.
He et al., "Matrix Metalloproteinase-14 Is a Negative Prognostic Marker for Patients with Gastric Cancer", Digestive diseases and sciences, 2013, 58(5):1264-1270.
Helft et al., "A Phase I Study of Cantuzumab Mertansine Administered as a Single Intravenous Infusion Once Weekly in Patients with Advanced Solid Tumors", Clinical Cancer Research, Jul. 1, 2004, 10(13):4363-4368.
Henriques et al., "Functional characterization of peripheral blood dendritic cells and monocytes in systemic lupus erythematosus", Rheumatology International, 2012, 32(4):863-869.
Herbst et al., "Pembrolizumab versus docetaxel for previously treated, PD-L 1-positive, advanced non-small-cell lung cancer (KEYNOTE-010): a randomised controlled trial", Lancet, Apr. 9, 2016, 387(10027):1540-1550.
Hershman, "Thyroid Cancers", Merck Manual, Retrieved from: https://www.merckmanuals.com/professional/endocrine-and-metabolic-disorders/thyroid-disorders/thyroid-cancers, Sep. 2020, pp. 1-3.
Hess et al., "Backbone Cyclic Peptidomimetic Melanocortin-4 Receptor Agonist as a Novel Orally Administrated Drug Lead for Treating Obesity", Journal of Medicinal Chemistry, 2008, 51(4):1026-1034.
Hill et al., "Constraining Cyclic Peptides to Mimic Protein Structure Motifs", Angewandte Chemie International Edition, Nov. 24, 2014, 53(48):13020-13041.
Hinner et al., "Tumor-Localized Costimulatory T-Cell Engagement by the 4-1BB/HER2 Bispecific Antibody-Anticalin Fusion PRS-343", Clinical Cancer Research , Oct. 1, 2019, 25(19):5878-5889.
Hirano et al., "Blockade of B7-H1 and PD-1 by Monoclonal Antibodies Potentiates Cancer Therapeutic Immunity", Cancer Research, Feb. 1, 2005, 65(3):1089-1096.
Ho et al., "Expression of CD137 on Hodgkin and Reed-Sternberg Cells Inhibits T-cell Activation by Eliminating CD137 Ligand Expression", Cancer Research, Jan. 15, 2013, 73(2):652-661.
Hoogenboom et al., "By-passing Immunisation: Human Antibodies from Synthetic Repertoires of Germline VH Gene Segments Rearranged in Vitro", Journal of Molecular Biology, 1992, 227(2):381-388.
Hsu et al., "Efficacy of plasmin-treated intravenous gamma-globulin for therapy of Kawasaki syndrome", The Pediatric Infectious Disease Journal, Jun. 1993, 12(6):509-512.

(56) References Cited

OTHER PUBLICATIONS

Hu et al., "Lessons Learned from Molecular Scaffold Analysis", Journal of Chemical Information and Modeling, 2011, 51(8):1742-1753.
Hu-Lieskovan et al., "New Combination Strategies Using Programmed Cell Death 1/Programmed Cell Death Ligand 1 Checkpoint Inhibitors as a Backbone", The Cancer Journal, Jan./Feb. 2017, 23(1):10-22.
Hurov et al., "Abstract 1340: BT7455, a fully synthetic Bicycle tumor-targeted immune cell agonist®, leads to potent EphA2-dependent CD137 agonism and robust anti-tumor efficacy", SITC, Nov. 10, 2022, pp. 1-6.
Hurov et al., "Abstract 3257: Activation of 4-1BB using multivalent and tumour targeted bicyclic peptides", American Association of Cancer Research, Apr. 2, 2019, pp. 1-4.
Hurov et al., "Abstract 3257: Activation of CD137 using multivalent and tumor targeted Bicyclic peptides", Cancer Res, Jul. 1, 2019, 79(13_Supplement):3257, 3 pages.
Hurov et al., "Abstract 700: EphA2/CD137 Bicycle® tumor-targeted immune cell agonists (TICAs™) induce tumor regressions, immunogenic memory, and reprogramming of the tumor immune microenvironment", SITC, Nov. 9, 2020, pp. 1-4.
Hurov et al., "Abstract P398: Activation of the T cell costimulatory protein CD137 using multivalent bicyclic peptides", SITC, Nov. 6, 2018, pp. 1-5.
Hurov et al., "Abstract P782: A novel fully synthetic dual targeted Nectin-4/4-1BB Bicycle® peptide induces tumor localized 4-1BB agonism", SITC, Nov. 9, 2019, pp. 1-6.
Hurov et al., "BT7480, a novel fully synthetic Bicycle tumor-targeted immune cell agonist™ (Bicycle TICA™) induces tumor localized CD137 agonism", Journal for ImmunoTherapy of Cancer, 2021, 9(11):e002883, pp. 1-13.
Hurov et al., "Poster 1728: Nectin-4-dependent immune cell stimulation and anti-tumor efficacy by BT7480, a Nectin-4/CD137 Bicycle® tumor-targeted immune cell agonist (TICA™)", American Association of Cancer Research, Apr. 12, 2021, pp. 1-6.
Hurov, "BT7480, a novel and fully synthetic Bicycle tumor-targeted immune cell agonist®", Festival of Biologics, Nov. 4, 2022, 23 pages.
Ide et al., "A novel method for artificial lipid-bilayer formation", Biosensors and Bioelectronics, 2005, 21(4):672-677.
Inman et al., "PD-L1 (B7-H1) Expression by Urothelial Carcinoma of the Bladder and BCG-Induced Granulomata: Associations with Localized Stage Progression", Cancer, Apr. 15, 2007, 109(8):1499-1505.
Ip et al., "Atypical Localization of Membrane Type 1-Matrix Metalloproteinase in the Nucleus Is Associated With Aggressive Features of Hepatocellular Carcinoma", Molecular Carcinogenesis, 2007, 46(3):225-230.
Izawa et al., "$H_2O_2$ production within tumor microenvironment inversely correlated with infiltration of CD56(dim) NK cells in gastric and esophageal cancer: possible mechanisms of NK cell dysfunction", Cancer Immunology, Immunotherapy, 2011, 60(12):1801-1810.
Jackson et al., "Using the Lessons Learned From the Clinic to Improve the Preclinical Development of Antibody Drug Conjugates", Pharmaceutical research, 2015, 32(11):3458-3469.
Jespers et al., "Selection of optical biosensors from chemisynthetic antibody libraries", Protein Engineering, Design & Selection, 2004, 17(10):709-713.
Johnson et al., "Relationships between drug activity in NCI preclinical in vitro and in vivo models and early clinical trials", British Journal of Cancer, 2001, 84(10):1424-1431.
Jones et al., "Randomized Phase III Study of Docetaxel Compared With Paclitaxel in Metastatic Breast Cancer", Journal of Clinical Oncology, Aug. 20, 2005, 23(24):5542-5551.
Jones et al., "Targeting membrane proteins for antibody discovery using phage display", Scientific Reports, May 18, 2016, 6(Article No. 26240), pp. 1-11.
Kamat et al., "The Clinical Relevance of Stromal Matrix Metalloproteinase Expression in Ovarian Cancer", Clinical Cancer Research, Mar. 15, 2006, 12(6):1707-1714.
Kamijo et al., "Aberrant CD137 ligand expression induced by GATA6 overexpression promotes tumor progression in cutaneous T-cell lymphoma", Blood, Sep. 7, 2018, pp. 1-46.
Kanakia et al., "Development of CD137 (4-1BB) receptor occupancy assay using fluorescently labeled Bicycles®", AACR Tumor Immunology & Immunotherapy, Oct. 19, 2020, 5 pages.
Kanazawa et al., "Non-obese-diabetic mice: immune mechanisms of pancreatic Beta-cell destruction", Diabetologia, 1984, 27:113-115.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)", Journal of Clinical Oncology, 2016, 34(4 suppl_5), pp. 1-4.
Kang et al., "Anti-CD137 Suppresses Tumor Growth by Blocking Reverse Signaling by CD137 Ligand", Cancer Research, Nov. 1, 2017, 77(21):5989-6000.
Keen, "A novel fully synthetic dual targeted Nectin-4/4-1BB Bicycle® peptide induces tumor localized 4-1BB agonism", SITC, Nov. 6-10, 2019, 19 pages.
Keen, "BT5528, an EphA2-targeting Bicycle® Toxin Conjugate", World ADC congress, Oct. 11, 2019, 24 pages.
Keen, "BT7480, a novel Nectin-4 dependent agonist of the immune cell costimulatory receptor CD137", AACR Annual Meeting, Apr. 10-15 and May 17-21, 2021, 23 pages.
Keith, "Lung Carcinoma", Merck Manual, Retrieved from: https://www.merckmanuals.com/professional/pulmonary-disorders/tumors-of-the-lungs/lung-carcinoma, May 2023, pp. 1-16.
Kell, "The Transporter-Mediated Cellular Uptake and Efflux of Pharmaceutical Drugs and Biotechnology Projects: How and Why Phospholipid Bilayer Transport is Negligible in Real Biomembranes", Molecules, 2021, 26(5629), pp. 1-40.
Kellogg et al., "Disulfide-Linked Antibody-Maytansinoid Conjugates: Optimization of In Vivo Activity by Varying the Steric Hindrance at Carbon Atoms Adjacent to the Disulfide Linkage", Bioconjugate Chemistry, 2011, 22(4):717-727.
Kerkela et al., "Differential patterns of stromelysin-2 (MMP-10) and MT1-MMP (MMP-14) expression in epithelial skin cancers", British Journal of Cancer, 2001, 84(5):659-669.
Kessenbrock et al., "Matrix Metalloproteinases: Regulators of the Tumor Microenvironment", Cell, Apr. 2, 2010, 141(1):52-67.
Khan et al., "Engineering Lipid Bilayer Membranes for Protein Studies", International Journal of Molecular Sciences, 2013, 14(11):21561-21597.
Kikuchi et al., "Immunohistochemical detection of membrane-type-1-matrix metalloproteinase in colorectal carcinoma", British Journal of Cancer, 2000, 83(2):215-218.
Kim et al., "Reverse signaling through the costimulatory ligand CD137L in epithelial cells is essential for natural killer cell-mediated acute tissue inflammation", PNAS, Jan. 3, 2012, 109(1):E13-E22.
Kim et al., "Synergistic Signals for Natural Cytotoxicity Are Required to Overcome Inhibition by c-Cbl ubiquitin ligase", Immunity, Feb. 26, 2010, 32(2):175-186.
Kleinau et al., "Induction and Suppression of Collagen-induced Arthritis is Dependent on Distinct FcGamma receptors", J Exp Med., May 1, 2000, 191(9):1611-1616.
Knight et al., "Three genes for lupus nephritis in NZB x NZW mice", Journal of Experimental Medicine, 1978, 147(6):1653-1660.
Konishi et al., "B7-H1 Expression on Non-Small Cell Lung Cancer Cells and Its Relationship with Tumor-Infiltrating Lymphocytes and Their PD-1 Expression", Clinical Cancer Research, Aug. 1, 2004, 10(15):5094-5100.
Koo et al., "Reduction of the CD16-CD56bright NK Cell Subset Precedes NK Cell Dysfunction in Prostate Cancer", PLoS One, Nov. 2013, 8(11):e78049, pp. 1-8.
Kreidieh et al., "Overview, prevention and management of chemotherapy extravasation", World Journal of Clinical Oncology, Feb. 10, 2016, 7(1):87-97.

(56) References Cited

OTHER PUBLICATIONS

Krishnamoorthy et al., "Breaking the Permeability Barrier of *Escherichia coli* by Controlled Hyperporination of the Outer Membrane", Antimicrobial Agents and Chemotherapy, 2016, 60(12):7372-7381.
Kristensson et al., "Novel Bicyclic Peptide Multimers Activate T Cell Costimulatory Protein CD137", Elrig Drug Discovery, Oct. 9, 2018, pp. 1-7.
Kristensson et al., "Novel Bicyclic Peptide Multimers Activate T Cell Costimulatory Protein CD137", Promega Biologics, Jul. 18, 2018, pp. 1-7.
Krop et al., "Trastuzumab emtansine versus treatment of physician's choice for pretreated HER2-positive advanced breast cancer (TH3RESA): a randomised, open-label, phase 3 trial", The Lancet Oncology, May 2, 2014, 15(7):689-699.
Kumara et al., "Fusarium proliferatum, an endophytic fungus from Dysoxylum binectariferum Hook.f, produces rohitukine, a chromane alkaloid possessing anti-cancer activity", Antonie van Leeuwenhoek, 2012, 101(2):323-329.
Kylvaja et al., "Penicillin binding protein 3 of *Staphylococcus aureus* NCTC 8325-4 binds and activates human plasminogen", BMC Research Notes, 2016, 9:389, 10 pages.
Lahdenranta et al., "Abstract 1356: Transcriptional profiling of Bicycle® tumor-targeted CD137 agonist-treated mouse tumors revealed an early and rapid activation of myeloid cells followed by infiltration of cytotoxic T cells into the tumor", SITC, Nov. 10, 2022, pp. 1-9.
Lahdenranta et al., "Abstract 5301: Tumor-targeted activation of CD137 using Bicycle® molecules: New insights into mechanism of action and discovery of BT7455, a clinical candidate for the treatment of EphA2-expressing cancers", American Association for Cancer Research Annual Meeting, Apr. 9, 2024, pp. 1-5.
Lahdenranta et al., "Abstract A067: BT7480, a synthetic Bicycle tumor-targeted immune cell agonist® (Bicycle TICA®), induces reprogramming of the tumor immune microenvironment through tumor localized CD137 agonism", CICON, Sep. 29, 2022, pp. 1-9.
Lahdenranta et al., "Poster 1319: Rapid accumulation of cytotoxic payload in tumor tissue drives BT5528 activity in tumor models", American Association of Cancer Research, Apr. 12, 2021, pp. 1-4.
Lahdenranta et al., "Poster 1724: Microinjection of Nectin-4/CD137 tumor-targeted immune cell agonist (TICA™) activates the local tumor microenvironment", American Association of Cancer Research, Apr. 12, 2021, pp. 1-4.
Lahdenranta et al., "Poster 706: BT7480, a fully synthetic tumor-targeted immune cell agonist (TICA™) induces tumor localized CD137 agonism and modulation of tumor immune microenvironment", SITC, Nov. 9, 2020, pp. 1-6.
Landolt et al., "Clear Cell Renal Cell Carcinoma is linked to Epithelial-to-mesenchymal Transition and to Fibrosis", Physiological Reports, 2017, 5(11):e13305, pp. 1-18.
Lani et al., "Identification of high affinity, highly selective bicyclic peptides (Bicycles®) to transmembrane proteins using phage display screening on whole cells", PEGS , 2017, 1 page.
Lanman et al, "Analytical and Clinical Validation of a Digital Sequencing Panel for Quantitative, Highly Accurate Evaluation of Cell-Free Circulating Tumor DNA", PLoS One, Oct. 16, 2015, 10(10):e0140712, pp. 1-27.
Lau et al., "A penicillin-binding protein that can promote advanced-generation cephalosporin resistance and genome adaptation in the opportunistic pathogen Pseudomonas aeruginosa", International Journal of Antimicrobial Agents, 2020, 55(3):105896, pp. 1-8.
Laudanski et al., "Increased serum level of membrane type 1-matrix metalloproteinase (MT1-MMP/MMP-14) in patients with breast cancer", Folia histochemica et cytobiologica, 2010, 48(1):101-103.
Lea et al., "Fluorescence Polarization Assays in Small Molecule Screening", Expert Opinion in Drug Discovery, Jan. 2011, 6(1):17-32.
Leighton et al., "Pharmacology Review—Application No. 125427Orig1s000", Center for Drug Evaluation and Research, 2013, 79 pages.
Levi et al., "Characterization of tumor infiltrating Natural Killer cell subset", Oncotarget, 2015, 6(15):13835-13843.
Levine et al., "Methionine residues as endogenous antioxidants in proteins", Proc. Natl. Acad. Sci., Dec. 1996, 93(26):15036-15040.
Li et al., "A Novel Strategy for In Vitro Selection of Peptide-Drug Conjugates", Chemistry & Biology, Mar. 2003, 10(3):233-239.
Li et al., "Fluorescent Mu Selective Opioid Ligands from a Mixture Based Cyclic Peptide Library", ACS combinatorial science, 2012, 14(12):673-679.
Li et al., "Increasing Antimicrobial Activity of Nisin-based Lantibiotics Against Gram-negative Pathogens", Applied and Environmental Microbiology, 2018, 84(12), 39 pages.
Li et al., "Targeting the Fc receptor in autoimmune disease", Expert Opinion on Therapeutic Targets, 2014, 18(3):335-350.
Li et al., "The overexpression membrane type 1 matrix metalloproteinase is associated with the progression and prognosis in breast cancer", American Journal of Translational Research, 2015, 7(1):120-127.
Lian et al, "Screening Bicyclic Peptide Libraries for Protein-Protein Interaction Inhibitors: Discovery of a Tumor Necrosis Factor-alpha Antagonist", Journal of the American Chemical Society, 2013, 135(32):11990-11995.
Lian et al., "Cell-Permeable Bicyclic Peptide Inhibitors against Intracellular Proteins", Journal of the American Chemical Society, 2014, 136(28):9830-9833.
Linch et al., "OX40 agonists and combination immunotherapy: putting the pedal to the metal", Frontiers in Oncology, Feb. 2015, 5(Article 34), pp. 1-14.
Linde et al., "Structure-Activity Relationship and Metabolic Stability Studies of Backbone Cyclization and N-Methylation of Melanocortin Peptides", Biopolymers, 2008, 90(5):671-682.
Lindstrom et al., "Myasthenia Gravis", Advances in Immunology, 1988, 42:233-284.
Liu et al., "Abstract 3642: Tumor-antigen expression-dependent activation of the CD137 costimulatory pathway by bispecific DART proteins", Cancer Research, 2017, 77(13_Supplement):3642, pp. 1-5.
Liu et al., "Plasma cells from multiple myeloma patients express B7-H1 (PD-L1) and increase expression after stimulation with IFN-gamma and TLR ligands via a MyD88-, TRAF6-, and MEK-dependent pathway", Blood, Jul. 1, 2007, 110(1):296-304.
Lopus, "Antibody-DM1 conjugates as cancer therapeutics", Cancer Letters, 2011, 307(2):113-118.
Loriot et al., "Abstract TPS4619: A phase 2/3 study of Bicycle® Toxin Conjugate zelenectide pevedotin (BT8009) targeting Nectin-4 in patients with locally advanced or metastatic urothelial cancer (la/mUC) (Duravelo-2)", American Society of Clinical Oncology Annual Meeting, May 31-Jun. 4, 2024, 1 page.
Lovering et al., "Escape from Flatland: Increasing Saturation as an Approach to Improving Clinical Success", Journal of Medicinal Chemistry, 2009, 52(21):6752-6756.
Lovering, "Escape from Flatland 2: Complexity and promiscuity", Medicinal Chemistry Communication, 2013, 4(3):515-519.
Lowe, "Not Alphafold's Fault", blog—In the pipeline, Sep. 7, 2022, 6 pages.
Lowe, "The Good Sides and Bad Sides of Polar Compounds", blog—In the pipeline, Feb. 23, 2017, 15 pages.
Ludbrook, "Bicycle Toxin Conjugates to Target Solid Tumors", 3rd ADC Target Selection Summit, Dec. 6, 2023, 20 pages.
Luus et al., "Abstract 1832: EphA2-dependent CD137 agonism and anti-tumor efficacy by BT7455, a Bicycle tumor-targeted immune cell agonist®", American Association for Cancer Research Annual Meeting, Apr. 17, 2023, pp. 1-7.
M.D. Anderson Cancer Center, "Nivolumab and HPV-16 Vaccination in Patients With HPV-16 Positive Incurable Solid Tumors", ClinicalTrials.gov Identifier NCT02426892, Retrieved from: https://clinicaltrials.gov/ct2/show/study/NCT02426892, 2015, 14 pages.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):e1330235, 12 pages.

(56) References Cited

OTHER PUBLICATIONS

Macheboeuf et al., "Penicillin Binding Proteins: key players in bacterial cell cycle and drug resistance processes", FEMS Microbiol Rev., 2006, 30(5):673-691.
Mamessier et al., "Human Breast Tumor Cells Induce Self-Tolerance Mechanisms to Avoid NKG2D-Mediated and DNAM-Mediated NK cell Recognition", Cancer Research, Nov. 1, 2011, 71(21):6621-6632.
Manches et al., "In vitro mechanisms of action of rituximab on primary non-Hodgkin lymphomas", Blood, Feb. 1, 2003, 101(3):949-954.
Marks et al., "By-passing Immunization: Human Antibodies from V-gene Libraries Displayed on Phage", Journal of Molecular Biology, 1991, 222(3):581-597.
Maron et al., "H-2K Mutation Controls Immune Response Phenotype of Autoimmune Thyroiditis: Critical Expression of Mutant Gene Product in Both Thymus and Thyroid Glands", Journal of Experimental Medicine, Oct. 1980, 152(4):1115- 1120.
McDonnell, "Bicycles for precision guided delivery", Boulder Peptide Symposium, Nov. 9, 2022, 29 pages.
McFarlin et al., "Experimental Allergic Encephalomyelitis in the Rat: Response to Encephalitogenic Proteins and Peptides", Science, 1973, 179(4072):478-480.
McKean et al., "A Combined Phase I/II Study of BT8009 a Novel Bicycle® Toxin Conjugate with MMAE in Patients with Advanced Malignancies with Nectin-4", ASCO, Jun. 4, 2021, 1 page.
McKean et al., "BT8009-100 Phase I/II Study of Novel Bicyclic Peptide and MMAE Conjugate BT8009 in Patients with Advanced Malignancies Associated with Nectin-4 Expression", American Association for Cancer Research, Apr. 8-13, 2022, 17 pages.
McKean et al., "BT8009-100 Phase I/II Study of the Safety, Pharmacokinetics, & Preliminary Clinical Activity of BT8009 in Patients with Nectin-4 Expressing Advanced Malignancies", ESMO, Sep. 17, 2020, 1 page.
McKean, "A first in class phase I/II study of the novel bicyclic peptide and MMAE conjugate, BT5528, in patients with advanced malignancies associated with EphA2 expression", AACR-NCI-EORTC, Oct. 7-10, 2021, 19 pages.
Michel et al., "Expression of Soluble CD137 Correlates with Activation-Induced Cell Death of Lymphocytes", Cytokine, Jun. 2000, 12(6):742-746.
Micoine et al., "A General Strategy for Ligation of Organic and Biological Molecules to Dawson and Keggin Polyoxotungstates", Organic Letters, Jul. 18, 2007, 9(20):3981-3984.
Milowsky et al., "Phase 1/2 Multiple Ascending Dose Trial of the Prostate-Specific Membrane Antigen (PSMA)-Targeted Antibody Drug Conjugate MLN2704 in Metastatic Castration-Resistant Prostate Cancer", Urologic Oncology, Dec. 2016, 34(12):530.e15-530.e21, 16 pages.
Mistry et al., "Abstract 15523: Establishing the preclinical/translational PK/PD relationship for BT7480, a Nectin4/CD137 Bicycle tumor-targeted immune cell agonist™M (Bicycle TICA™)", SITC, Nov. 12, 2021, pp. 1-5.
Mistry et al., "Synthesis of Bicycle® Peptides using Gold-mediated Cysteine Arylation", European Peptide Synthesis Conference, Mar. 7, 2023, 1 page.
Mittler et al., "Anti-CD137 Antibodies in the Treatment of Autoimmune Disease and Cancer", Immunologic Research, 2004, 29(1-3):197-208.
Miyoshi et al., "Nectin and Nectin-Like Molecules: Biology and Pathology", American Journal of Nephrology, 2007, 27(6):590-604.
Mohammad et al., "Prognostic value of membrane type 1 and 2 matrix metalloproteinase expression and gelatinase A activity in bladder cancer", The International Journal of Biological Markers, 2010, 25(2):69-74.
Moore et al., "A novel bispecific antibody format enables simultaneous bivalent and monovalent co-engagement of distinct target antigens", MABS, Nov./Dec. 2011, 3(6):546-557.
Moraes et al., "Immune checkpoint inhibitors (anti PD-1 or anti PD-L1) versus chemotherapy for second- or third-line treatment of metastatic non-small cell lung cancer (Protocol)", Cochrane Database Systematic Reviews, 2017, (4):CD012644, pp. 1-11.
Moretta et al., "Surface NK receptors and their ligands on tumor cells", Seminars in Immunology, 2006, 18(3):151-158.
Morgan et al., "Fc gamma RIIIA-158V and rheumatoid arthritis: a confirmation study", Rheumatology, 2003, 42(4):528-533.
Mudd et al., "Bicyclic Peptides for Positron Emission Tomography (PET) Imaging of MT1-MMP Expressing tumours", PEGS, Apr. 30, 2017, 1 page.
Mudd et al., "Discovery of BT8009: A Nectin-4 Targeting Bicycle Toxin Conjugate for the Treatment of Cancer", Journal of Medicinal Chemistry, 2022, 65(21):14261-14970.
Mudd et al., "Gold-Mediated Multiple Cysteine Arylation for the Construction of Highly Constrained Bicycle Peptides", Bioconjugate Chemistry, 2022, 33(8):1441-1445.
Mudd et al., "Potent anti-tumor activity of a Lead-212 labelled MT1-MMP targeting Bicycle Radionuclide ConjugateTM", TIDES USA—Oligonucleotide, May 8, 2023, pp. 1-7.
Mugera et al., "Acute toxicity of maytansine in F344 rats", Cancer Treatment Reports, 1977, 61(7):1333-1338 (English Abstract Only).
Mullis et al., "Specific synthesis of DNA in Vitro via a Polymerase-Catalyzed Chain Reaction", Methods in Enzymology, 1987, 155:335-350.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate Expression of Activating Fc gamma receptors I and III and Inhibiting Fc gamma Receptor Type II in the Determination of Joint Inflammation and Cartilage Destruction During Immune Complex-Mediated Arthritis", Arthritis & Rheumatism, Jan. 2003, 48(1):255-265.
Nair et al., "Mimicry of Native Peptide Antigens by the Corresponding Retro-Inverso Analogs is Dependent on Their Intrinsic Structure and Interaction Propensities", The Journal of Immunology, 2003, 170(3):1362-1373.
Nakanishi et al., "Overexpression of B7-H1 (PD-L1) significantly associates with tumor grade and postoperative prognosis in human urothelial cancers", Cancer Immunology, Immunotherapy, 2007, 56(8):1173-1182.
Nam et al., "The Therapeutic Potential of 4-1BB (CD137) in Cancer", Current Cancer Drug Targets, 2005, 5(5):357-363.
Nayyar et al., "Overcoming Resistance to Natural Killer Cell Based Immunotherapies for Solid Tumors", Feb. 2019, 9(51), pp. 1-28.
Nestor Jr., "The Medicinal Chemistry of Peptides", Current Medicinal Chemistry, 2009, 16(33):4399-4418.
Newman et al., "Anti-Infectives Drug Discovery at Bicycle Therapeutics", ESCMID, Oct. 11, 2022, 1 page.
Newman, "Characterisation of novel, noncovalent cyclic peptide (Bicycles®) inhibitors of PBP3s from important Gram-negative pathogens", ESCMID, Oct. 11, 2022, 18 pages.
Ngo et al., "Abstract 333: Activity of the erythropoietin-producing hepatocellular A2 receptor (EphA2) targeting Bicycle® Toxin Conjugate (BTC™) BCY6033 in EGFR inhibitor resistant non-small cell lung cancer (NSCLC) patient derived xenografts", American Association for Cancer Research, Apr. 8, 2022, pp. 1-6.
Nguyen, "Pancreatic Cancer", Merck Manual, Retrieved from: https://merckmanuals.com/professional/gastrointestinal-disorders/tumors-of-the-gastrointestinal-tract/pancreatic-cancer?query=adenocarcinomas, Sep. 2022, 5 pages.
Nguyen, "Pancreatic Cancer", Merck Manual, Retrieved from: https://www.merckmanuals.com/home/digestive-disorders/tumors-of-the-digestive-system/pancreatic-cancer?query=pancreatic%20cancer, Mar. 2021, 4 pages.
NIH National cancer institute, "Cancer Prevention Overview (PDQ®)-Patient Version", Retrieved from: https://www.cancer.gov/about-cancer/causes-prevention/patient-prevention-overview-pdq#, 2023, 13 pages.
NIH National Human Genome Research Institute, "Animal Model", Retrieved from: https://www.genome.gov/genetics-glossary/Animal-Model, Oct. 21, 2023, 3 pages.
Nissim et al., "Antibody fragments from a 'single pot' phage display library as immunochemical reagents", The EMBO Journal, 1994, 13(3):692-698.

(56) References Cited

OTHER PUBLICATIONS

Nomi et al., "Clinical Significance and Therapeutic Potential of the Programmed Death-1 Ligand/Programmed Death-1 Pathway in Human Pancreatic Cancer", Clin Cancer Res., Apr. 1, 2007, 13(7):2151-2157.
Oehlke et al., "Cellular uptake of an alpha-helical amphipathic model peptide with the potential to deliver polar compounds into the cell interior non-endocytically", Biochimica et Biophysica Acta, 1998, 1414(1-2):127-139.
Okuyama et al., "Small-molecule mimics of an alpha-helix for efficient transport of proteins into cells", Nature Methods, Feb. 2007, 4(2):153-159.
Ortiz et al., "Elucidating the interplay between IgG-Fc valency and Fc gamma R activation for the design of immune complex inhibitors", Science Translational Medicine, Nov. 16, 2016, 8(365):365ra158, 14 pages.
Pahwa et al., "Monitoring and Inhibiting MT1-MMP during Cancer Initiation and Progression", Cancers, 2014, 6(1):416-435.
Palma et al., "CD137 and CD137 Ligand Constitutively Coexpressed on Human T and B Leukemia Cells Signal Proliferation and Survival", Int J Cancer., 2004, 108(3):390-398.
Papadopoulos et al., "Abstract TPS2689: A Combined Phase I/II Study of a Novel Bicycle Tumor-targeted Immune Cell Agonist® BT7480 in Patients with Nectin-4 Associated Advanced Malignancies", ASCO, Jun. 6, 2022, 1 page.
Park et al., "Abstract 3756: Small Synthetic, Multivalent Bicyclic Peptides That Activate T Cell Costimulatory Protein CD137", American Association of Cancer Research, Apr. 14, 2018, pp. 1-9.
Park et al., "Abstract 3756: Small Synthetic, Multivalent Bicyclic Peptides That Activate T Cell Costimulatory Protein CD137", Cancer Res., Jul. 1, 2018, 78(13_Supplement):3756, 2 pages.
Park et al., "Abstract 3756: Small Synthetic, Multivalent Bicyclic Peptides That Activate T Cell Costimulatory Protein CD137", ELRIG Drug Discovery, Oct. 9, 2018, pp. 1-9.
Pasero et al., "Highly effective NK cells are associated with good prognosis in patients with metastatic prostate cancer", Oncotarget, 2015, 6(16):14360-14373.
Pavlidou et al., "Nanodiscs Allow Phage Display Selection for Ligands to Non-Linear Epitopes on Membrane Proteins", PLOS One, Sep. 2013, 8(9):e72272, pp. 1-8.
Pavlova et al., "A role for PVRL4-driven cell-cell interactions in tumorigenesis", Elife., 2013, 2:e00358, pp. 1-24.
Pearson et al., "High-Level Clonal FGFR Amplification and Response to FGFR Inhibition in a Translational Clinical Trial", Cancer Discovery, Aug. 2016, 6(8):838-851.
Peng et al., "Combined features based on MT1-MMP expression, CD11b+ immunocytes density and LNR predict clinical outcomes of gastric cancer", Journal of Translational Medicine, 2013, 11(1):153, pp. 1-11.
Phichith et al., "Novel peptide inhibiting both TEM-1 beta-lactamase and penicillin-binding proteins", The FEBS Journal, 2010, 277(23):4965-4972.
Pivot et al., "Pooled analyses of eribulin in metastatic breast cancer patients with at least one prior chemotherapy", Annals of Oncology, 2016, 27(8):1525-1531.
Platonova et al., "Profound Coordinated Alterations of Intratumoral NK Cell Phenotype and Function in Lung Carcinoma", Cancer Research, 2011, 71(16):5412-5422.
Polakis, "Antibody Drug Conjugates for Cancer Therapy", Pharmacological Reviews, Jan. 2016, 68(1):3-19.
Poon et al., "Preclinical safety profile of trastuzumab emtansine (T-DM1): Mechanism of action of its cytotoxic component retained with improved tolerability", Toxicology and Applied Pharmacology, 2013, 273(2):298-313.
Poreba, "Protease-activated prodrugs: strategies, challenges, and future directions", The FEBS Journal, 2020, 287(10):1936-1969.
Pricop et al., "Differential Modulation of Stimulatory and Inhibitory Fc gamma Receptors on Human Monocytes by Th1 and Th2 Cytokines", The Journal of Immunology, 2001, 166(1):531-537.
Purdie et al., "Piperazinedione Formation from Esters of Dipeptides containing Glycine, Alanine, and Sarcosine: the Kinetics in Aqueous Solution", Journal of the Chemical Society, Perkin Transactions 2, 1973, 14:1845-1852.
Qi et al., "Serial determination of glomerular filtration rate in conscious mice using FITC-inulin clearance", American Journal of Physiology—Renal Physiology, 2004, 286(3):F590-F596.
Rajendran et al., "CD137 signaling in Hodgkin and Reed-Sternberg cell lines induces IL-13 secretion, immune deviation and enhanced growth", Oncoimmunology, 2016, 5(6):e1160188, 7 pages.
Rataj et al., "High-affinity CD16-polymorphism and Fc-engineered antibodies enable activity of CD16-chimeric antigen receptor-modified T cells for cancer therapy", British Journal of Cancer, 2019, 120(1):79-87.
Ravetch et al., "IgG Fc receptors", Annual Review of Immunology, 2001, 19:275-290.
Reagan-Shaw et al., "Dose translation from animal to human studies revisited", The FASEB Journal, 2007, 22(3):659-661.
Reinertsen et al., "B-Lymphocyte Alloantigens Associated with Systemic Lupus Erythematosus", The New England Journal of Medicine, Sep. 7, 1978, 299(10):515-518.
Remacle et al., "Membrane type I-matrix metalloproteinase (MT1-MMP) is internalised by two different pathways and is recycled to the cell surface", Journal of Cell Science, 2003, 116(19):3905-3916.
Repash et al., "BT7480, a novel fully synthetic tumor-targeted immune cell agonist (TICA™) induces tumor localized CD137 agonism", AACR Tumor Immunology & Immunotherapy, Oct. 19, 2020, 10 pages.
Rezvaya et al., "Abstract 1207: NKp46 engaging Bicycle NK-TICA® drives tumor targeted cytotoxicity", SITC, Nov. 10, 2022, 1 page.
Rhodes et al., "Bicyclic Peptides as Next-Generation Therapeutics", Chemistry—A European Journal, 2017, 23(52):12690-12703.
Riddle et al., "Tumor Cell Surface Display of Immunoglobulin Heavy Chain Fc by Gene Transfer as a Means to Mimic Antibody Therapy", Human Gene Therapy, Jul. 2005, 16(7):830-844.
Rietschoten et al., "Abstract 268: Small Synthetic, Multivalent Bicyclic Peptides That Activate T Cell Costimulatory Protein CD137", 35th European Peptide Symposium, Aug. 1, 2018, 1 page.
Rigby et al., "Abstract 4479: BT8009: A bicyclic peptide toxin conjugate targeting Nectin-4 (PVRL4) displays efficacy in preclinical tumor models", Cancer Res, 2019, 79(13_Supplement):4479, 3 pages.
Rigby et al., "Abstract C061: BT8009, a Bicycle® Toxin Conjugate targeting Nectin-4, shows target selectivity, and efficacy in preclinical large and small tumor models", AACR-NCI-EORTC, Oct. 29, 2019, pp. 1-9.
Rigby et al., "BT8009; A Nectin-4 Targeting Bicycle® Toxin Conjugate for Treatment of Solid Tumors", Molecular Cancer Therapeutics, 2022, 21(12):1-27.
Rigby, "Abstract 4479: BT8009: A bicyclic peptide toxin conjugate targeting Nectin-4 (PVRL4) displays efficacy in preclinical tumour models", AACR Annual Meeting, Apr. 2, 2019, 10 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, Oct. 2016, 7(Article 413), pp. 1-13.
Rodon et al., "Cantuzumab mertansine in a three-times a week schedule: a phase I and pharmacokinetic study", Cancer Chemotherapy and Pharmacology, 2008, 62(5):911-919.
Roth et al., "Docetaxel, Cisplatin, and Fluorouracil; Docetaxel and Cisplatin; and Epirubicin, Cisplatin, and Fluorouracil As Systemic Treatment for Advanced Gastric Carcinoma: A Randomized Phase II Trial of the Swiss Group for Clinical Cancer Research", Journal of Clinical Oncology, Aug. 1, 2007, 25(22):3217-3223.
Rothwell et al, "Utility of ctDNA to support patient selection for early phase clinical trials: the TARGET study", Nature Medicine, 2019, 25(5):738-743.
Rudgers et al., "Binding Properties of a Peptide Derived from beta-Lactamase Inhibitory Protein", Antimicrobial Agents Chemotherapy, Dec. 2001, 45(12):3279-3286.

(56) References Cited

OTHER PUBLICATIONS

Salmon et al., "Human Receptors for Immunoglobulin G: Key Elements in the Pathogenesis of Rheumatic Disease", Arthritis & Rheumatology, Apr. 2001, 44(4):739-750.
Santos et al., "Abstract 35472: Characterization of Nectin-4 protein expression in non-small cell lung cancer patients", AACR-BC-EORTC, Oct. 13, 2023, pp. 1-4.
Satoh et al., "Experimental Allergic Encephalomyelitis Mediated by Murine Encephalitogenic Cell Lines Specific for Myelin Proteolipid Apoprotein", The Journal of Immunology, Jan. 1, 1987, 138(1):179-184.
Scagliotti et al., "Phase III Study Comparing Cisplatin Plus Gemcitabine With Cisplatin Plus Pemetrexed in Chemotherapy-Naive Patients With Advanced-Stage Non-Small-Cell Lung Cancer", Journal of Clinical Oncology, Jul. 20, 2008, 26(21):3543-3551.
Schiller et al., "Comparison of Four Chemotherapy Regimens for Advanced Non-Small-Cell Lung Cancer", New England Journal of Medicine, Jan. 10, 2002, 346(2):92-98.
Schreiber et al., "Rapid, electrostatically assisted association of proteins", Nature Structural & Molecular Biology, May 1996, 3(5):427-431.
Seely et al., "Regulatory Forum Opinion Piece*: Dispelling Confusing Pathology Terminology: Recognition and Interpretation of Selected Rodent Renal Tubule Lesions", Toxicologic Pathology, 2015, 43(4):457-463.
Segal et al., "Results from an Integrated Safety Analysis of Urelumab, an Agonist Anti-CD137 Monoclonal Antibody", Clinical Cancer Research, Apr. 15, 2017, 23(8):1929-1936.
Seiki, "Membrane-type 1 matrix metalloproteinase: a key enzyme for tumor invasion", Cancer letters, 2003, 194(1):1-11.
Sepiashvili et al., "Potentially Novel Candidate Biomarkers for Head and Neck Squamous Cell Carcinoma Identified Using an Integrated Cell Line-based Discovery Strategy", Molecular & Cellular Proteomics, Aug. 2012, 11(11):1404-1415.
Shaabani et al., "A patent review on PD-1/PD-L1 antagonists: small molecules, peptides, and macrocycles (2015-2018)", Expert Opinion on Therapeutic Patents, Sep. 2018, 28(9):665-678.
Shah et al., "Abstract A28: Establishment of an ex vivo tissue culture platform as a preclinical model to assess the mechanism of action of Bicycle® tumor-targeted immune cell agonists in NSCLC", AACR-BC-EORTC, Oct. 26, 2022, pp. 1-8.
Shah et al., "Phase I study of IMGN901, a CD56-targeting antibody-drug conjugate, in patients with CD56-positive solid tumors", Investigational New Drugs, 2016, 34:290-299.
Shah, "Update on Metastatic Gastric and Esophageal Cancers", Journal of Clinical Oncology, 2015, 33(16):1760-1769.
Shao et al., "CD137 ligand, a member of the tumor necrosis factor family, regulates immune responses via reverse signal transduction", Journal of Leukocyte Biology, Jan. 2011, 89(1):21-29.
Shao et al., "Copy number variation is highly correlated with differential gene expression: a pan-cancer study", BMC Medical Genetics, Nov. 9, 2019, 20(1):175, pp. 1-14.
Sharma et al., "Plasmacytoid dendritic cells from mouse tumor-draining lymph nodes directly activate mature Tregs via indoleamine 2, 3-dioxygenase", The Journal of Clinical Investigation, Sep. 2007, 117(9):2570-2582.
Shen et al., "Evaluation of Phage Display Discovered Peptides as Ligands for Prostate-Specific Membrane Antigen (PSMA)", PLOS One, Jul. 2013, 8(7):e68339, pp. 1-8.
Shen et al., "Non-Clinical Disposition and Metabolism of DM1, a Component of Trastuzumab Emtansine (T-DM1), in Sprague Dawley Rats", Drug Metabolism Letters, 2015, 9(2):119-131.
Shimauchi et al., "Augmented expression of programmed death-1 in both neoplastic and non-neoplastic CD4+ T-cells in adult T-cell leukemia/lymphoma", International Journal of Cancer, 2007, 121(12):2585-2590.
Sibaud et al., "Pigmentary disorders induced by anticancer agents. Part I: chemotherapy", Annales de dermatologie et de venereologie, 2013, 140(3):183-196 (English Abstract Submitted).
Siddharth et al., "Nectin-4 is a breast cancer stem cell marker that induces WNT/beta-catenin signaling via Pi3k/Akt axis", International Journal of Biochemistry and Cell Biology, 2017, 89:85-94.
Silver, "Multi-targeting by monotherapeutic antibacterials", Nature Reviews, Drug Discovery, Jan. 2007, 6(1):41-55.
Singh et al., "Protein Engineering Approaches in the Post-Genomic Era", Current Protein and Peptide Science, 2017, 18(4):1-11.
Skynner et al., "BT1718, a novel Bicycle Drug Conjugate® shows potent anti-tumor activity in diverse cell-derived and patient-derived tumor xenograft models", PEGS, Apr. 30, 2017, 1 page.
Soderstrom et al., "CD137: A checkpoint regulator involved in atherosclerosis", Atherosclerosis, 2018, 272:66-72.
Solomons, "Organic Chemistry", 4th ed, 1988, p. 902, 3 pages.
Sordo-Bahamonde et al., "Mechanisms of Resistance to NK Cell Immunotherapy", Cancers, 2020, 12(4):893, pp. 1-25.
Stanczuk et al., "Abstract 1388: Utility of humanized animal models for in vivo evaluation of NK-TICA®, novel Bicycle® tumor-targeted immune cell agonist® (Bicycle TICA®) designed to engage NK cells", SITC, Nov. 10, 2022, pp. 1-6.
Stanczuk et al., "Abstract 1826: Development of in vivo models for evaluation of NK-TICATM, novel Bicycle® tumortargeted immune cell agonist® designed to engage NK cells", American Association for Cancer Research Annual Meeting, Apr. 17, 2023, pp. 1-6.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)", Blood, 2014, 124(21):1760, pp. 1-3.
Steck et al., "Inside-Out Red Cell Membrane Vesicles: Preparation and Purification", Science, Apr. 10, 1970, 168(3928):255-257.
Stojanovic et al., "Natural Killer Cells and Solid Tumors", Journal of Innate Immunity, 2011, 3(4):355-364.
Stringaris et al., "Leukemia-induced phenotypic and functional defects in natural killer cells predict failure to achieve remission in acute myeloid leukemia", Haematologica, 2014, 99(5):836-847.
Strome et al., "B7-H1 Blockade Augments Adoptive T-Cell Immunotherapy for Squamous Cell Carcinoma", Cancer Research, Oct. 1, 2003, 63(19):6501-6505.
Stuart et al., "Collagen Autoimmune Arthritis", Annual Review of Immunology, 1984, 2:199-218.
Su, "Key DMPK Attributes of BT7480, a Bicycle Tumor-targeted Immune Cell AgonistTM Targeting Nectin-4 and Agonizing CD137", NEDMDG symposium, May 31, 2023, 20 pages.
Sun et al., "NK cell receptor imbalance and NK cell dysfunction in HBV infection and hepatocellular carcinoma", Cellular & Molecular Immunology, 2015, 12(3):292-302.
Suojanen et al., "A novel and selective membrane type-1 matrix metalloproteinase (MT1-MMP) inhibitor reduces cancer cell motility and tumor growth", Cancer Biology & Therapy, Dec. 15, 2009, 8(24):2362-2370.
Tarazona et al., "Current progress in NK cell biology and NK cell-based cancer immunotherapy", Cancer Immunology, Immunotherapy, 2020, 69(5):879-899.
Tetu et al., "The influence of MMP-14, TIMP-2 and MMP-2 expression on breast cancer prognosis", Breast Cancer Research, 2006, 8(3), pp. 1-9.
Teufel et al., "Abstract 4920: Bicyclic Peptides for Positron Emission Tomography (PET) Imaging of MT1-MMP Expressing Tumors", American Association of Cancer Research, Apr. 1, 2017, pp. 1-8.
Thake et al., "Toxicity of Maytansine (NSC 153858) in Dogs and Monkeys", PB-US National Technical Information Service (1975), Feb. 28, 1975, 260 pages.
Thevenard et al., "The YSNSG cyclopeptide derived from tumstatin inhibits tumor angiogenesis by down-regulating endothelial cell migration", International Journal of Cancer, 2010, 126(5):1055-1066.
Thompson et al., "Costimulatory B7-H1 in renal cell carcinoma patients: Indicator of tumor aggressiveness and potential therapeutic target", PNAS, Dec. 7, 2004, 101(49):17174-17179.
Thornber, "Isosterism and Molecular Modification in Drug Design", Chem. Soc. Rev, 1979, 8(4):563-580.
Tiberghien, "Highlighting the Potential of Bicycle Conjugates to Target Solid Tumours", World ADC, Mar. 20, 2023, 24 pages.

(56) References Cited

OTHER PUBLICATIONS

Tolcher et al., "Cantuzumab Mertansine, a Maytansinoid Immunoconjugate Directed to the CanAg Antigen: A Phase I, Pharmacokinetic, and Biologic Correlative Study", Journal of Clinical Oncology, 2003, 21(2):211-222.
Toogood, "Small molecule immuno-oncology therapeutic agents", Bioorganic & Medicinal Chemistry Letters, 2018, 28(3):319-329.
Touati et al., "Phage Selection of Bicyclic Peptide Ligands and Development of a New Peptide Cyclisation Method", These No. 5536, Oct. 19, 2012, 117 pages.
Trouche et al., "Small Multivalent Architectures Mimicking Homotrimers of the TNF Superfamily Member CD40L: Delineating the Relationship between Structure and Effector Function," Journal of the American Chemical Society, 2007, 129(44):13480-13492.
Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry", Human pathology, 2008, 39(5):731-739.
Tugyi et al., "Partial D-amino acid substitution: Improved enzymatic stability and preserved Ab recognition of a MUC2 epitope peptide", PNAS, Jan. 11, 2005, 102(2):413-418.
Tutt et al., "Abstract S3-01: the TNT trial: a randomized phase III trial of carboplatin (C) compared with docetaxel (D) for patients with metastatic or recurrent locally advanced triple negative or BRCA1/2 breast cancer (CRUK/07/012)", Cancer Research, May 2015, 75(9_Suppl):S3-01, pp. 1-3.
Uhlenbroich et al., "Abstract 0000: NKp46 engaging Bicycle NK-TICA™ drives tumor targeted cytotoxicity", PEGS Boston, May 17, 2023, 1 page.
Uhlenbroich, "Bicycles—a modality for Tumor-Targeted Immune Cell Agonism", Antibody Engineering & Therapeutics, Jun. 12, 2023, 23 pages.
Ulasov et al., "Inhibition of MMP 14 potentiates the therapeutic effect of temozolomide and radiation in gliomas", Cancer Medicine, 2013, 2(4):457-467.
Ün, "Charakterisierung von Peptiden für die Bindung essentieller Penicillin-bindender Proteine und die Variationen der Linkerlänge einzelkettiger TetR Varianten", Friedrich-Alexander-Universitaet Erlangen-Nuernberg (Germany), 2010, 139 pages (With English Summary).
Upadhyaya et al., "Abstract 888: An integrative approach to optimize a synthetic EphA2-dependent CD137 agonist: Balancing potency, physiochemical properties, and pharmacokinetics to achieve robust anti-tumor activity", SITC, Nov. 12, 2021, pp. 1-7.
Upadhyaya et al., "Anticancer immunity induced by a synthetic tumor-targeted CD137 agonist", Journal for Immunotherapy of Cancer, 2021, 9(1):e001762, pp. 1-10.
Upadhyaya et al., "Discovery and Optimization of a Synthetic Class of Nectin-4-Targeted CD137 Agonists for Immuno-oncology", Molecular Cancer Therapeutics, 2022, 65:9858-9872.
Valko et al., "Application of biomimetic HPLC to estimate lipophilicity, protein and phospholipid binding of potential peptide therapeutics", ADMET and DMPK, 2018, 6(2):162-175.
Van Eden et al., "Cloning of the mycobacterial epitope recognized by T lymphocytes in adjuvant arthritis", Nature, Jan. 14, 1988, 331(6152):171-173.
Van Glabbeke et al., "Progression-free rate as the principal endpoint for phase II trials in soft-tissue sarcomas", European Journal of Cancer, 2002, 38(4):543-549.
Vandenbroucke et al., "Is there new hope for therapeutic matrix metalloproteinase inhibition?", Nature reviews, Drug discovery, Dec. 2014, 13(12):904-927.
Villano, "Colorectal Cancer", Merck Manual, Retrieved from: https://www.merckmanuals.com/professional/gastrointestinal-disorders/tumors-of-the-gastrointestinal-tract/colorectal-cancer, Oct. 2023, pp. 1-8.
Wagstaff et al., "An Assay for Periplasm Entry Advances the Development of Chimeric Peptide Antibiotics", ACS Infectious Diseases, 2020, 6(9):2355-2361.
Wallack et al., "Abstract P05: Investigating soluble Nectin-4 and EphA2 as cancer biomarkers in plasma", Bio-IT World, May 23, 2023, pp. 1-6.
Walsh et al., "Abstract 5807: Bicycle Toxin Conjugates® for the treatment of solid tumors", American Association for Cancer Research Annual Meeting, Apr. 9, 2024, pp. 1-7.
Wang et al., "Co-expression of MMP-14 and MMP-19 predicts poor survival in human glioma", Clinical and Translational Oncology, 2013, 15:139-145.
Wang et al., "Comprehensive Surfaceome Profiling to Identify and Validate Novel Cell-Surface Targets in Osteosarcoma", Molecular Cancer Therapeutics, Jun. 2022, 21(6):903-913.
Wang et al., "Integrative surfaceome profiling identifies immunotherapeutic targets in osteosarcoma and preclinical testing of BT1769, an MT1-MMP-targeted Bicycle® toxin conjugate, in osteosarcoma by the Pediatric Preclinical Testing Consortium (PPTC)", AACR Annual Meeting, Apr. 10-15 and May 17-21, 2021, 15 pages.
Wang et al., "MMP-14 overexpression correlates with poor prognosis in non-small cell lung cancer", Tumor Biology, 2014, 35:9815-9821.
Watanabe et al., "NK cell dysfunction with down-regulated CD16 and up-regulated CD56 molecules in patients with esophageal squamous cell carcinoma", Diseases of the Esophagus, 2010, 23(8):675-681.
Waterhouse et al., "Safety profile of nivolumab administered as 30-min infusion: analysis of data from CheckMate 153", Cancer Chemotherapy and Pharmacology, 2018, 81(4):679-686.
Watts, "TNF/TNFR Family Members in Costimulation of T Cell Responses", Annual Review of Immunology, 2005, 23(1):23-68.
Weber, "Immune Checkpoint Proteins: A New Therapeutic Paradigm for Cancer-Preclinical Background: CTLA-4 and PD-1 Blockade", Seminars in Oncology, Oct. 2010, 37(5):430-439.
Wei et al., "Discovery of Peptidomimetic Antibody-Drug Conjugate Linkers with Enhanced Protease Specificity", Journal of Medicinal Chemistry, 2018, 61(3):989-1000.
Winter et al., "Making Antibodies by Phage Display Technology", Annual Review of Immunology, 1994, 12:433-455.
Wu et al., "A Novel Polymorphism of FegammaRIIIa (CD16) Alters Receptor Function and Predisposes to Autoimmune Disease", The Journal of Clinical Investigation, Sep. 1997, 100(5):1059-1070.
Wu et al., "Immunohistochemical localization of programmed death-1 ligand-1 (PD-L1) in gastric carcinoma and its clinical significance", Acta histochemica, 2006, 108(1):19-24.
Wu et al., "Natural killer cells in cancer biology and therapy", Molecular Cancer, 2020, 19(1):120, pp. 1-26.
Xu et al., "The application of PK/PD modelling in the clinical development of BT5528—a novel toxin delivery platform", ACoP, Oct. 30-Nov. 2, 2022, 21 pages.
Yampolsky et al., "The Exchangeability of Amino Acids in Proteins", Genetics, Aug. 2005, 170(4):1459-1472.
Yardley et al., "EMERGE: A Randomized Phase II Study of the Antibody-Drug Conjugate Glembatumumab Vedotin in Advanced Glycoprotein NMB-Expressing Breast Cancer", Journal of Clinical Oncology, May 10, 2015, 33(14):1609-1619.
Yoon et al., "An efficient strategy for cell-based antibody library selection using an integrated vector system", BMC Biotechnology, 2012, 12(62):1-10.
Yoshihara et al., "Tags for labeling protein N-termini with subtiligase for proteomics", Bioorganic & Medicinal Chemistry Letters, 2008, 18 (22):6000-6003.
Yu et al., "A New Strategy Applied to the Synthesis of an Alpha-Helical Bicyclic Peptide Constrained by Two Overlapping i, i+ 7 Side-Chain Bridges of Novel Design", Tetrahedron Letters, 1996, 37(11):1731-1734.
Yuan et al., "Advances in neuropilin-1 and its role as a therapeutic target in treatment of malignancies", Tumor, Mar. 2016, 36:358-364 (English Abstract Submitted).
Zarrabi et al., "Inhibition of Matrix Metalloproteinase 14 (MMP-14)-mediated Cancer Cell Migration", The Journal of Biological Chemistry, Sep. 23, 2011, 286(38):33167-33177.
Zervosen et al., "Development of New Drugs for an Old Target—The Penicillin Binding Proteins", Molecules, 2012, 17(11):12478-12505.

(56) References Cited

OTHER PUBLICATIONS

Zhang et al., "A new anti-HER2 antibody that enhances the anti-tumor efficacy of trastuzumab and pertuzumab with a distinct mechanism of action", Molecular Immunology, 2020, 119:48-58.
Zhang et al., "Characterization and application of three novel monoclonal antibodies against human 4-1BB: distinct epitopes of human 4-1BB on lung tumor cells and immune cells", Tissue Antigens, 2007, 70(6):470-479.
Zhang et al., "FCGR2A and FCGR3A Polymorphisms Associated With Clinical Outcome of Epidermal Growth Factor Receptor-Expressing Metastatic Colorectal Cancer Patients Treated With Single-Agent Cetuximab", Journal of Clinical Oncology, Aug. 20, 2007, 25(24):3712-3718.
Zhang et al., "Propagated Perturbations from a Peripheral Mutation Show Interactions Supporting WW Domain Thermostability", Structure, Nov. 6, 2018, 26(11):1474-1485.
Zhou et al., "Significance of semaphorin-3A and MMP-14 protein expression in non-small cell lung cancer", Oncology letters, 2014, 7(5):1395-1400.
Zhu et al., "High-Affinity Peptide Against MT1-MMP for In Vivo Tumor Imaging", Journal of Controlled Release, Mar. 30, 2011, 150(3):248-255.
Search Report received for PCT Patent Application No. PCT/EP2017/083953, dated May 9, 2018, 4 pages.
Search Report received for PCT Patent Application No. PCT/EP2017/083954, dated May 4, 2018, 4 pages.
Search Report received for PCT Patent Application No. PCT/EP2018/060498, dated Jul. 5, 2018, 6 pages.
Search Report received for PCT Patent Application No. PCT/EP2019/066010, dated Sep. 30, 2019, 5 pages.
Search Report received for PCT Patent Application No. PCT/EP2019/066066, dated Oct. 1, 2019, 5 pages.
Search Report received for PCT Patent Application No. PCT/EP2019/066273, dated Sep. 27, 2019, 5 pages.
Search Report received for PCT Patent Application No. PCT/EP2021/072866, dated Dec. 21, 2021, 7 pages.
Search Report received for PCT Patent Application No. PCT/GB2015/053247, dated Jan. 27, 2016, 5 pages.
Search Report received for PCT Patent Application No. PCT/GB2017/051250, dated Aug. 4, 2017, 5 pages.
Search Report received for PCT Patent Application No. PCT/GB2017/053560, dated Feb. 7, 2018, 4 pages.
Search Report received for PCT Patent Application No. PCT/GB2018/050017, dated Mar. 23, 2018, 5 pages.
Search Report received for PCT Patent Application No. PCT/GB2018/051118, dated Aug. 3, 2018, 8 pages.
Search Report received for PCT Patent Application No. PCT/GB2018/052222, dated Oct. 11, 2018, 4 pages.
Search Report received for PCT Patent Application No. PCT/GB2019/050485, dated Jun. 4, 2019, 6 Pages.
Search Report received for PCT Patent Application No. PCT/GB2019/050951, dated Jul. 4, 2019, 5 pages.
Search Report received for PCT Patent Application No. PCT/GB2019/051740, dated Aug. 29, 2019, 5 pages.
Search Report received for PCT Patent Application No. PCT/GB2019/051741, dated Aug. 5, 2019, 5 pages.
Search Report received for PCT Patent Application No. PCT/GB2019/053020, dated Jun. 23, 2020, 9 pages.
Search Report received for PCT Patent Application No. PCT/GB2019/053080, dated Feb. 7, 2020, 5 pages.
Search Report received for PCT Patent Application No. PCT/GB2019/053536, dated Mar. 11, 2020, 5 pages.
Search Report received for PCT Patent Application No. PCT/GB2019/053537, dated Mar. 11, 2020, 4 pages.
Search Report received for PCT Patent Application No. PCT/GB2019/053539, dated Mar. 11, 2020, 3 pages.
Search Report received for PCT Patent Application No. PCT/GB2019/053540, dated Mar. 11, 2020, 4 pages.
Search Report received for PCT Patent Application No. PCT/GB2019/053679, dated Mar. 11, 2020, 5 pages.
Search Report received for PCT Patent Application No. PCT/GB2019/053680, dated Mar. 11, 2020, 5 pages.
Search Report received for PCT Patent Application No. PCT/GB2020/050069, dated Apr. 15, 2020, 4 pages.
Search Report received for PCT Patent Application No. PCT/GB2020/050070, dated Jun. 23, 2020, 7 pages.
Search Report received for PCT Patent Application No. PCT/GB2020/050071, dated May 12, 2020, 5 pages.
Search Report received for PCT Patent Application No. PCT/GB2020/050072, dated Jun. 30, 2020, 7 pages.
Search Report received for PCT Patent Application No. PCT/GB2020/050073, dated Apr. 7, 2020, 5 pages.
Search Report received for PCT Patent Application No. PCT/GB2020/050074, dated Jun. 23, 2020, 8 pages.
Search Report received for PCT Patent Application No. PCT/GB2020/050505, dated Apr. 28, 2020, 4 pages.
Search Report received for PCT Patent Application No. PCT/GB2020/051140, dated Aug. 20, 2020, 4 pages.
Search Report received for PCT Patent Application No. PCT/GB2020/051144, dated Aug. 18, 2020, 5 pages.
Search Report received for PCT Patent Application No. PCT/GB2020/052058, dated Nov. 12, 2020, 5 pages.
Search Report received for PCT Patent Application No. PCT/GB2020/052590, dated Jan. 28, 2021, 4 pages.
Search Report received for PCT Patent Application No. PCT/GB2020/052619, dated Jan. 28, 2021, 4 pages.
Search Report received for PCT Patent Application No. PCT/GB2020/053026, dated Mar. 23, 2021, 4 pages.
Search Report received for PCT Patent Application No. PCT/GB2021/050490, dated May 19, 2021, 5 pages.
Search Report received for PCT Patent Application No. PCT/GB2021/050491, dated May 14, 2021, 6 pages.
Search Report received for PCT Patent Application No. PCT/GB2021/051220, dated Aug. 27, 2021, 6 pages.
Search Report received for PCT Patent Application No. PCT/GB2021/052001, dated Nov. 12, 2021, 4 pages.
Search Report received for PCT Patent Application No. PCT/GB2022/050043, dated Nov. 17, 2022, 6 pages.
Search Report received for PCT Patent Application No. PCT/GB2022/052249, dated Mar. 28, 2023, 6 pages.
Search Report received for PCT Patent Application No. PCT/GB2022/052903, dated Mar. 13, 2023, 4 pages.
U.S. Appl. No. 18/427,414, Beswick et al., filed Jan. 30, 2024.
U.S. Appl. No. 18/742,691, Chen, filed Jun. 13, 2024.
U.S. Appl. No. 18/906,616, Beswick et al., filed Oct. 4, 2024.
Bicycle Therapeutics, "Bicycle Therapeutics to Present New BT1718 Data in the "New Drugs on the Horizon" Session at the 2018 American Association for Cancer Research Meeting," Press Release. Apr. 3, 2018.
Loktev et al., "Multicyclic Peptides as Scaffolds for the Development of Tumor Targeting Agents," Current Medicinal Chemistry, 2017, vol. 24, pp. 2141-2155.
Morrison, "Chemical Strategies for Bicyclic Peptide Formation," Univ. of Leeds, Sep. 2015, pp. 1-60.
Mulder et al., "Scaffold Optimization in Discontinuous Epitope Containing Protein Mimics of gp120 Using Smart Libraries," Org. Biomol. Chem. 2013, vol. 11, pp. 2676-2684.
Pickens et al., "Practical Considerations, Challenges and Limitations of Bioconjugation via Azide-Alkyne Cycloaddition," Bioconjugate Chem., 2018, vol. 29, pp. 686-701.
Rhodes and Pei, "Bicyclic Peptides as Next-Generation Therapeutics," Chemistry. Sep. 18, 2017;23(52):12690-12703.
Smeenk et al., "Reconstructing the discontinuous and conformational (beta)1/(beta)3-loop binding site on hFSH/hCG by using highly constrained multicyclic peptides," Chembiochem. Jan. 2, 2015;16(1):91-9.
Upadhyaya, "Activation of CD137 Using Multivalent and Tumour Targeted Bicyclic Peptides," XP055669343, URL:https://www.bicycletherapeutics.com/wp-content/uploads/PU_2019-Peptide-Congress_publication.pdf, Peptide Congress, Apr. 25, 2019, 25 Pages.
PCT International Search Report and Written Opinion from PCT/GB2020/051827, dated Oct. 23, 2020.

(56) References Cited

OTHER PUBLICATIONS

Bennett et al., "Abstract 5855: Bicycle Drug Conjugates Targeting EphA2 for the Treatment of Solid Tumors: Discovery and Selection of BT5528," Cancer Res. 2018; 78 (13 suppl); 5855.
Annunziata et al., "Phase 1, open-label study of MEDI-547 in patients with relapsed or refractory solid tumors," Invest New Drugs. Feb. 2013;31(1):77-84.
Bennett et al., "Development of BT1718, a Bicycle Drug Conjugate® (BDC) targeting MT1-MMP for treatment of solid tumours," Eur J Cancer. Dec. 2016;69(suppl 1): S21(42;P013).
Bennett, "BT1718, a Bicycle Drug Conjugate (BTC): Profound Efficacy Without Bleeding and Coagulation Abnormalities in Animal Models," AACR Annual Meeting 2019. 4481.
Bennett et al., "Abstract 4481: BT5528, an EphA2-targeting Bicycle Toxin Conjugate (BTC): Profound efficacy without bleeding and coagulation abnormalities in animal models," Cancer Res. 2019; 79 (13 suppl); 4481.
Chen et al., "Peptide ligands stabilized by small molecules," Angew Chem Int Ed Engl. Feb. 3, 2014;53(6):1602-6.
Deonarain et al., "Small-Format Drug Conjugates: A Viable Alternative to ADCs for Solid Tumours?" Antibodies (Basel). 2018;7(2):16.
Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13 suppl):5144.
Mitra et al., "Structure-Activity Relationship Analysis of Peptides Targeting the EphA2 Receptor," Biochemistry. 2010;49(31):6687-95.
Mudd et al., "Identification and Optimization of EphA2-Selective Bicycles for the Delivery of Cytotoxic Payloads," J Med Chem. 2020;63(8):4107-16.
PCT International Search Report and Written Opinion from PCT/GB2018/053678, dated Mar. 11, 2019.
PCT International Search Report and Written Opinion from PCT/EP2019/065993, dated Sep. 13, 2019.
PCT International Search Report and Written Opinion from PCT/GB2020/051829, dated Oct. 21, 2020.
Shi et al., "One-Bead-Two-Compound Thioether Bridged Macrocyclic (gamma)-AApeptide Screening Library Against EphA2," J Med Chem. Nov. 22, 2017;60(22):9290-9298.
U.S. Appl. No. 16/771,186, filed Jun. 9, 2020.
U.S. Appl. No. 17/590,875, filed Feb. 2, 2022.
U.S. Appl. No. 17/592,966, filed Feb. 4, 2022.
U.S. Appl. No. 17/630,314, filed Jan. 26, 2022.
U.S. Appl. No. 17/630,747, filed Jan. 27, 2022.
U.S. Appl. No. 17/655,822, filed Mar. 22, 2022.
U.S. Appl. No. 17/663,169, filed May 12, 2022.
U.S. Appl. No. 17/779,226, filed May 24, 2022.
Wu et al., "Design and Characterization of Novel EphA2 Agonists for Targeted Delivery of Chemotherapy to Cancer Cells," Chem. Biol. 2015;22(7):876-887.
PCT International Search Report and Written Opinion from PCT/GB2018/053676, dated Mar. 21, 2019.
Adams, "Molecular control of arterial-venous blood vessel identity," J Anat. Jan. 2003;202(1):105-12.
Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.
Ausiello et al., "Functional topography of discrete domains of human CD38," Tissue Antigens. Dec. 2000;56(6):539-47.
Bennett et al., "Abstract 5854: BT5528, a Bicycle Toxin Conjugate targeting EphA2 has potent anti-tumor activity without bleeding or coagulation abnormalities in preclinical models." Cancer Res. 2018;78(13 suppl):5854.
Bennett et al., "BT5528, a Bicycle Toxin Conjugate targeting EphA2 has potent anti-tumor activity without bleeding or coagulation abnormalities in preclinical models," AACR Annual Meeting 2018.
Bennett et al., "MMAE Delivery Using the Bicycle Toxin Conjugate BT5528," Mol Cancer Ther. Jul. 2020; 19(7):1385-1394.
Berge et al., "Pharmaceutical salts," J Pharm Sci. 1977;66(1):1-19.
Binda et al., "The EphA2 receptor drives self-renewal and tumorigenicity in stem-like tumor-propagating cells from human glioblastomas," Cancer Cell. Dec. 11, 2012; 22(6);765-80.
Booth et al., "Crowd control in the crypt," Nat Med. Dec. 2002;8(12):1360-1.
Brannan et al., "EphA2 in the early pathogenesis and progression of non-small cell lung cancer," Cancer Prev Res (Phila). Dec. 2009;2(12):1039-49.
Brantley-Sieders et al., "Eph receptor tyrosine kinases in tumor and tumor microenvironment," Curr Pharm Des. 2004; 10(27); 3431-42.
Brantley-Sieders et al., "Eph/ephrin profiling in human breast cancer reveals significant associations between expression level and clinical outcome," PLoS One. 2011; 6(9): e24426.
Brantley-Sieders et al., "Impaired tumor microenvironment in EphA2-deficient mice inhibits tumor angiogenesis and metastatic progression," FASEB J. Nov. 2005; 19(13):1884-6.
Centers for Disease Control and Prevention, "What Can I Do to Reduce My Risk of Ovarian Cancer?" Division of Cancer Prevention and Control. Aug. 31, 2022.
Chan and Nie, "Quantum dot bioconjugates for ultrasensitive nonisotopic detection," Science. Sep. 25, 1998; 281 (5385): 2016-8.
Chang et al., "Five different anti-prostate-specific membrane antigen (PSMA) antibodies confirm PSMA expression in tumor-associated neovasculature," Cancer Res. Jul. 1, 1999; 59(13):3192-8.
Chen et al., "Structurally diverse cyclisation linkers impose different backbone conformations in bicyclic peptides," Chembiochem. May 7, 2012; 13(7): 1032-8.
Cheng et al., "Blockade of EphA receptor tyrosine kinase activation inhibits vascular endothelial cell growth factor-induced angiogenesis," Mol Cancer Res. Nov. 2002; 1(1): 2-11.
Cherney et al., "Macrocyclic amino carboxylates as selective MMP-8 inhibitors," J Med Chem. May 21, 1998;41(11):1749-51.
Chiche et al., "Hypoxia-inducible carbonic anhydrase IX and XII promote tumor cell growth by counteracting acidosis through the regulation of the intracellular pH," Cancer Res. Jan. 1, 2009;69(1):358-68.
Dagher et al., "c-Kit and CD38 are expressed by long-term reconstituting hematopoietic cells present in the murine yolk sac," Biol Blood Marrow Transplant. 1998;4(2):69-74.
Deaglio et al., "CD38 is a signaling molecule in B-cell chronic lymphocytic leukemia cells," Blood. Sep. 15, 2003;102(6):2146-55.
Deyle et al., "Phage Selection of Cyclic Peptides for Application in Research and Drug Development." Acc Chem Res. 2017;50(8):1866-1874.
Di, "Strategic approaches to optimizing peptide ADME properties," AAPS J. Jan. 2015;17(1):134-43.
Driggers et al., "The exploration of macrocycles for drug discovery—an underexploited structural class," Nat Rev Drug Discov. Jul. 2008;7(7):608-24.
Dunne et al., "EphA2 Expression Is a Key Driver of Migration and Invasion and a Poor Prognostic Marker in Colorectal Cancer," Clin Cancer Res. Jan. 1, 2016;22(1):230-242.
Duong and Rodan, "The role of integrins in osteoclast function," J Bone Miner Metab. 1999; 17(1):1-6.
Funaro et al., "Human CD38 is associated to distinct molecules which mediate transmembrane signaling in different lineages," Eur J Immunol. Oct. 1993;23(10):2407-11.
Funaro et al., "Involvement of the multilineage CD38 molecule in a unique pathway of cell activation and proliferation," J Immunol. Oct. 15, 1990;145(8):2390-6.
Gandhi et al., "MP69-11 Carbonic Anhydrase IX Assay: A Paradigm Shift in Diagnosis of Malignant Cystic Renal Lesions," J Urol. May 18, 2015;193(4S):e870-e871.
Guo et al., "Prognostic significance of combinations of RNA-dependent protein kinase and EphA2 biomarkers for NSCLC," J Thorac Oncol. Mar. 2013;8(3):301-8.
Heinis et al., "Phage-encoded combinatorial chemical libraries based on bicyclic peptides," Nat. Chem. Biol. 2009;5(7):502-7.

(56) References Cited

OTHER PUBLICATIONS

Hess et al., "Molecular regulation of tumor cell vasculogenic mimicry by tyrosine phosphorylation: role of epithelial cell kinase (Eck/EphA2)," Cancer Res. Apr. 15, 2001;61(8):3250-5.
Hoshino et al., "Mapping of the catalytic and epitopic sites of human CD38/NAD+ glycohydrolase to a functional domain in the carboxyl terminus," J Immunol. Jan. 15, 1997;158(2):741-7.
PCT International Search Report and Written Opinion from PCT/GB2018/051779, dated Aug. 23, 2018.
Jackson et al., "A human antibody-drug conjugate targeting EphA2 inhibits tumor growth in vivo," Cancer Res. Nov. 15, 2008;68(22):9367-74.
Jin et al., "(alpha)V(beta)3 Integrin-Targeted Radionuclide Therapy with 64Cu-cyclam-RAFT-c(-RGDfK-)4," Mol Cancer Ther. Sep. 2016;15(9):2076-85.
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," J Org Chem. 1985;50(26):5834-8.
Kinch et al., "Predictive value of the EphA2 receptor tyrosine kinase in lung cancer recurrence and survival," Clin Cancer Res. Feb. 2003;9(2):613-8.
Kitanaka et al., "CD38 ligation in human B cell progenitors triggers tyrosine phosphorylation of CD19 and association of CD19 with lyn and phosphatidylinositol 3-kinase," J Immunol. Jul. 1, 1997;159(1):184-92.
Kitanaka et al., "CD38-mediated signaling events in murine pro-B cells expressing human CD38 with or without its cytoplasmic domain," J Immunol. Feb. 15, 1999;162(4):1952-8.
Konopleva et al., "Ligation of cell surface CD38 protein with agonistic monoclonal antibody induces a cell growth signal in myeloid leukemia cells," J Immunol. Nov. 1, 1998;161(9):4702-8.
Kumagai et al., "Ligation of CD38 suppresses human B lymphopoiesis," J Exp Med. Mar. 1, 1995;181(3):1101-10.
Lee et al., "ADP-ribosyl cyclase and CD38. Multi-functional enzymes in Ca+2 signaling," Adv Exp Med Biol. 1997;419:411-9.
Lee and Aarhus, "ADP-ribosyl cyclase: an enzyme that cyclizes NAD+ into a calcium-mobilizing metabolite," Cell Regul. Mar. 1991;2(3):203-9.
Lee et al., "Structural determination of a cyclic metabolite of NAD+ with intracellular Ca2+-mobilizing activity," J Biol Chem. Jan. 25, 1989;264(3):1608-15.
Li et al., "Up-regulation of EphA2 and down-regulation of EphrinA1 are associated with the aggressive phenotype and poor prognosis of malignant glioma," Tumour Biol. Oct. 2010;31(5):477-88.
Lin et al., "EphA2 overexpression is associated with angiogenesis in ovarian cancer," Cancer. Jan. 15, 2007;109(2):332-40.
Lund et al., "CD38 signaling in B lymphocytes is controlled by its ectodomain but occurs independently of enzymatically generated ADP-ribose or cyclic ADP-ribose," J Immunol. Mar. 1, 1999;162(5):2693-702.
Mallone et al., "Signaling through CD38 induces NK cell activation," Int Immunol. Apr. 1, 2001;13(4):397-409.
Marmé, "VEGFs, angiopoietins, Ephrins and their receptors: putative targets for tumor therapy?" Ann Hematol. 2002;81 Suppl 2:S66.
Merritt et al., "Analysis of EphA2 expression and mutant p53 in ovarian carcinoma," Cancer Biol Ther. Oct. 2006; 5(10):1357-60.
Morra et al., "CD38 is functionally dependent on the TCR/CD3 complex in human T cells," FASEB J. May 1998;12(7):581-92.
Mudali et al., "Patterns of EphA2 protein expression in primary and metastatic pancreatic carcinoma and correlation with genetic status," Clin Exp Metastasis. 2006;23(7-8):357-65.
BicycleTx Limited, "Study BT5528-100 in Patients With Advanced Solid Tumors Associated With EphA2 Expression," ClinicalTrials.gov Identifier NCT04180371. First Posted Nov. 27, 2019; Accessed Dec. 3, 20220: https://clinicaltrials.gov/ct2/show/NCT04180371.
Nakamoto and Bergemann, "Diverse roles for the Eph family of receptor tyrosine kinases in carcinogenesis," Microsc Res Tech. Oct. 1, 2002;59(1):58-67.
Nakamura et al., "EPHA2/EFNA1 expression in human gastric cancer," Cancer Sci. Jan. 2005;96(1):42-7.
Nakamura et al., "Involvement of alpha(v)beta3 integrins in osteoclast function," J Bone Miner Metab. 2007;25(6):337-44.
Nan et al., "Dual function glutamate-related ligands: discovery of a novel, potent inhibitor of glutamate carboxypeptidase II possessing mGluR3 agonist activity," J Med Chem. Mar. 9, 2000;43(5):772-4.
Neri and Supuran, "Interfering with pH regulation in tumours as a therapeutic strategy," Nat Rev Drug Discov. Sep. 16, 2011;10(10):767-77.
Oliver et al., "Mouse CD38 is down-regulated on germinal center B cells and mature plasma cells," J Immunol. Feb. 1, 1997;158(3):1108-15.
Partida-Sánchez et al., "Cyclic ADP-ribose production by CD38 regulates intracellular calcium release, extracellular calcium influx and chemotaxis in neutrophils and is required for bacterial clearance in vivo," Nat Med. Nov. 2001;7(11):1209-16.
Partida-Sánchez et al., "Regulation of dendritic cell trafficking by the ADP-ribosyl cyclase CD38: impact on the development of humoral immunity," Immunity. Mar. 2004;20(3):279-91.
PCT International Search Report and Written Opinion from PCT/GB2020/050874 dated Jun. 17, 2020.
PCT International Search Report and Written Opinion from PCT/GB2021/051451, dated Sep. 22, 2021.
Pietraszek et al., "Lumican: a new inhibitor of matrix metalloproteinase-14 activity," FEBS Lett. Nov. 28, 2014;588(23):4319-24.
Poliakov et al., "Diverse roles of eph receptors and ephrins in the regulation of cell migration and tissue assembly," Dev Cell. Oct. 2004;7(4):465-80.
Ramirez et al., "Defining causative factors contributing in the activation of hedgehog signaling in diffuse large B-cell lymphoma," Leuk Res. Oct. 2012;36(10):1267-73.
Randall et al., "Expression of murine CD38 defines a population of long-term reconstituting hematopoietic stem cells," Blood. May 15, 1996;87(10):4057-67.
Remacle et al., "Novel MT1-MMP small-molecule inhibitors based on insights into hemopexin domain function in tumor growth," Cancer Res. May 1, 2012;72(9):2339-49.
Ridderstad and Tarlinton, "Kinetics of establishing the memory B cell population as revealed by CD38 expression," J Immunol. May 15, 1998;160(10):4688-95.
Rodan and Rodan, "Integrin function in osteoclasts," J Endocrinol. Sep. 1997;154 Suppl:S47-56.
Ross and Christiano, "Nothing but skin and bone," J Clin Invest. May 2006;116(5):1140-9.
Rostovtsev et al., "A stepwise huisgen cycloaddition process: copper(I)-catalyzed regioselective "ligation" of azides and terminal alkynes," Angew Chem Int Ed Engl. Jul. 15, 2002;41(14):2596-9.
Schülke et al., "The homodimer of prostate-specific membrane antigen is a functional target for cancer therapy," Proc Natl Acad Sci U S A. Oct. 28, 2003;100(22):12590-5.
Sounni et al., "MT1-MMP expression promotes tumor growth and angiogenesis through an up-regulation of vascular endothelial growth factor expression," FASEB J. Apr. 2002;16(6):555-64.
Stein et al., "Eph receptors discriminate specific ligand oligomers to determine alternative signaling complexes, attachment, and assembly responses," Genes Dev. Mar. 1, 1998;12(5):667-678.
Stevenson et al., "Preliminary studies for an immunotherapeutic approach to the treatment of human myeloma using chimeric anti-CD38 antibody," Blood. Mar. 1, 1991;77(5):1071-9.
Sun et al., "Carbohydrate and protein immobilization onto solid surfaces by sequential Diels-Alder and azide-alkyne cycloadditions," Bioconjug Chem. Jan.-Feb. 2006;17(1):52-7.
Supuran, "Carbonic anhydrases: novel therapeutic applications for inhibitors and activators," Nat Rev Drug Discov. Feb. 2008;7(2):168-81.
Tandon et al., "Emerging strategies for EphA2 receptor targeting for cancer therapeutics." Expert Opin Ther Targets. 2011;15(1):31-51.
Tasch et al., "A unique folate hydrolase, prostate-specific membrane antigen (PSMA): a target for immunotherapy?" Crit Rev Immunol. 2001;21(1-3):249-61.
Teitelbaum, "Osteoclasts, integrins, and osteoporosis," J Bone Miner Metab. Oct. 2000;18(6):344-9.

(56) References Cited

OTHER PUBLICATIONS

Teitelbaum, "Osteoporosis and Integrins," J Clin Endocrinol Metab. Apr. 2005;90(4):2466-8.
Teti et al., "The role of the alphaVbeta3 integrin in the development of osteolytic bone metastases: a pharmacological target for alternative therapy?" Calcif Tissue Int. Oct. 2002;71(4):293-9.
Teufel et al., "Backbone-driven collapse in unfolded protein chains," J Mol Biol. Jun. 3, 2011;409(2):250-62.
Timmerman et al., "Rapid and quantitative cyclization of multiple peptide loops onto synthetic scaffolds for structural mimicry of protein surfaces," Chembiochem. May 2005;6(5):821-4.
Todisco et al., "CD38 ligation inhibits normal and leukemic myelopoiesis," Blood. Jan. 15, 2000;95(2):535-42.
Uckun, "Regulation of human B-cell ontogeny," Blood. Nov. 15, 1990;76(10):1908-23.
Walker-Daniels et al., "Overexpression of the EphA2 tyrosine kinase in prostate cancer," Prostate. Dec. 1, 1999;41(4):275-80.
Wallbrecher et al., "Exploration of the design principles of a cell-penetrating bicylic peptide scaffold," Bioconjug Chem. May 21, 2014;25(5):955-64.
Wang et al., "Probing for integrin alpha v beta3 binding of RGD peptides using fluorescence polarization," Bioconjug Chem. May-Jun. 2005;16(3):729-34.
Wang, "An exact mathematical expression for describing competitive binding of two different ligands to a protein molecule," FEBS Lett. Feb. 27, 1995;360(2):111-4.
Wind et al., "Measuring carbonic anhydrase IX as a hypoxia biomarker: differences in concentrations in serum and plasma using a commercial enzyme-linked immunosorbent assay due to influences of metal ions," Ann Clin Biochem. Mar. 2011;48(Pt 2):112-20.
Wu et al., "Structures of the CXCR4 chemokine GPCR with small-molecule and cyclic peptide antagonists," Science. Nov. 19, 2010;330(6007):1066-71.
Wykosky et al., "EphA2 as a novel molecular marker and target in glioblastoma multiforme," Mol Cancer Res. Oct. 2005;3(10):541-51.
Xiong et al., "Crystal structure of the extracellular segment of integrin alpha Vbeta3 in complex with an Arg-Gly-Asp ligand," Science. Apr. 5, 2002;296(5565):151-5.
Yang et al., "Overexpression of EphA2, MMP-9, and MVD-CD34 in hepatocellular carcinoma: Implications for tumor progression and prognosis," Hepatol Res. Dec. 2009;39(12):1169-77.
Yuan et al., "Over-expression of EphA2 and EphrinA-1 in human gastric adenocarcinoma and its prognostic value for postoperative patients," Dig Dis Sci. Nov. 2009;54(11):2410-7.
Zelinski et al., "EphA2 overexpression causes tumorigenesis of mammary epithelial cells," Cancer Res. Mar. 1, 2001;61(5):2301-6.
Zhao et al., "Structural basis of specificity of a peptidyl urokinase inhibitor, upain-1," J Struct Biol. Oct. 2007; 160(1):1-10.
Zhuang et al., "Elevation of receptor tyrosine kinase EphA2 mediates resistance to trastuzumab therapy," Cancer Res. Jan. 1, 2010;70(1):299-308.
Zilber et al., "CD38 expressed on human monocytes: a coaccessory molecule in the superantigen-induced proliferation," Proc Natl Acad Sci U S A. Mar. 14, 2000;97(6):2840-5.
Zubiaur et al., "CD38 ligation results in activation of the Raf-1/mitogen-activated protein kinase and the CD3-zeta/zeta-associated protein-70 signaling pathways in Jurkat T lymphocytes," J Immunol. Jul. 1, 1997;159(1):193-205.
Zupo et al., "CD38 signaling by agonistic monoclonal antibody prevents apoptosis of human germinal center B cells," Eur J Immunol. May 1994;24(5):1218-22.
U.S. Appl. No. 18/313,983, filed May 8, 2023.
U.S. Appl. No. 18/345,506, filed Jun. 30, 2023.
PCT International Search Report and Written Opinion from PCT/GB2020/051923, dated Feb. 18, 2021.
Hurov et al., "T7480, a novel fully synthetic tumor-targeted immune cell agonist (TICA(TM)) induces tumor localized CD137 agonism" 2020 URL: https://www.bicycletherapeutics.com/wp-content/uploads/2020-06-16-BT7480-AACR-2020-poster-P5552_Final_CD137-in-title-002.pdf.
PCT International Search Report and Written Opinion from PCT/GB2020/051831, dated Feb. 4, 2021.
Anonymous, "Constrained peptides Unconstrained thinking Forward-looking statements", Aug. 1, 2019 (Aug. 1, 2019), p. 1-30, URL:https://investors.bicycletherapeutics.com/static-files/1e4832c5-1181-4fcc-acd9-c1dbb1c8b594.
Beswick, "Bicycles—An entirely new class of therapeutics," 2019; URL:https://www.bicycletherapeutics.com/wp-content/uploads/RSC-02-May-2019.pdf.
PCT International Search Report and Written Opinion from PCT/GB2020/052445, dated Apr. 4, 2021.
U.S. Appl. No. 18/271,360, filed Jul. 7, 2023.
Dufort et al, "789: Generation of a Bicycle NK-TICA(TM), a novel NK cell engaging molecule to enhance targeted tumor cytotoxicity", Nov. 10, 2021 (Nov. 10, 2021), vol. 9, No. Suppl 2, page; URL:https://jitc.bmj.com/content/jitc/9/Suppl_2/A824.full.pdf.
PCT International Search Report and Written Opinion from PCT/GB2022/050044, dated Jul. 14, 2022.
U.S. Appl. No. 18/271,593, filed Jul. 10, 2023.
PCT International Search Report and Written Opinion from PCT/GB2022/050055, dated Jul. 14, 2022.
Anonymous, "Bicycle Conjugates," 2021; URL:https://web.archive.org/web/20210104063050/https://www.bicycletherapeutics.com/programs/.
Anonymous, "Bicycle Therapeutics to Present New Translational Research for BT5528 and Preclinical Data for Tumor-targeted Immune Cell Agonists at the AACR Virtual Annual Meeting II," 2020; URL:https://www.businesswire.com/news/home/20200515005111/en/Bicycle-Therapeutics-to-Present-New-Translational-Research-for-BT5528-and-Preclinical-Data-for-Tumor-targeted-Immune-Cell-Agonists-at-the-AACR-Virtual-Annual-Meeting-II.
Sporn et al., "Chemoprevention of Cancer," Carcinogenesis; 2000;21:525-530.
Zugazagoitia et al., "Current Challenges in Cancer Treatment," Clinical Therapies; 2016;38:1551-1566.
Johnson et al., "Melanoma-specific MHC-II expression represents a tumour-autonomous phenotype and predicts response to anti-PD-1/PD-L1 therapy," Nat Commun. 2016.
Medical news Today, What are the most curable cancers? 2020.
Merck Manual consumer version, Cancer treatment principles, Jul. 2018.
Merck Manual consumer version, Overview of Cancer therapy, Jul. 2018.
National Cancer Institute (https://www.cancer.gov/about-cancer/understanding/what-is-cancer National cancer institute, What is Cancer? 2015.
Nishiwada et al., "Nectin-4 Expression Contributes to Tumor Proliferation, Angiogenesis and Patient Prognosis in Human Pancreatic Cancer," Journal of Experimental & Clinical Cancer Research, Biomed Central LTD. 2015;34:30.
Sausville and Burger, "Contributions of Human Tumor Xenografts to Anticancer Drug Development," Cancer Res. 2006;66(7): 3351-3354.

C

FIGURE 2 (ctd)

| Compound | Terminal half-life, $T_{1/2}$(h) |
|---|---|
| BCY11863 | 2.5 |

A

B

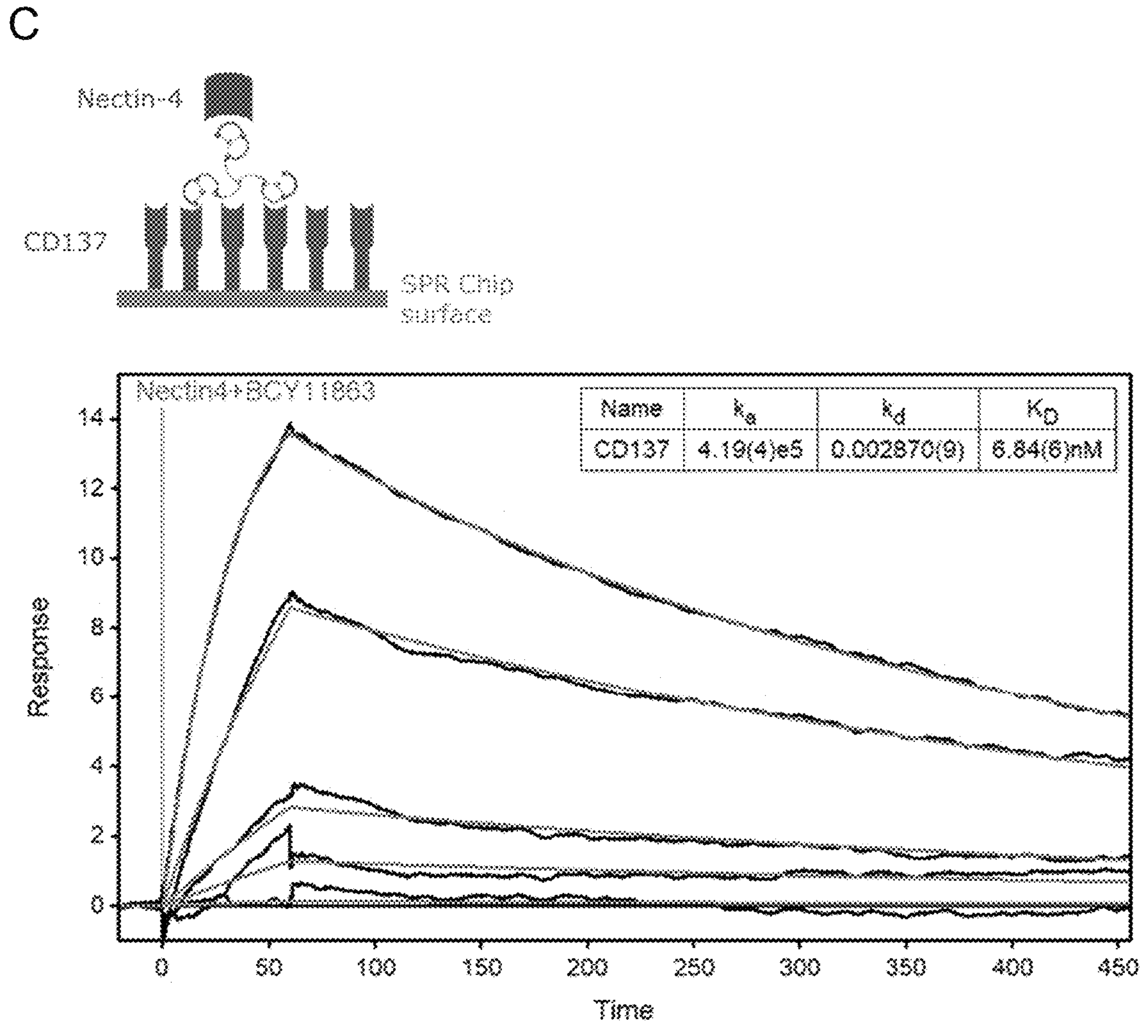
FIGURE 10 (ctd)

D
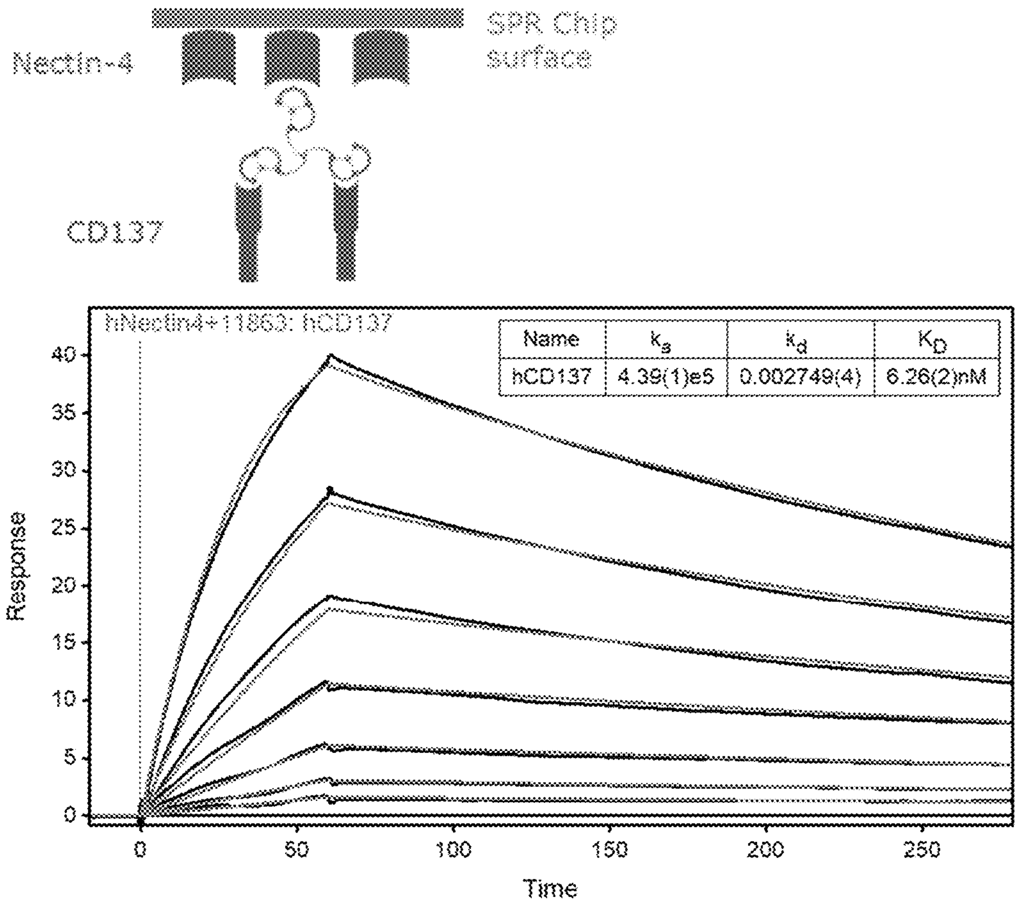
E
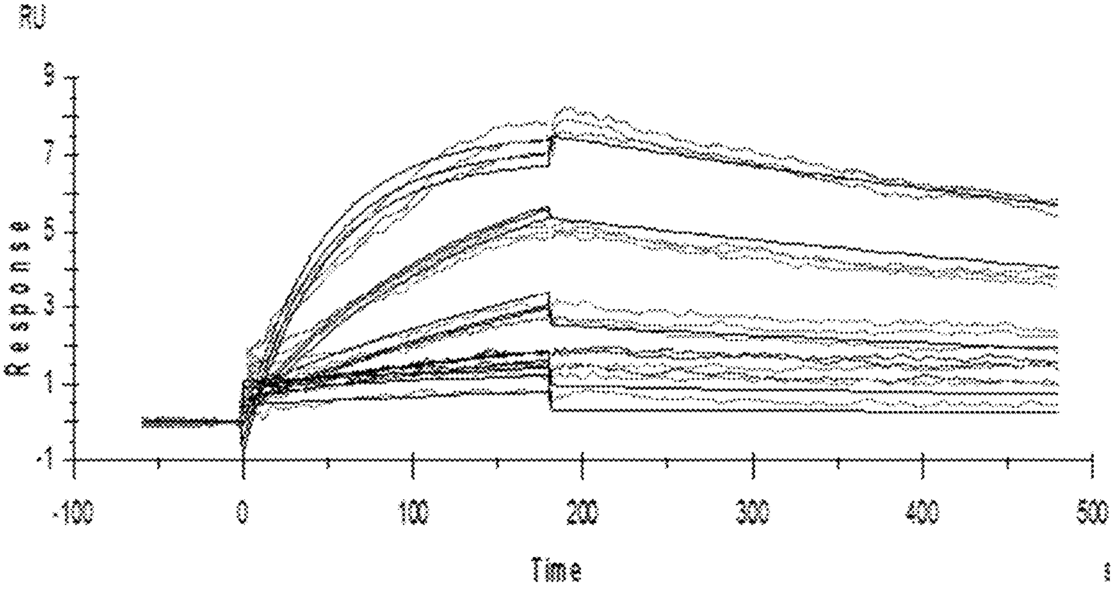
FIGURE 10 (ctd)

HETEROTANDEM BICYCLIC PEPTIDE COMPLEX

CROSS-REFERENCE TO RELATED APPLICATIONS

This application is a continuation application of U.S. patent application Ser. No. 17/592,966 filed on Feb. 4, 2022, which is a continuation application of U.S. patent application Ser. No. 16/941,614, filed on Jul. 29, 2020 which claims priority to U.S. Provisional Application No. 63/024,715, filed May 14, 2020; U.S. Provisional Application No. 63/022,667, filed May 11, 2020; U.S. Provisional Application No. 62/931,442, filed Nov. 6, 2019; U.S. Provisional Application No. 62/910,088, filed Oct. 3, 2019; and US Provisional Application No. 62/880,191, filed Jul. 30, 2019, each of which is incorporated herein by reference in its entirety.

SEQUENCE LISTING

The instant application contains a Sequence Listing which has been submitted electronically in XML format and is hereby incorporated by reference in its entirety. Said XML copy, created on Jun. 9, 2024, is named 392664037USC3.xml and is 19,990 bytes in size.

FIELD OF THE INVENTION

The present invention relates to a heterotandem bicyclic peptide complex which comprises a first peptide ligand, which binds to Nectin-4, conjugated via a linker to two second peptide ligands, which bind to CD137. The invention also relates to the use of said heterotandem bicyclic peptide complex in preventing, suppressing or treating cancer.

BACKGROUND OF THE INVENTION

Cyclic peptides can bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris (bromomethyl) benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example 1,1',1"-(1,3,5-triazinane-1,3,5-triyl)triprop-2-en-1-one (TATA) are disclosed in WO 2019/122860 and WO 2019/122863.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-$(Xaa)_6$-Cys-$(Xaa)_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a heterotandem bicyclic peptide complex comprising:

(a) a first peptide ligand which binds to Nectin-4 and which has the sequence $C_i$P[1Nal][dD]$C_{ii}$M[HArg]DWSTP[HyP]W$C_{iii}$ (SEQ ID NO: 1; BCY8116); conjugated via an N-(acid-PEG$_3$)-N-bis(PEG$_3$-azide) linker to (b) two second peptide ligands which bind to CD137 both of which have the sequence Ac-$C_i$[tBuAla]PE[D-Lys(PYA)]PY$C_{ii}$FADPY[Nle]$C_{iii}$-A (SEQ ID NO: 2; BCY8928);

wherein each of said peptide ligands comprise a polypeptide comprising three reactive cysteine groups ($C_i$, $C_{ii}$ and $C_{iii}$), separated by two loop sequences, and a molecular scaffold which is 1,1',1"-(1,3,5-triazinane-1,3,5-triyl)triprop-2-en-1-one (TATA) and which forms covalent bonds with the reactive cysteine groups of the polypeptide such that two polypeptide loops are formed on the molecular scaffold;

wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

According to a further aspect of the invention, there is provided a pharmaceutical composition comprising a heterotandem bicyclic peptide complex as defined herein in combination with one or more pharmaceutically acceptable excipients.

According to a further aspect of the invention, there is provided a heterotandem bicyclic peptide complex as defined herein for use in preventing, suppressing or treating cancer.

Figure 2:
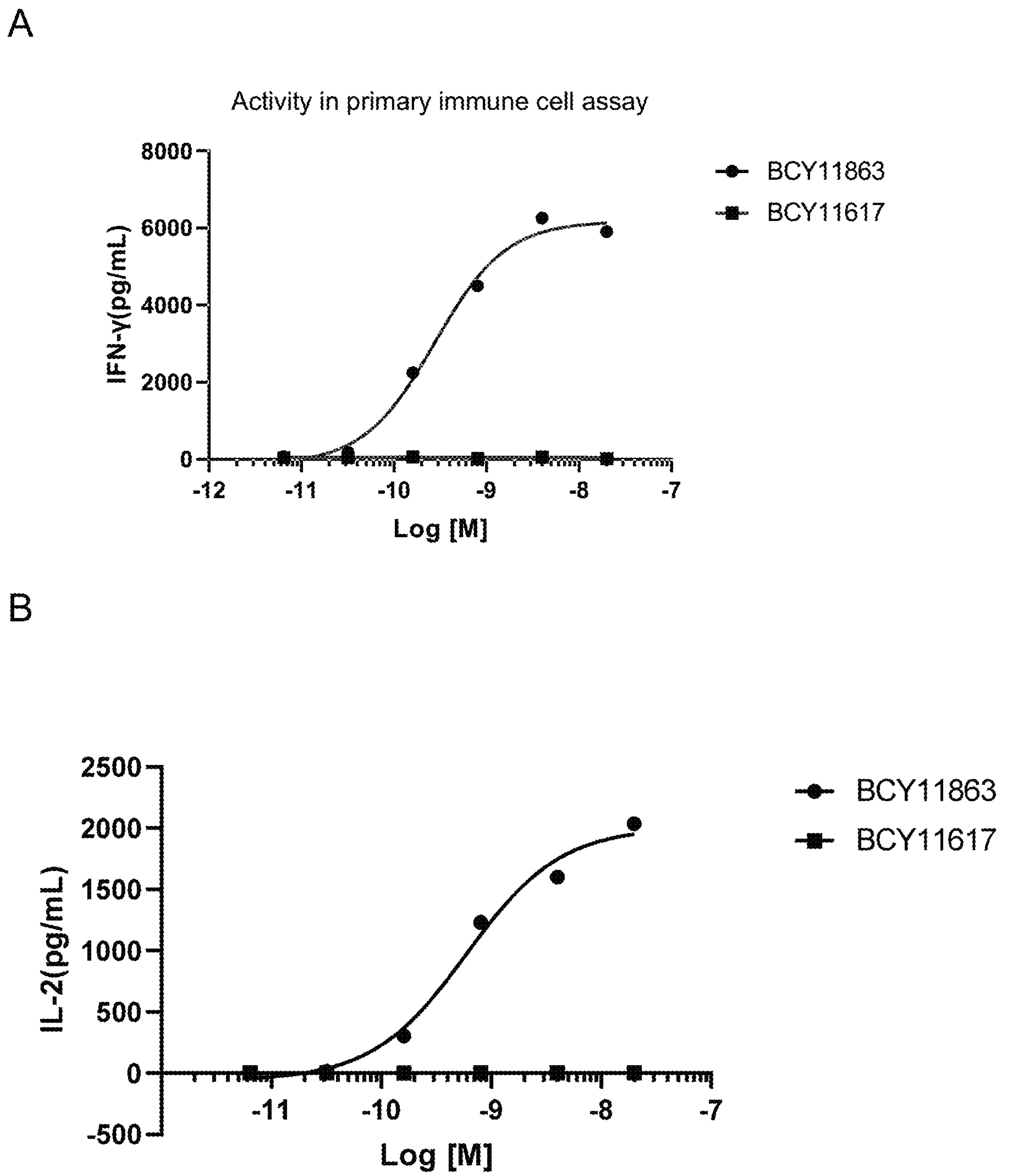

FIG. 2: Nectin-4/ CD137 heterotandem bicyclic peptide complexes induce IFN-γ (FIG. 2A) and IL-2 (FIG. 2B) cytokine secretion in a PBMC-4T1 co-culture assay. 4T1 cells were engineered to express Nectin-4. BCY11617 is a heterotandem bicyclic peptide complex that binds to Nectin-4 with the same affinity as BCY11863 but does not bind to CD137. FIG. 2C represents a summary of EC50 (nM) of BCY11863 in the cytokine secretion assay with multiple human PBMC donors and tumor cell lines.

Figure 3:
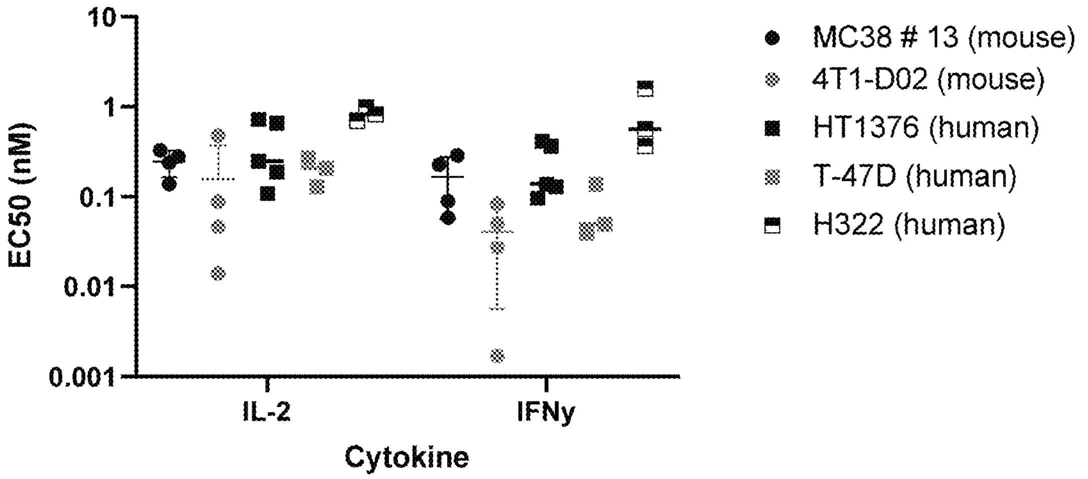
Figure 3:
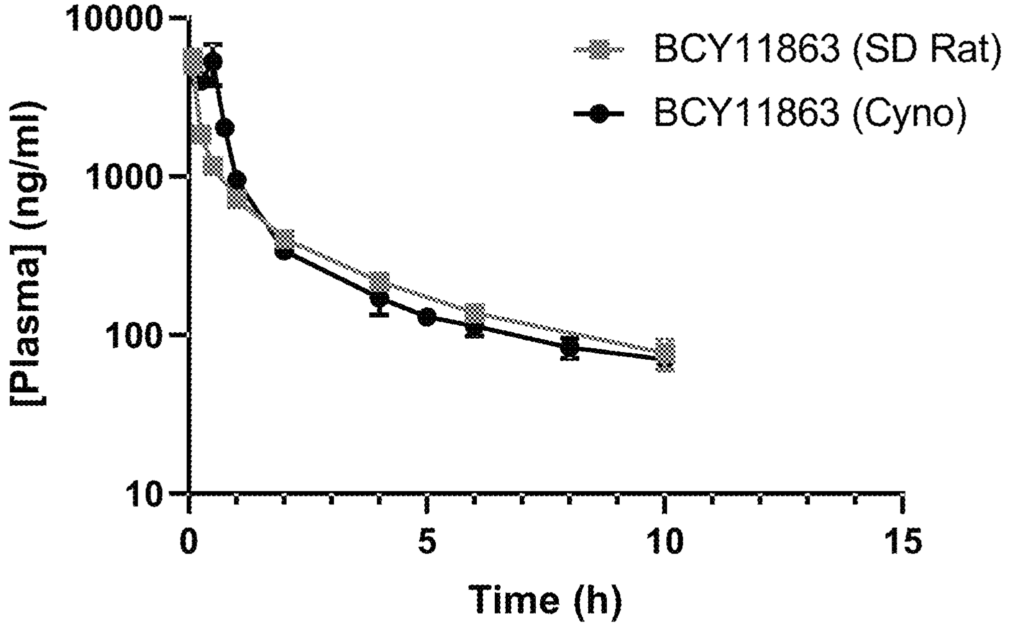

FIG. 3: Pharmacokinetics of heterotandem bicyclic peptide complex BCY11863 in SD Rats and Cynomolgus monkey (cyno) dosed IV at 2 mg/kg (n=3) and 1 mg/kg (n=2) respectively.

Figure 4:
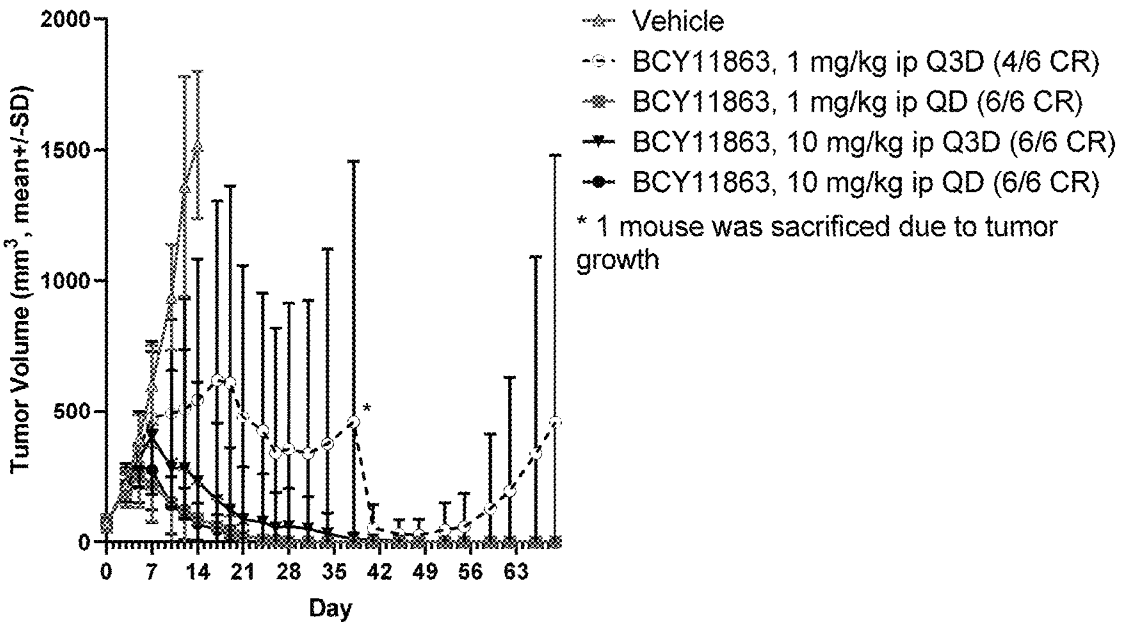

FIG. 4: Anti-tumor activity of BCY11863 in a syngeneic mouse Nectin-4 overexpressing MC38 tumor model (MC38#13). Tumor volumes during and after BCY11863 treatment. Number of complete responder (CR) mice on D69 are indicated in parentheses. QD: daily dosing; Q3D: every three days dosing; ip: intraperitoneal administration.

Figure 5:
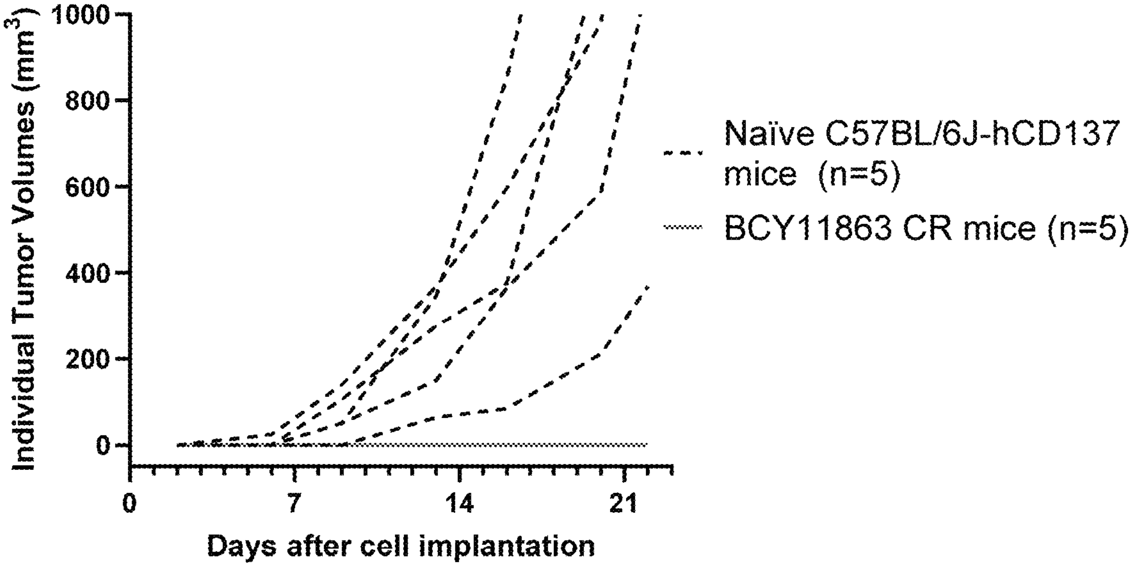

FIG. 5: BCY11863 treatment leads to an immunogenic memory to Nectin-4 overexpressing MC38 tumor cells (MC38#13). Tumor volumes are shown after inoculation to naïve C57BL/6J-hCD137 mice or mice that had complete responses (CR) to BCY11863. Note that none of the CR mice developed tumors by the end of the observation period (22 days).

Figure 6:
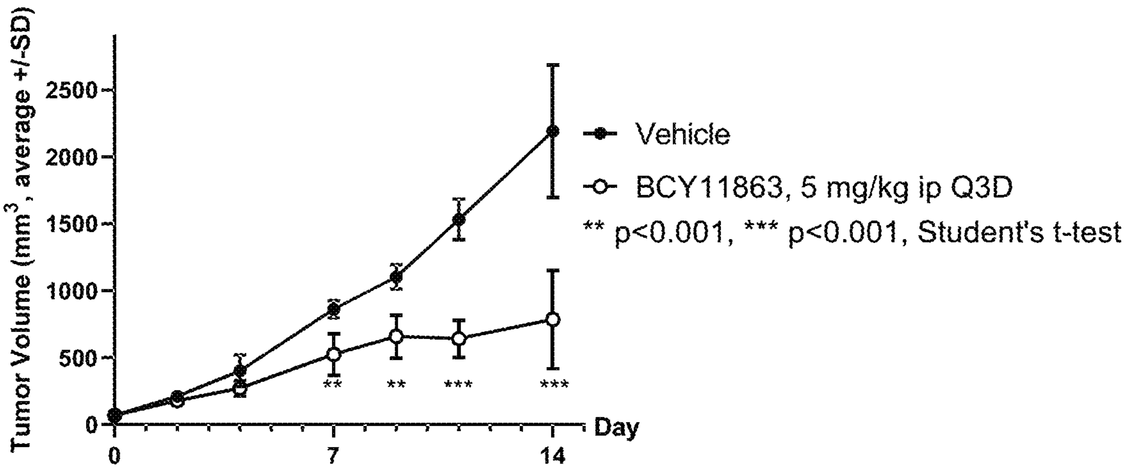

FIG. 6: BCY11863 demonstrates anti-tumor activity in a mouse syngeneic Nectin-4 overexpressing CT26 tumor model (CT26#7). Tumor volumes during BCY11863 treatment. Q3D: every three days dosing; ip: intraperitoneal administration.

Figure 7:
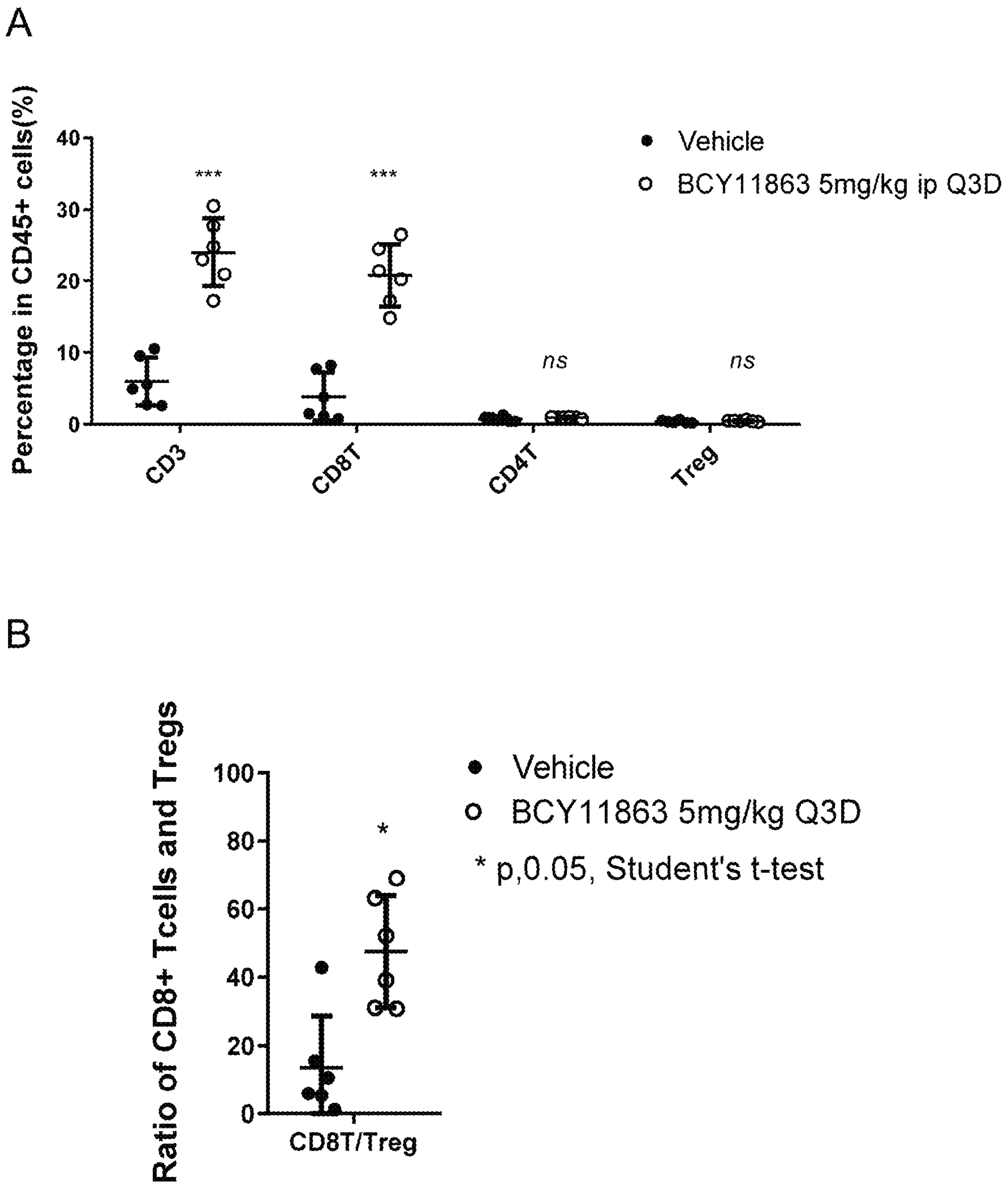

FIG. 7: Total T cells and CD8+ T cells increase in CT26#7 tumor tissue 1 h after the last (6th) Q3D dose of BCY11863. Analysis of (A) total T cells, CD8+ T cells, CD4+ T cells, Tregs and (B) CD8+ T cell/Treg-ratio in CT26#7 tumor tissue 1 h after last Q3D dose of BCY11863.

Figure 8:
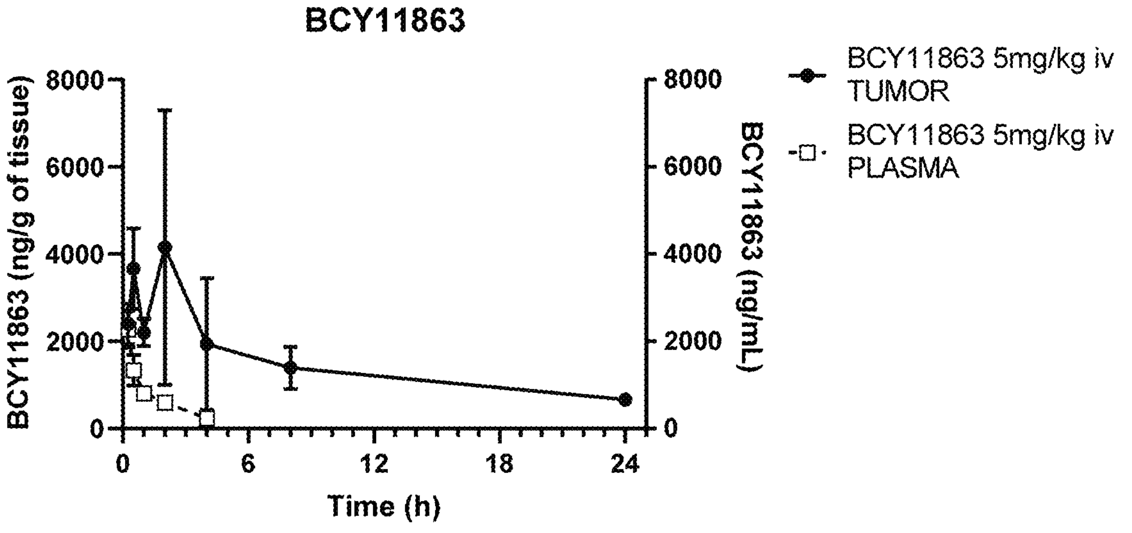

FIG. 8: Pharmacokinetic profiles of BCY11863 in plasma and tumor tissue of CT26#7 syngeneic tumor bearing animals after a single intravenous (iv) administration of 5 mg/kg of BCY11863.

Figure 9:
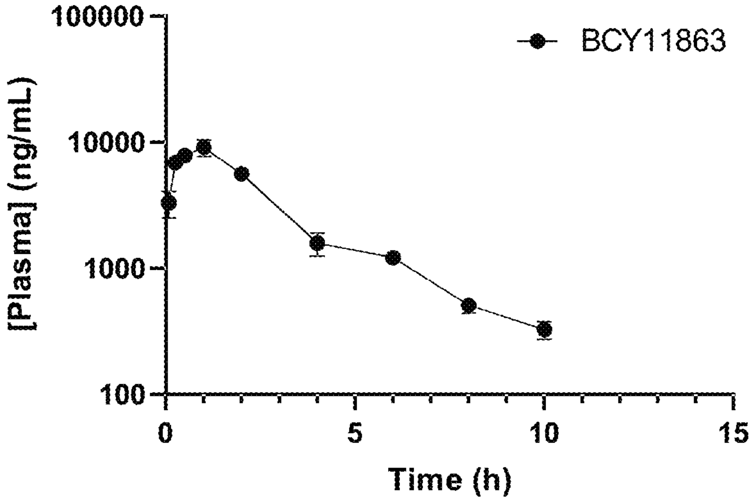

FIG. 9: Plasma concentration vs time curve of BCY11863 from a 15 mg/kg intraperitoneal dose in CD-1 mice (n=3) and the terminal plasma half life for BCY11863.

Figure 10:
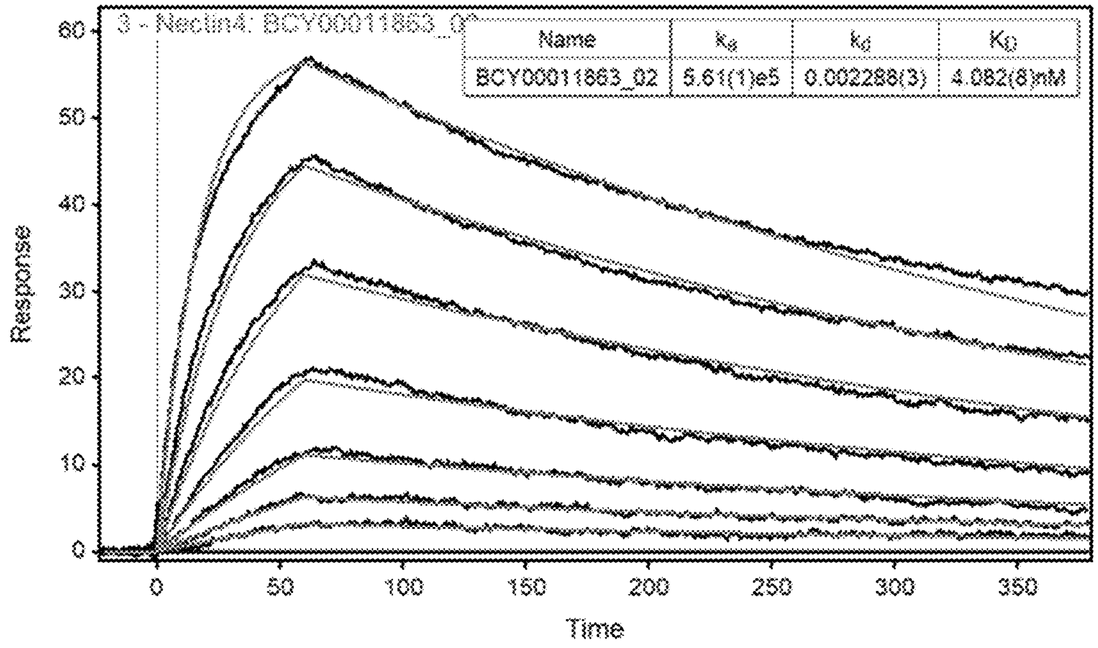
Figure 10:
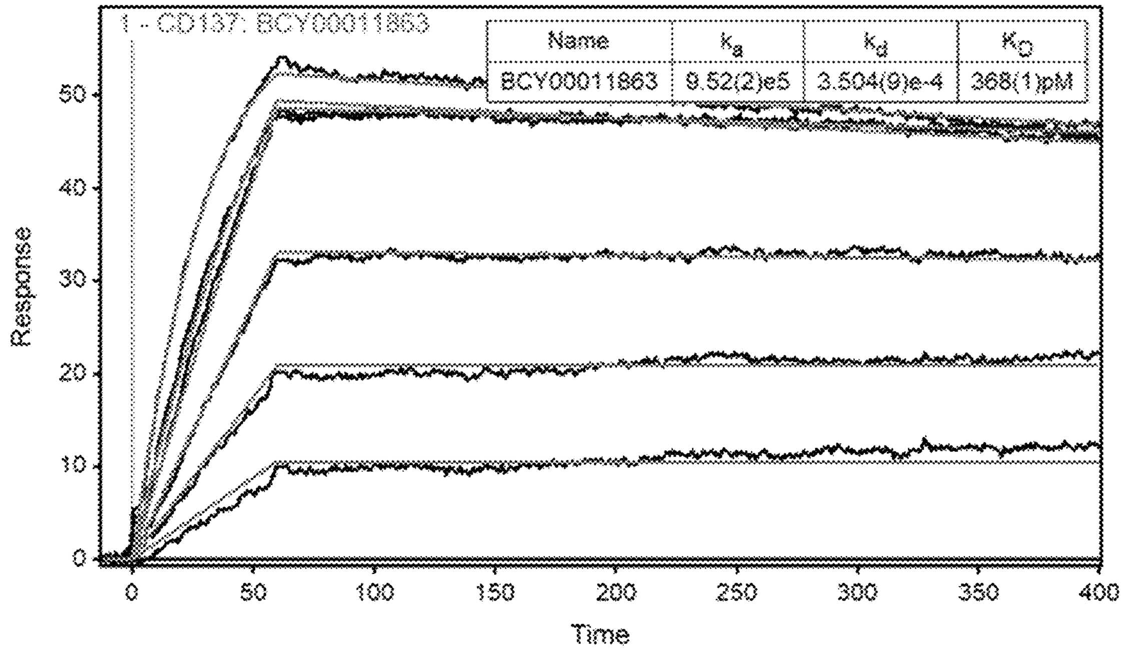

FIG. 10: Surface plasmon resonance (SPR) binding study of BCY11863 to immobilized (A) Nectin-4 and (B) CD137. Dual binding SPR assay immobilizing (C) CD137 and (D) Nectin-4 on the SPR chip followed by capturing BCY11863. The affinity of bound BCY11863 to soluble human Nectin-4 (C) or CD137 (D) is measured by flowing the soluble receptor over the chip at different concentrations. (E) Binding of BCY13582 (biotinylated BCY11863) immobilized on streptavidin SPR chip to soluble human CD137.

Figure 11:
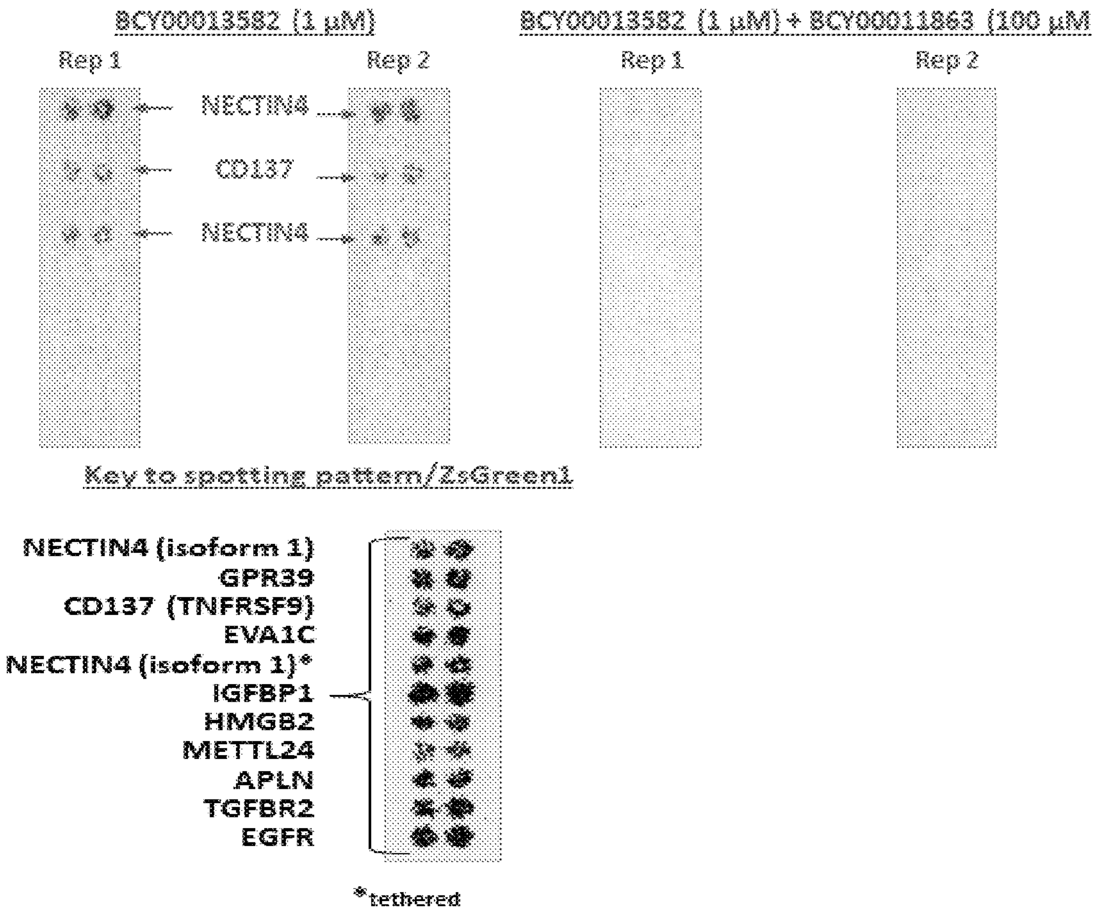

FIG. 11: Retrogenix's cell microarray technology used to explore non-specific off target interactions of BCY13582 (biotinylated BCY11863). Shown here is screening data that shows that 1 μM of BCY13582 added to microarray slides expressing 11 different proteins only binds to CD137 and Nectin-4 (detected using AlexaFluor647 labelled streptavidin). The binding signal is displaced when incubated with BCY11863.

Figure 12:
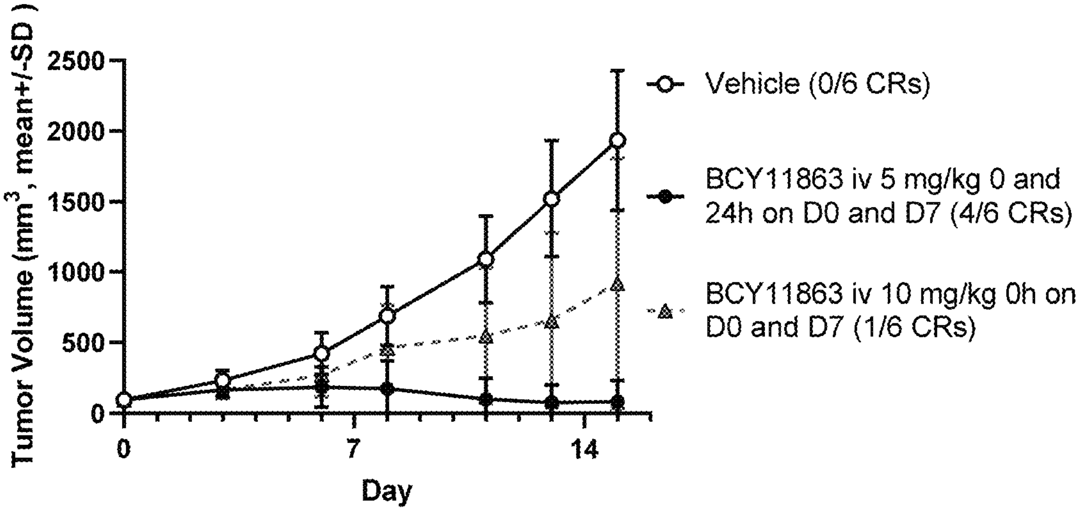

FIG. 12: Tumor growth curves of MC38#13 tumors in huCD137 C57Bl/6 mice demonstrate the anti-tumor activity of BCY11863 after different doses and dose intervals. The number of complete responder animals (CR; no palpable tumor) on day 15 after treatment initiation is indicated in parentheses.

Figure 13:
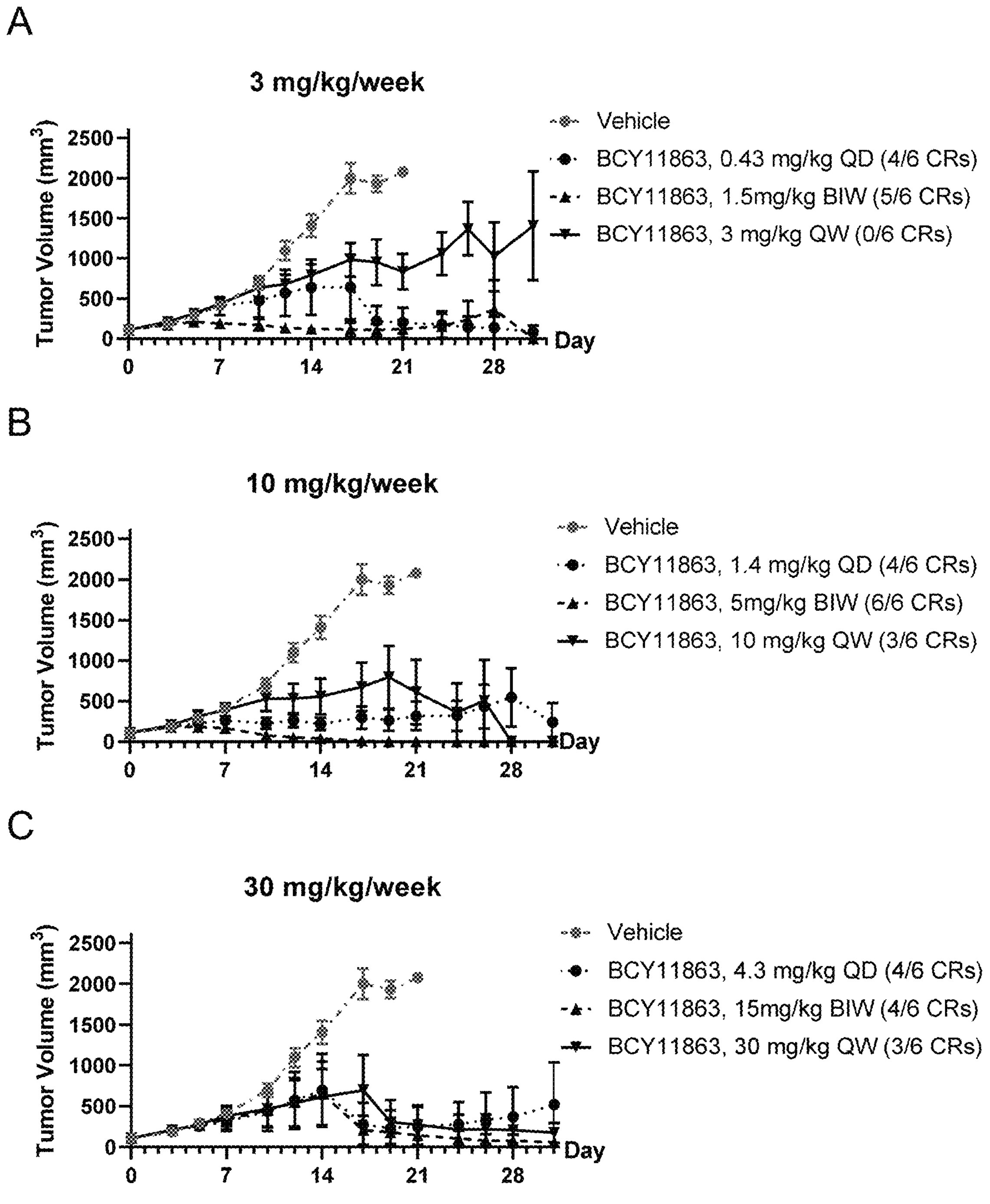

FIG. 13: Tumor growth curves (mean±SEM) of MC38#13 tumors (n=6/ cohort) in huCD137 C57Bl/6 mice demonstrate the anti-tumor activity of BCY11863 at different doses and dose schedules. The number of complete responder animals (CR; no palpable tumor) on day 52 after treatment initiation is indicated in parentheses. (A) Cohorts dosed with vehicle or 3 mg/kg total weekly dose of BCY11863. (B) Cohorts dosed with vehicle or 10 mg/kg total weekly dose of BCY11863. (C) Cohorts dosed with vehicle or 30 mg/kg total weekly dose of BCY11863.

Figure 14:
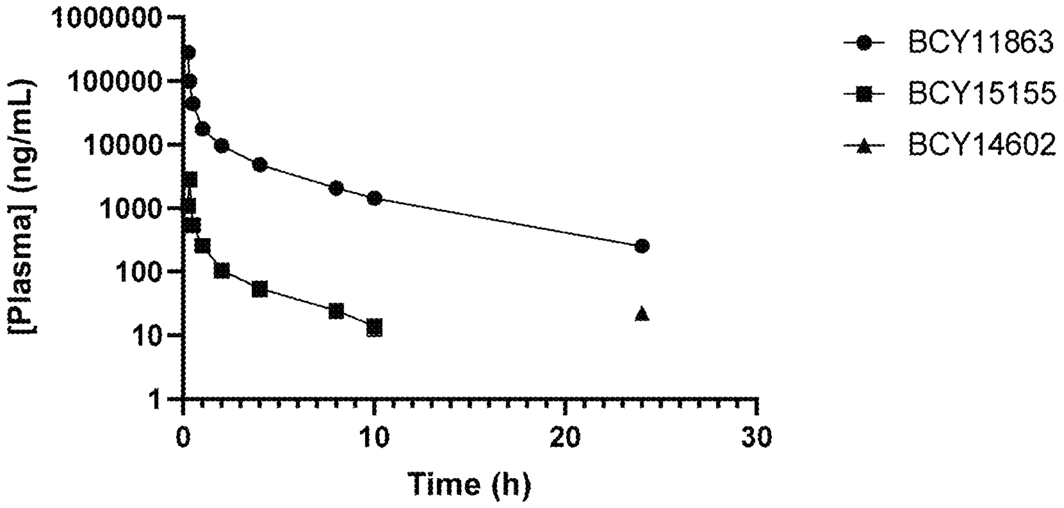

FIG. 14: Pharmacokinetics of heterotandem bicyclic peptide complex BCY11863 in SD Rats dosed IV at 100 mg/kg (n=3) and measurement of concentration of BCY11863 and potential metabolites BCY15155 and BCY14602 in plasma.

DETAILED DESCRIPTION OF THE INVENTION

According to a first aspect of the invention, there is provided a heterotandem bicyclic peptide complex comprising:

(a) a first peptide ligand which binds to Nectin-4 and which has the sequence $C_i$P[1Nal][dD]$C_{ii}$M[HArg]DWSTP[HyP]W$C_{iii}$ (SEQ ID NO: 1; BCY8116); conjugated via an N-(acid-$PEG_3$)-N-bis($PEG_3$-azide) linker to (b) two second peptide ligands which bind to CD137 both of which have the sequence Ac-$C_i$[tBuAla]PE[D-Lys(PYA)]PY$C_{ii}$FADPY[Nle]$C_{iii}$-A (SEQ ID NO: 2; BCY8928);

wherein each of said peptide ligands comprise a polypeptide comprising three reactive cysteine groups ($C_i$, $C_{ii}$ and $C_{iii}$), separated by two loop sequences, and a molecular scaffold which is 1,1',1"-(1,3,5-triazinane-1,3,5-triyl)triprop-2-en-1-one (TATA) and which forms covalent bonds with the reactive cysteine groups of the polypeptide such that two polypeptide loops are formed on the molecular scaffold;

wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

References herein to a N-(acid-$PEG_3$)-N-bis($PEG_3$-azide) linker include:
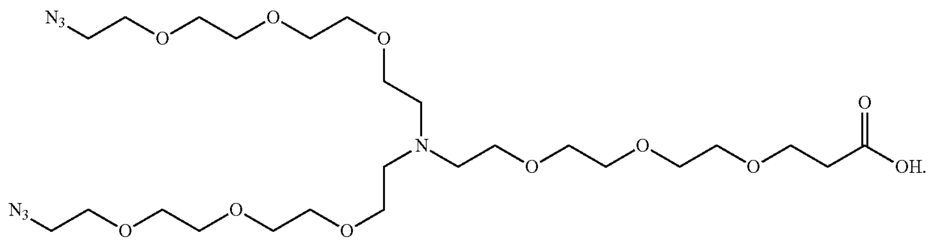
N-(acid-PEG3)-N-bis(PEG3-azide)
In one embodiment, the heterotandem bicyclic peptide complex is BCY11863:

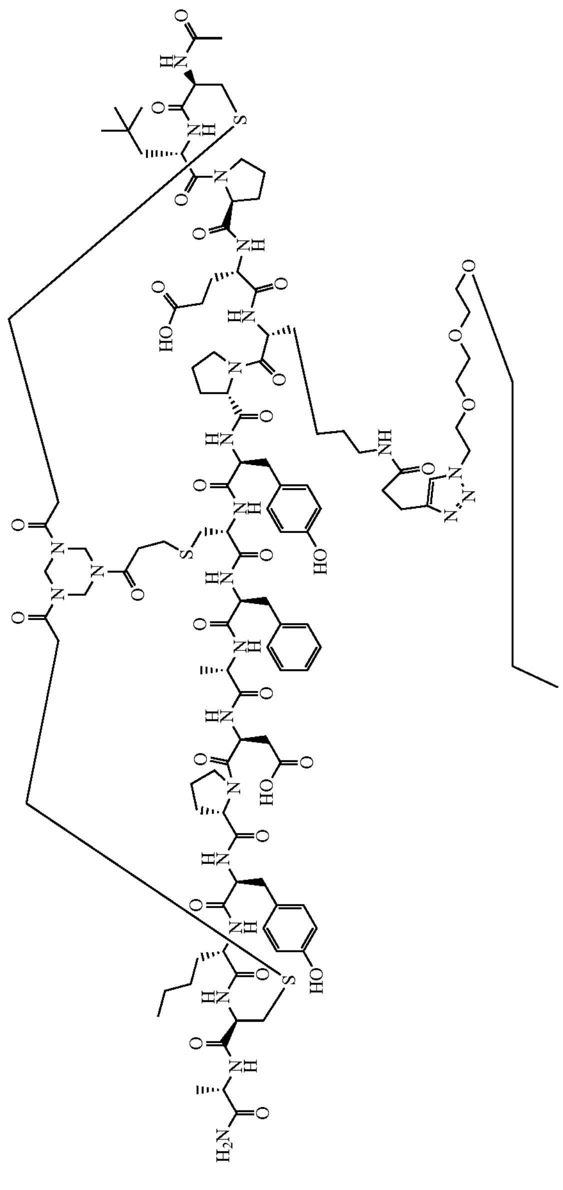

-continued
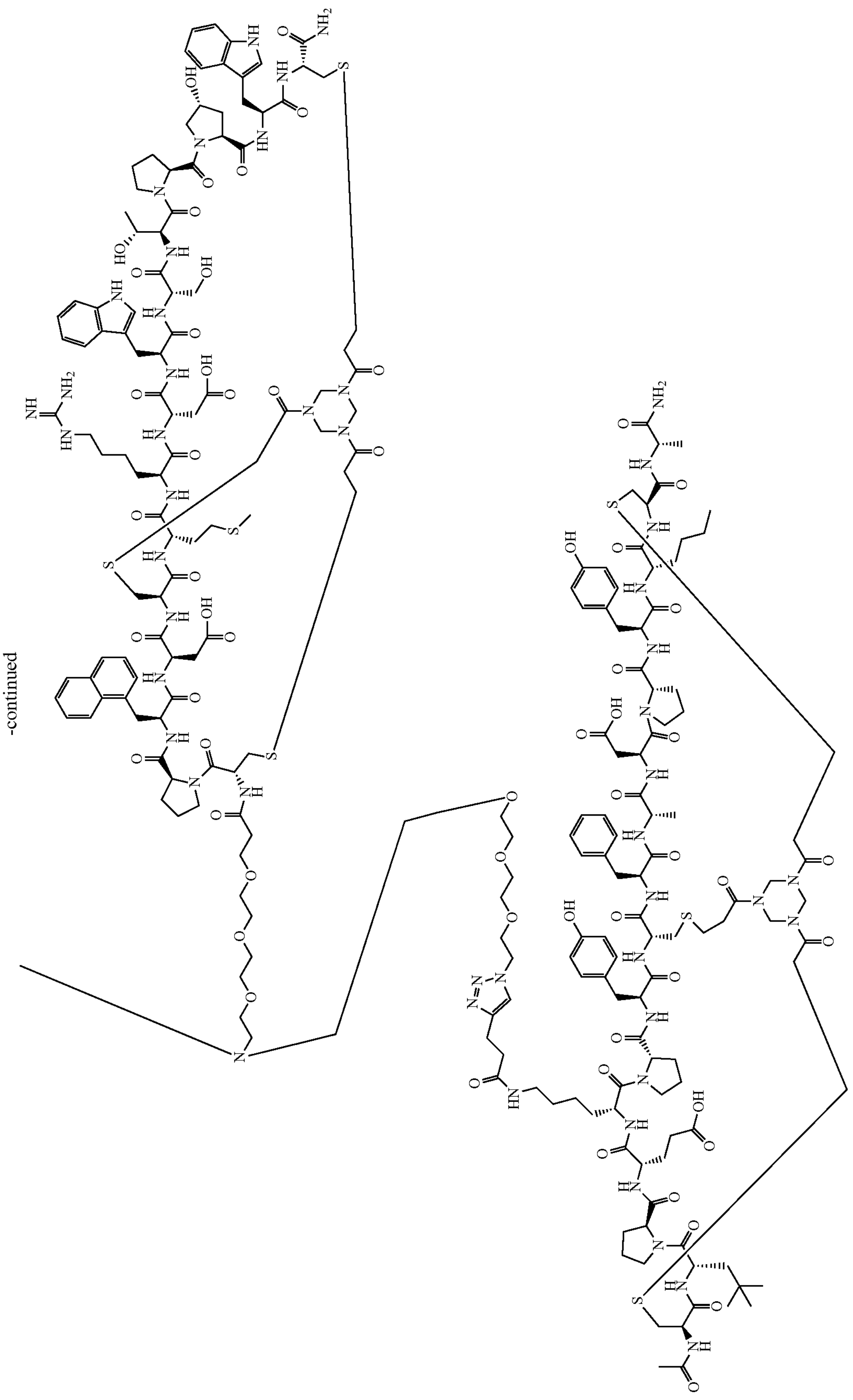
BCY00011863

Full details of BCY11863 are shown in Table A below:

TABLE A

| Composition of BCY11863 | | | | | |
|---|---|---|---|---|---|
| Complex No. | Nectin-4 BCY No. | Attachment Point | Linker | CD137 BCY Nos. | Attachment Point |
| BCY11863 | BCY8116 | N-terminus | N-(acid-PEG3)-N-bis(PEG3-azide) | BCY8928, BCY8928 | dLys (PYA)4 |

Figure 1:
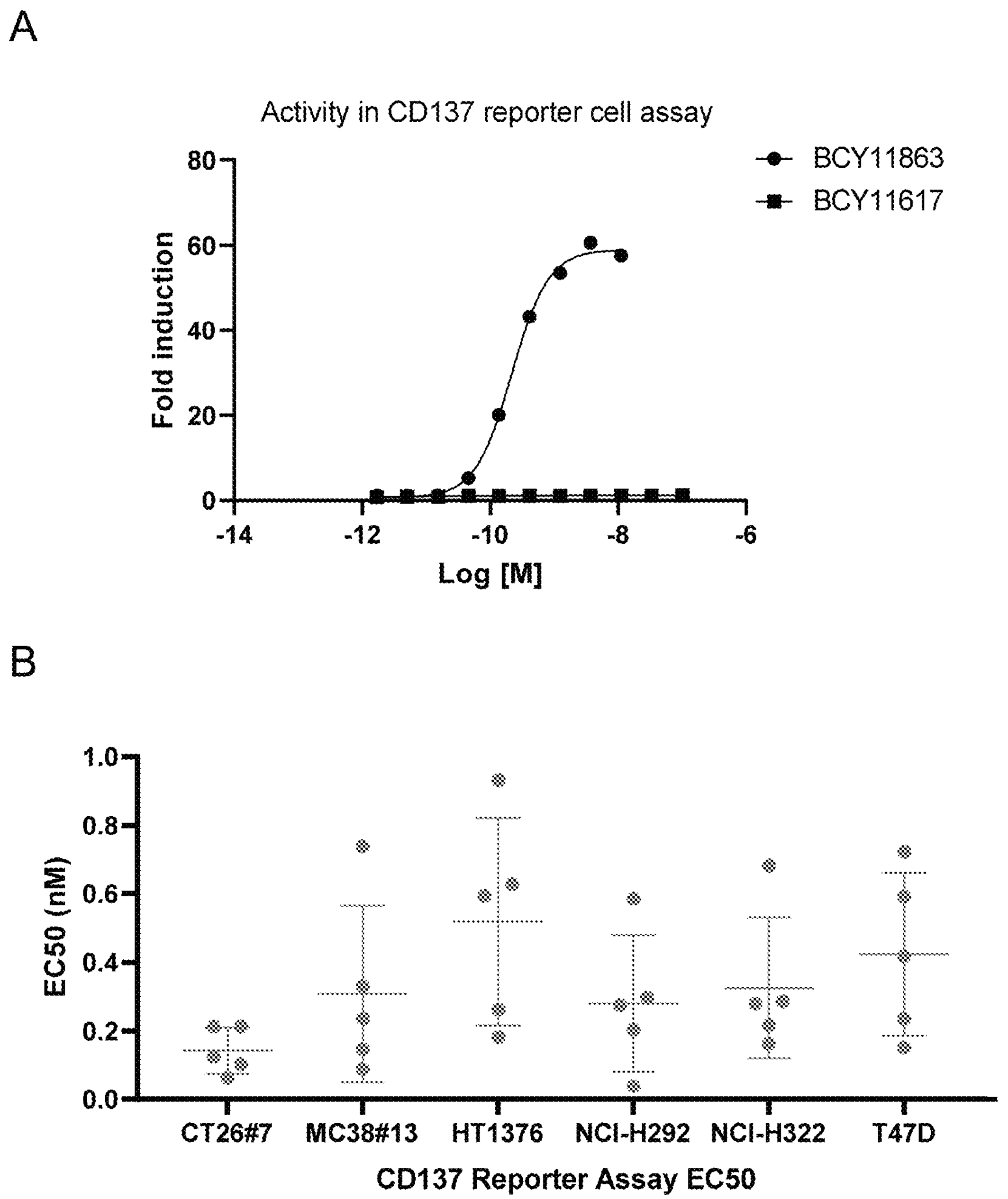
FIG. 1: (A) Analysis of the Nectin-4/ CD137 heterotandem bicyclic peptide complex in the Promega CD137 luciferase reporter assay in the presence of Nectin-4 expressing H292 cells. BCY11617 is a heterotandem bicyclic peptide complex that binds to Nectin-4 with the same affinity as BCY11863 but that does not bind to CD137. (B) Summary of EC50 (nM) of BCY11863 in the Promega CD137 luciferase reporter assay in coculture with different cell lines that express Nectin-4 endogenously or are engineered to overexpress Nectin-4.

Data is presented herein in FIG. 1 and Table 1 which shows that BCY11863 demonstrated strong CD137 activation in a CD137 reporter assay. In addition, data is presented herein in FIG. 2 and Table 2 which shows that BCY11863 induces robust IL-2 and IFN-γ cytokine secretion in a PBMC co-culture assays with multiple tumor cell lines and human PBMC donors. Furthermore, data is presented herein in FIG. 3 and Table 5 which shows that BCY11863 demonstrated an excellent PK profile with a terminal half-life of 4.1 hours in SD Rats and 5.3 hours in cyno. Data shown in FIGS. 10 and 11 along with methods section 11 and 12 demonstrate binding and exquisite selectivity of BCY11863 for its target Nectin-4 and CD137. FIGS. 4 and 5 demonstrate profound anti-tumor activity of BCY11863 in MC38#13 syngeneic mice and the formation of immunogenic memory after BCY11863 treatment. FIGS. 6 and 7 demonstrate anti-tumor activity of BCY11863 in CT26#7 syngeneic model with corresponding infiltration of cytotoxic T cells into the tumor. FIGS. 12 and 13 clearly demonstrate that BCY11863 does not have to maintain measurable plasma concentrations as dosing with 1.5 mg/kg BIW and 5 mg/kg at 0, 24 h in a week produced robust anti-tumor activity.

Reference herein is made to certain analogues (i.e. modified derivatives) and metabolites of BCY11863, each of which form additional aspects of the invention and are summarised in Table B below:

TABLE B

| Composition of BCY11863 analogues and metabolites | | | | | | |
|---|---|---|---|---|---|---|
| Complex No. | Nectin-4 BCY No. | Attachment Point | Linker | CD137 BCY No. | Attachment Point | Modifier |
| BCY13390 | BCY8116 | N-terminus | N-(acid-$PEG_3$)-N-bis($PEG_3$-azide) | BCY8928, BCY13389 | dLys(PYA)4 dLys(PYA)4 | |
| BCY13582 | BCY8116 | N-terminus | N-(acid-$PEG_3$)-N-bis($PEG_3$-azide) | BCY8928, BCY13389 | dLys(PYA)4 dLys(PYA)4 | Biotin-Peg 12 |
| BCY13583 | BCY8116 | N-terminus | N-(acid-$PEG_3$)-N-bis($PEG_3$-azide) | BCY8928, BCY13389 | dLys(PYA)4 dLys(PYA)4 | Alexa Fluor 488 |
| BCY13628 | BCY8116 | N-terminus | N-(acid-$PEG_3$)-N-bis($PEG_3$-azide) | BCY8928, BCY13389 | dLys(PYA)4 dLys(PYA)4 | Cyanine 5 |
| BCY15155 | BCY8116 | N-terminus | N-(acid-$PEG_3$)-N-bis($PEG_3$-azide) | BCY8928, BCY14601 | dLys(PYA)4 dLys(PYA)4 | |
| BCY14602 | BCY8116 | N-terminus | N-(acid-$PEG_3$)-N-bis($PEG_3$-azide) | BCY14601 | dLys(PYA)4 | |

wherein BCY14601 represents a bicyclic peptide ligand having the sequence of $C_i$[tBuAla]PE[D-Lys (PYA)]PY$C_{ii}$-FADPY[Nle]$C_{iii}$-A (SEQ ID NO: 3) with TATA as a molecular scaffold;

and wherein BCY13389 represents a bicyclic peptide ligand having the sequence of [Ac]$C_i$[tBuAla]PE[D-Lys(PYA)]PY$C_{ii}$FADPY[Nle]$C_{iii}$-K (SEQ ID NO: 4) with TATA as a molecular scaffold.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) $4^{th}$ ed., John Wiley & Sons, Inc.), which are incorporated herein by reference.

Nomenclature

Numbering

When referring to amino acid residue positions within compounds of the invention, cysteine residues ($C_i$, $C_{ii}$ and $C_{iii}$) are omitted from the numbering as they are invariant, therefore, the numbering of amino acid residues within SEQ ID NO: 1 is referred to as below:

(SEQ ID NO: 1)

$C_i$-$P_1$-$1Nal_2$-$dD_3$-$C_{ii}$-$M_4$-$HArg_5$-$D_6$-$W_7$-$S_8$-$T_9$-$P_{10}$-$HyP_{11}$-$W_{12}$-$C_{iii}$.

For the purpose of this description, the bicyclic peptides are cyclised with 1,1',1"-(1,3,5-triazinane-1,3,5-triyl) triprop-2-en-1-one (TATA) and yielding a tri-substituted structure. Cyclisation with TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal BAla-Sar10-Ala tail would be denoted as:

(SEQ ID NO: X)

βAla-Sar10-A-.

Inversed Peptide Sequences

In light of the disclosure in Nair et al (2003) J Immunol 170 (3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa). For the avoidance of doubt, references to amino acids either as their full name or as their amino acid single or three letter codes are intended to be represented herein as L-amino acids unless otherwise stated. If such an amino acid is intended to be represented as a D-amino acid then the amino acid will be prefaced with a lower case d within square parentheses, for example [dA], [dD], [dE], [dK], [d1Nal], [dNle], etc.

Advantages of the Peptide Ligands

Certain heterotandem bicyclic peptide complexes of the present invention have a number of advantageous properties which enable them to be considered as suitable drug-like molecules for injection, inhalation, nasal, ocular, oral or topical administration. Such advantageous properties include:

- Species cross-reactivity. This is a typical requirement for preclinical pharmacodynamics and pharmacokinetic evaluation;
- Protease stability. Heterotandem bicyclic peptide complexes should ideally demonstrate stability to plasma proteases, epithelial ("membrane-anchored") proteases, gastric and intestinal proteases, lung surface proteases, intracellular proteases and the like. Protease stability should be maintained between different species such that a heterotandem bicyclic peptide lead candidate can be developed in animal models as well as administered with confidence to humans;
- Desirable solubility profile. This is a function of the proportion of charged and hydrophilic versus hydrophobic residues and intra/inter-molecular H-bonding, which is important for formulation and absorption purposes;
- Selectivity. Certain heterotandem bicyclic peptide complexes of the invention demonstrate good selectivity over other targets;
- An optimal plasma half-life in the circulation. Depending upon the clinical indication and treatment regimen, it may be required to develop a heterotandem bicyclic peptide complex for short exposure in an acute illness management setting, or develop a heterotandem bicyclic peptide complex with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.
- Crucially, data is presented herein where the heterotandem bicyclic peptide complex of the invention demonstrates anti-tumor efficacy when dosed at a frequency that does not maintain plasma concentrations above the in vitro $EC_{50}$ of the compound. This is in contrast to larger recombinant biologic (i.e. antibody based) approaches to CD137 agonism or bispecific CD137 agonism (Segal et al., Clin Cancer Res., 23 (8): 1929-1936 (2017), Claus et al., Sci Trans Med., 11 (496): eaav5989, 1-12 (2019), Hinner et al., Clin Cancer Res., 25 (19): 5878-5889 (2019)). Without being bound by theory, the reason for this observation is thought to be due to the fact that heterotandem bicycle complexes have relatively low molecular weight (typically <15 kDa), they are fully synthetic and they are tumor targeted agonists of CD137. As such, they have relatively short plasma half lives but good tumor penetrance and retention. Data is presented herein which fully supports these advantages. For example, anti-tumor efficacy in syngeneic rodent models in mice with humanized CD137 is demonstrated either daily or every $3^{rd}$ day. In addition, intraperitoneal pharmacokinetic data shows that the plasma half life is <3 hours, which would predict that the circulating concentration of the complex would consistently drop below the in vitro $EC_{50}$ between doses. Furthermore, tumor pharmacokinetic data shows that levels of heterotandem bicycle complex in tumor tissue may be higher and more sustained as compared to plasma levels.
- It will be appreciated that this observation forms an important further aspect of the invention. Thus, according to a further aspect of the invention, there is provided a method of treating cancer which comprises administration of a heterotandem bicyclic peptide complex as defined herein at a dosage frequency which does not sustain plasma concentrations of said complex above the in vitro $EC_{50}$ of said complex.

Immune Memory. Coupling the cancer cell binding bicyclic peptide ligand with the immune cell binding bicyclic peptide ligand provides the synergistic advantage of immune memory. Data is presented herein which demonstrates that the heterotandem bicyclic peptide complex of the invention not only eradicates tumors but upon readministration of the tumorigenic agent, none of the inoculated complete responder mice developed tumors (see FIG. 5). This indicates that treatment with the selected heterotandem bicyclic peptide complex of the invention has induced immunogenic memory in the complete responder mice. This has a significant clinical advantage in order to prevent recurrence of said tumor once it has been initially controlled and eradicated.

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three reactive groups selected from cysteine, 3-mercaptopropionic acid and/or cysteamine and form at least two loops on the scaffold.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono-or di-salts) may be formed with a wide variety of acids, both inorganic and organic. Examples of acid addition salts include mono-or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —$COO^-$), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the invention contain an amine function, these may form quaternary ammonium salts, for example by reaction with an alkylating agent according to methods well known to the skilled person. Such quaternary ammonium compounds are within the scope of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102 (2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

- Incorporating hydrophobic moieties that exploit the hydrophobic effect and lead to lower off rates, such that higher affinities are achieved;
- Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and
- Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the Nectin-4 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^{2}H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio) conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91 (26): 12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptides to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptides, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

According to a further aspect of the invention, there is provided a heterotandem bicyclic peptide complex as defined herein for use in preventing, suppressing or treating cancer.

Examples of cancers (and their benign counterparts) which may be treated (or inhibited) include, but are not limited to tumors of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumors of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumors, benign and malignant histiocytomas, and dermatofibrosarcomaprotuberans; tumors of the central or peripheral nervous system (for example astrocytomas, gliomas and glioblastomas, meningiomas, ependymomas, pineal tumors and schwannomas); endocrine tumors (for example pituitary tumors, adrenal tumors, islet cell tumors, parathyroid tumors, carcinoid tumors and medullary carcinoma of the thyroid); ocular and adnexal tumors (for example retinoblastoma); germ cell and trophoblastic tumors (for example teratomas, seminomas, dysgerminomas, hydatidiform moles and choriocarcinomas); and paediatric and embryonal tumors (for example medulloblastoma, neuroblastoma, Wilms tumor, and primitive neuroectodermal tumors); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

In general, the heterotandem bicyclic peptide complex of the invention may be prepared in accordance with the following general method:

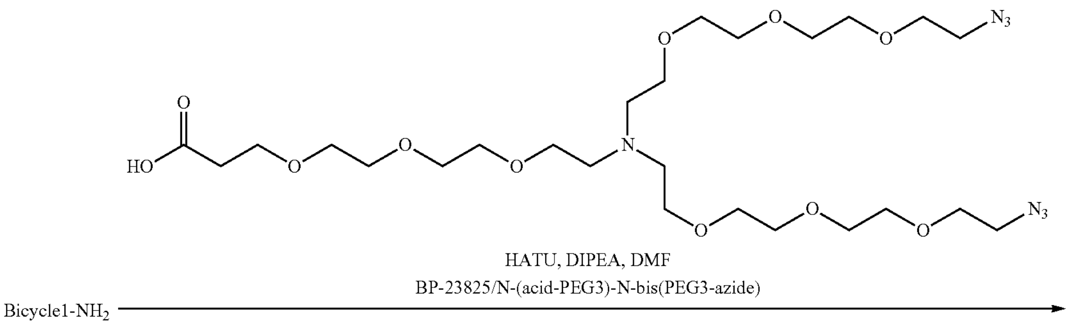

1

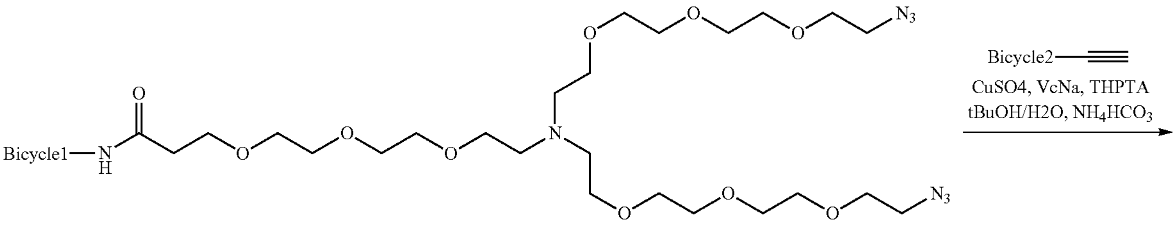

2

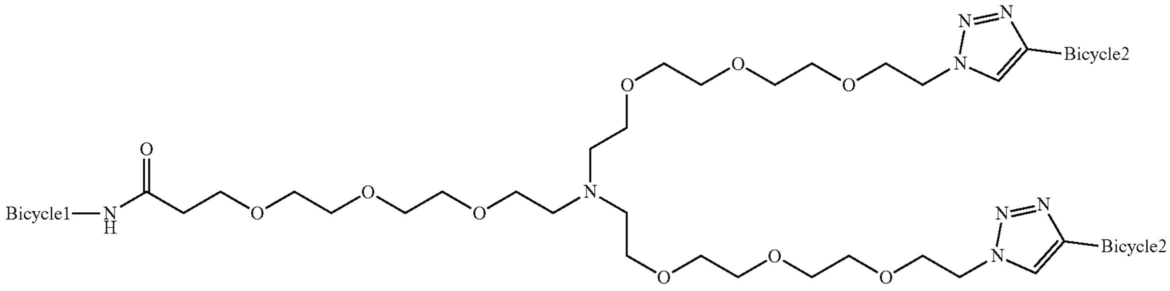

3

All solvents are degassed and purged with $N_2$ 3 times. A solution of BP-23825 (1.0 eq), HATU (1.2 eq) and DIEA (2.0 eq) in DMF is mixed for 5 minutes, then Bicycle1 (1.2 eq.) is added. The reaction mixture is stirred at 40° C. for 16 hr. The reaction mixture is then concentrated under reduced pressure to remove solvent and purified by prep-HPLC to give intermediate 2.

A mixture of intermediate 2 (1.0 eq) and Bicycle2 (2.0 eq) are dissolved in t-BuOH/$H_2O$ (1:1), and then $CuSO_4$ (1.0 eq), VcNa (4.0 eq), and THPTA (2.0 eq) are added. Finally, 0.2 M $NH_4HCO_3$ is added to adjust pH to 8. The reaction mixture is stirred at 40° C. for 16 hr under $N_2$ atmosphere. The reaction mixture was directly purified by prep-HPLC.

More detailed experimental for the heterotandem bicyclic peptide complex of the invention is provided herein below:

Example 1: Synthesis of BCY11863

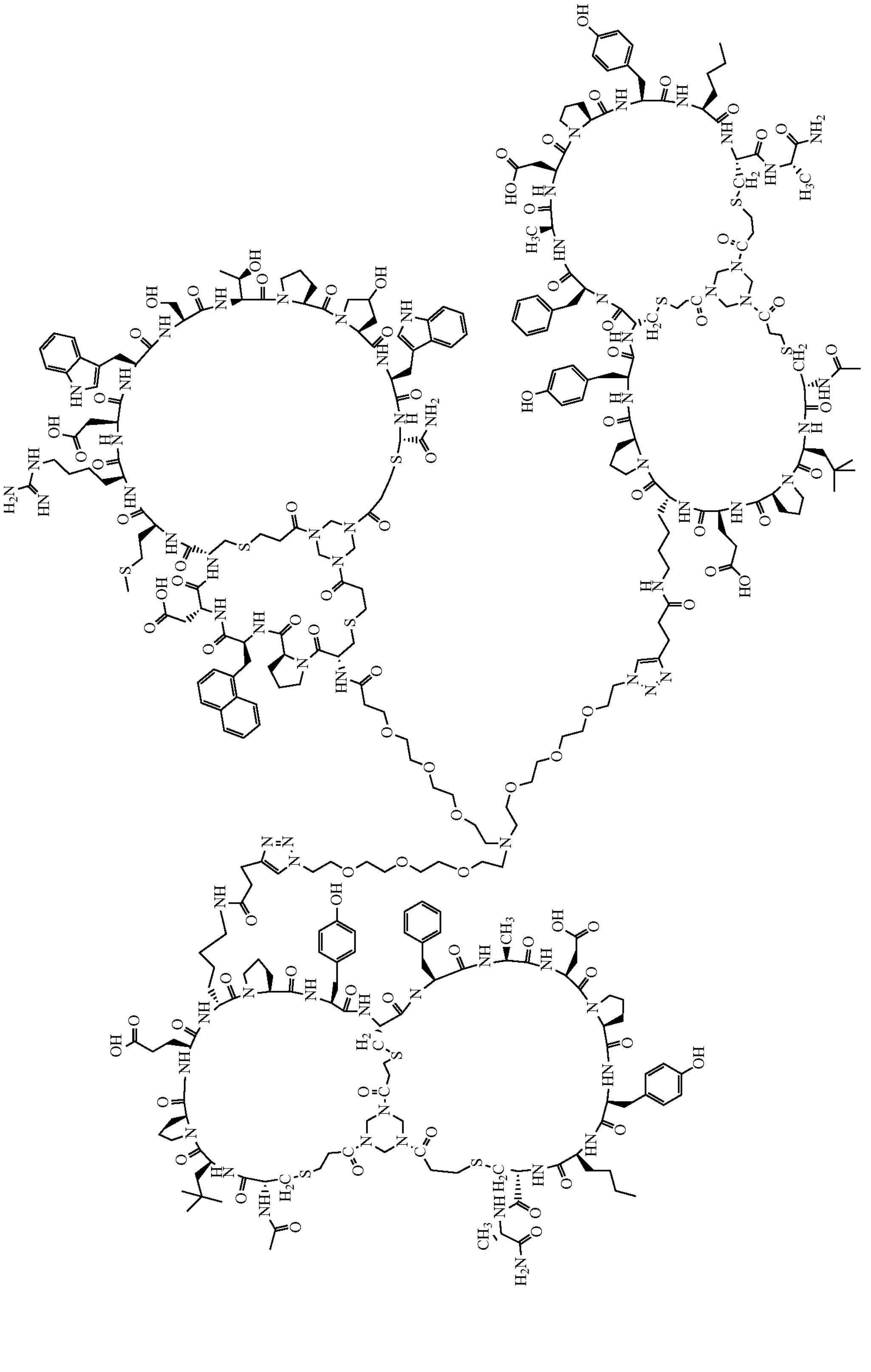
BCY11863

Procedure for Preparation of BCY12476

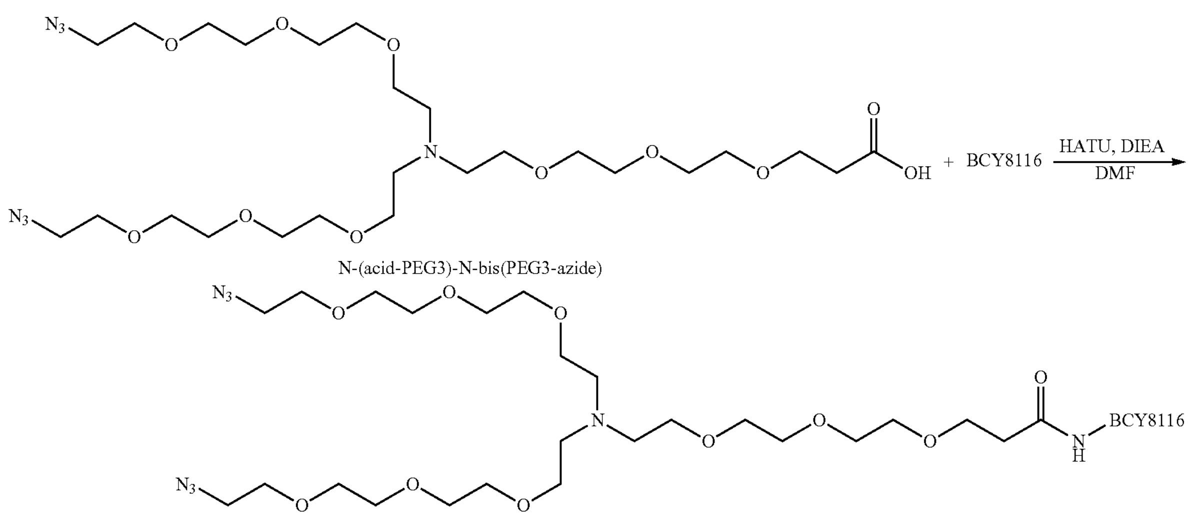

BCY12476

A mixture of N-(acid-PEG3)-N-bis(PEG3-azide) (70.0 mg, 112.2 µmol, 1.0 eq), HATU (51.2 mg, 134.7 µmol, 1.2 eq) and DIEA (29.0 mg, 224.4 µmol, 40 µL, 2.0 eq) was dissolved in DMF (2 mL), and mixed for 5 min. Then BCY8116 (294.0 mg, 135.3 µmol, 1.2 eq) was added. The reaction mixture was stirred at 40° C. for 16 hr. LC-MS showed one main peak with desired m/z. The reaction mixture was concentrated under reduced pressure to remove solvent and produced a residue. The residue was then purified by preparative HPLC. BCY12476 (194.5 mg, 66.02 µmol, 29% yield, 94% purity) was obtained as a white solid. Calculated MW: 2778.17, observed m/z: 1389.3 ($[M+2H]^{2+}$), 926.7 ($[M+3H]^{3+}$).

Procedure for Preparation of BCY11863

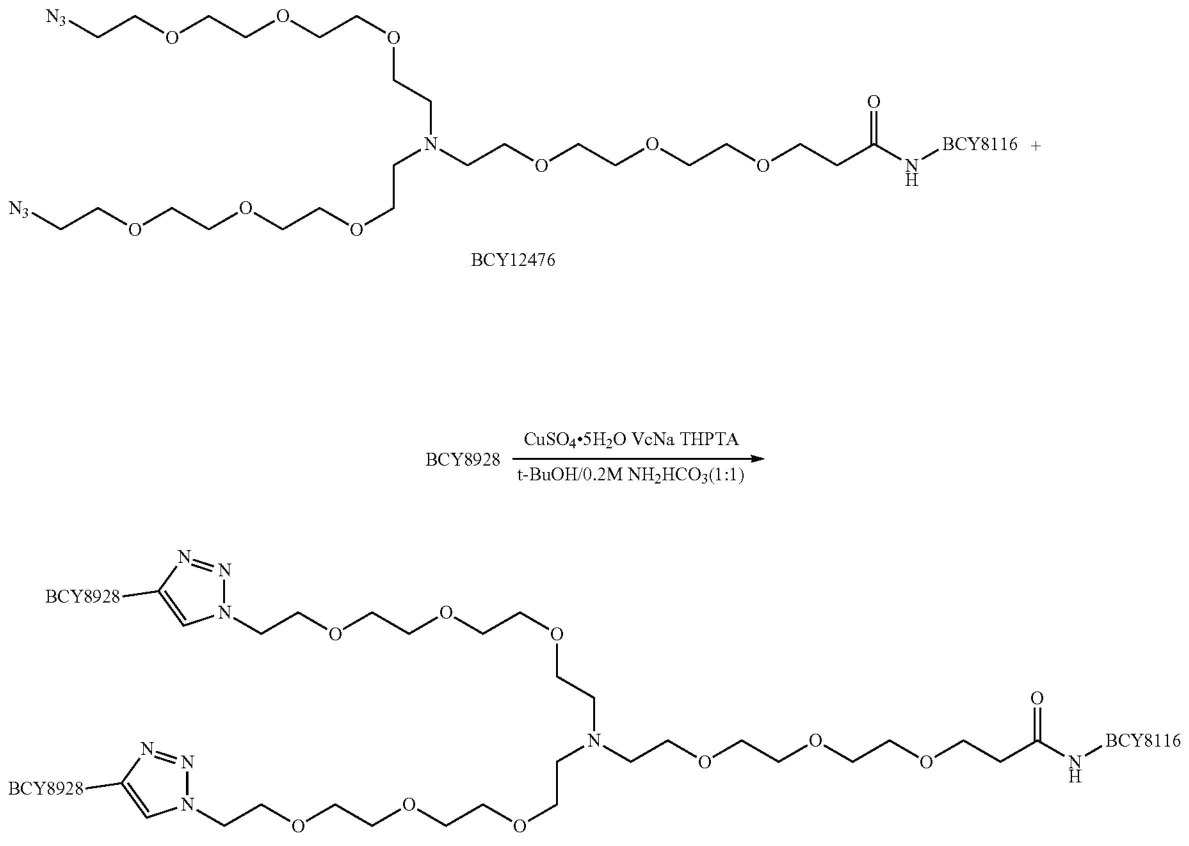

BCY11863

A mixture of BCY12476 (100.0 mg, 36.0 μmol, 1.0 eq), BCY8928 (160.0 mg, 72.0 μmol, 2.0 eq) were first dissolved in 2 mL of t-BuOH/$H_2O$ (1:1), and then $CuSO_4$ (0.4 M, 180 μL, 1.0 eq) and VcNa (28.5 mg, 143.8 μmol, 4.0 eq), THPTA (31.2 mg, 71.8 μmol, 2.0 eq) were added. Finally, 0.2 M $NH_4HCO_3$ was added to adjust pH to 8. All solvents here were degassed and purged with $N_2$. The reaction mixture was stirred at 40° C. for 16 hr under $N_2$ atmosphere. LC-MS showed BCY8928 remained and desired m/z was also detected. The reaction mixture was directly purified by preparative HPLC. First purification resulted in BCY11863 (117.7 mg, 15.22 μmol, 42.29% yield, 93.29% purity) as TFA salt, while less pure fractions were purified again by preparative HPLC, producing BCY11863 (33.2 mg, 4.3 μmol, 12% yield, 95% purity) as TFA salt. Calculated MW: 7213.32, observed m/z: 1444.0 ($[M+5H]^{5+}$).

Example 2: Synthesis of BCY13390

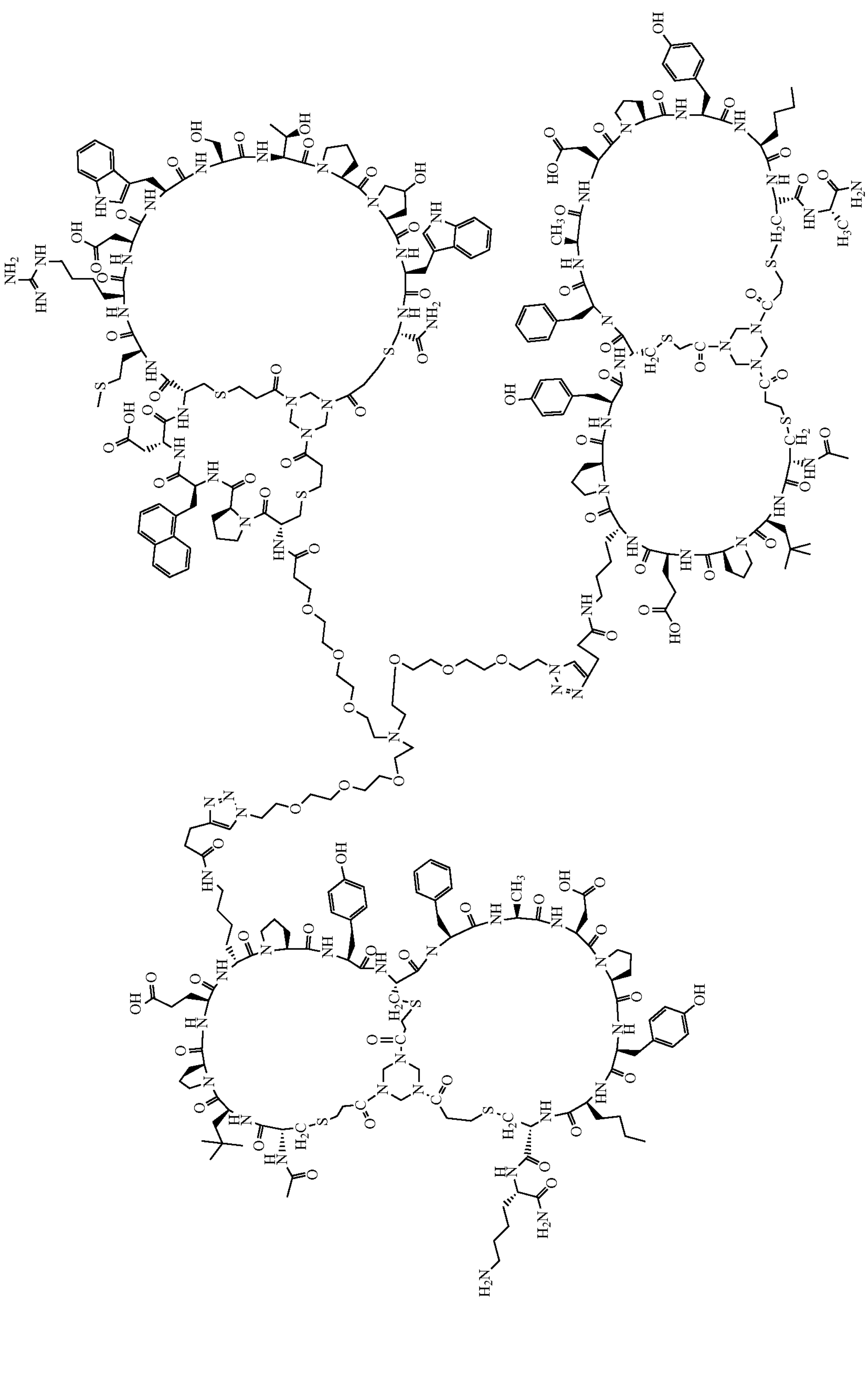
BCY13390

Procedure for Preparation of BCY13689

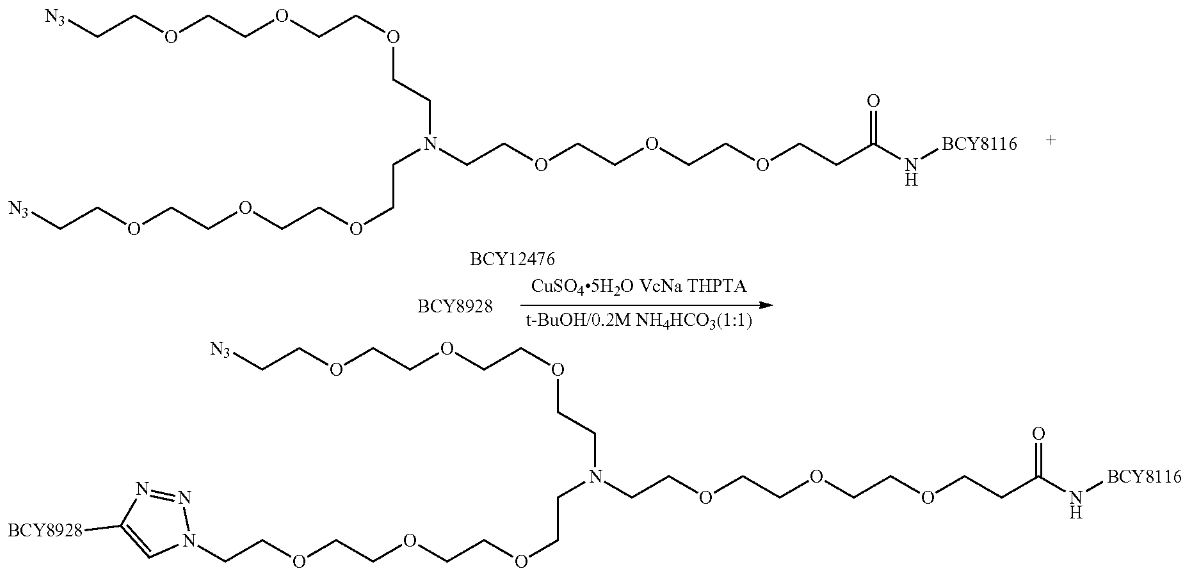

BCY13689

A mixture of BCY12476 (47.0 mg, 16.91 μmol, 1.0 eq), BCY8928 (30.0 mg, 13.53 μmol, 0.8 eq), and THPTA (36.7 mg, 84.55 μmol, 5.0 eq) was dissolved in t-BuOH/$H_2O$ (1:1, 8 mL, pre-degassed and purged with $N_2$), and then $CuSO_4$ (0.4 M, 21.0 μL, 0.5 eq) and VcNa (67.0 mg, 338.21 μmol, 20.0 eq) were added under $N_2$. The pH of this solution was adjusted to 8 by dropwise addition of 0.2 M $NH_4HCO_3$ (in 1:1 t-BuOH/$H_2O$), and the solution turned light yellow. The reaction mixture was stirred at 25° C. for 1.5 h under $N_2$ atmosphere. LC-MS showed that some BCY12476 remained, BCY8928 was consumed completely, and a peak with the desired m/z was detected. The reaction mixture was filtered and concentrated under reduced pressure to give a residue. The crude product was purified by preparative HPLC, and BCY13689 (25.3 mg, 4.56 μmol, 27% yield, 90% purity) was obtained as a white solid. Calculated MW: 4995.74, observed m/z: 1249.4 ($[M+4H]^{4+}$), 999.9 ($[M+5H]^{5+}$).

Procedure for Preparation of BCY13390

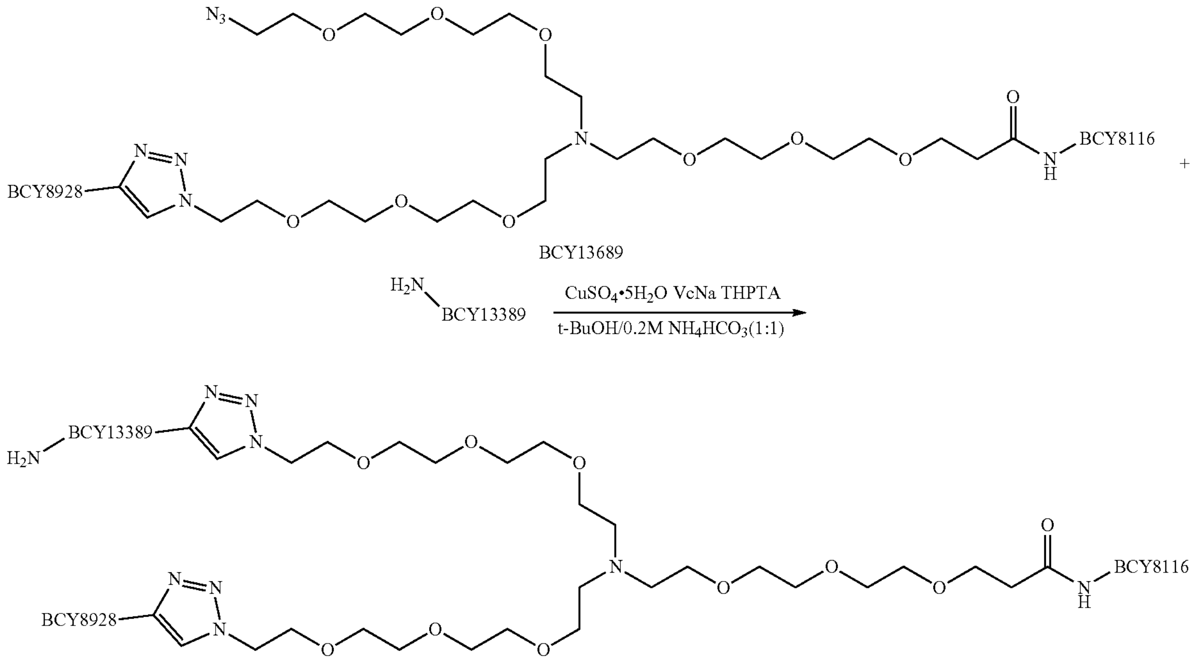

BCY13390

A mixture of BCY13689 (43.6 mg, 8.73 μmol, 1.0 eq), BCY13389 (20.8 mg, 9.16 μmol, 1.05 eq), and THPTA (3.8 mg, 8.73 μmol, 1.0 eq) was dissolved in t-BuOH/$H_2O$ (1:1, 1 mL, pre-degassed and purged with $N_2$), and then $CuSO_4$ (0.4 M, 22.0 μL, 1.0 eq) and VcNa (3.5 mg, 17.45 μmol, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25° C. for 2 hr under $N_2$ atmosphere. LC-MS showed a significant peak corresponding to the desired m/z. The reaction mixture was filtered and concentrated under reduced pressure to give a residue. The crude product was purified by preparative HPLC, and BCY13390 (33.8 mg, 4.21 μmol, 48% yield, 90% purity) was obtained as a white solid. Calculated MW: 7270.41, observed m/z: 1454.9 ($[M+5H]^{5+}$), 1213.2 ($[M+6H]^{6+}$).

Example 3: Synthesis of BCY13582

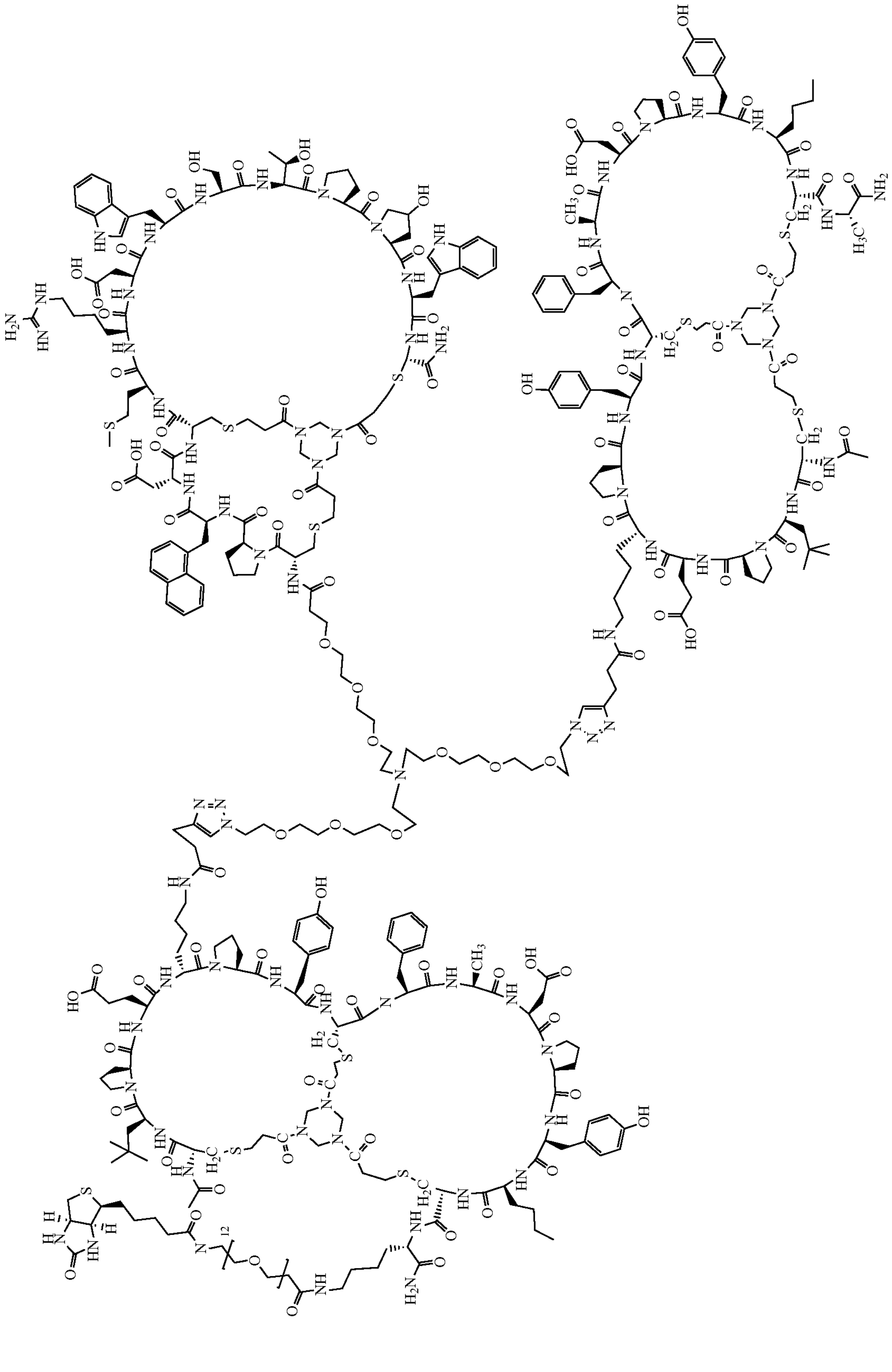
BCY13582

Procedure for Preparation of BCY13582

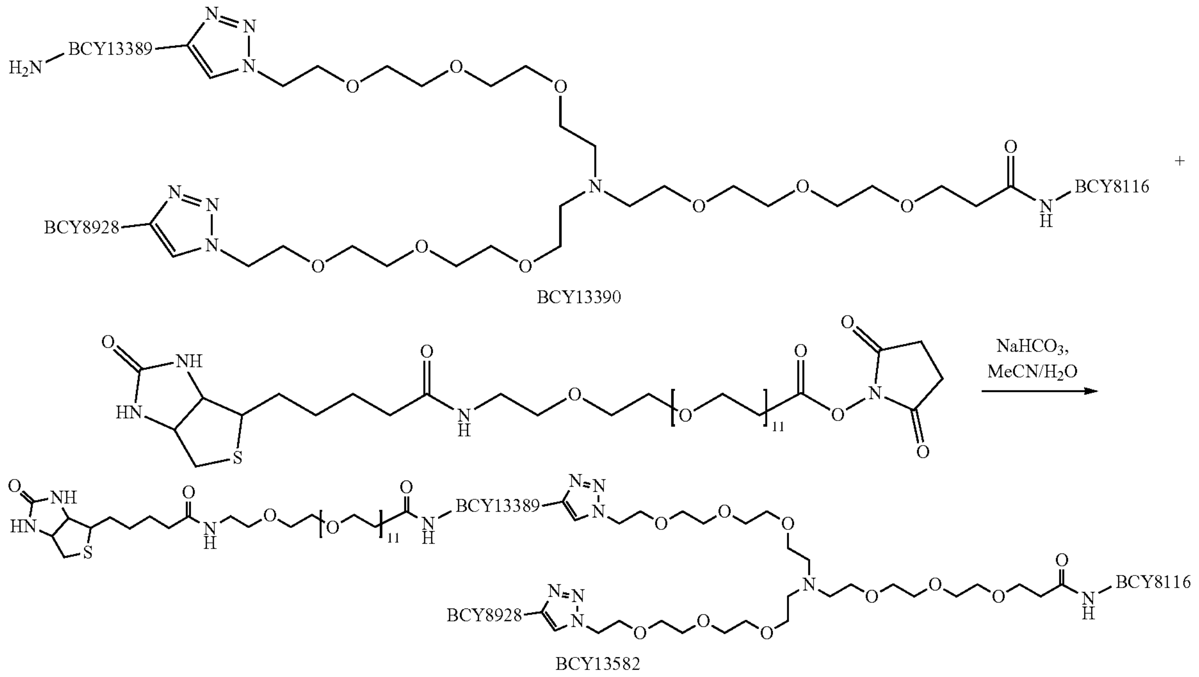

A mixture of BCY13390 (5.0 mg, 0.6 μmol, 1.0 eq), biotin-PEG12-NHS ester (CAS 365441-71-0, 0.7 mg, 0.72 μmol, 1.1 eq) was dissolved in MeCN/$H_2O$ (1:1, 2 mL). The pH of this solution was adjusted to 8 by dropwise addition of 1.0 M $NaHCO_3$. The reaction mixture was stirred at 25° C. for 0.5 hr. LC-MS showed BCY13390 was consumed completely, and one main peak with desired m/z was detected. The reaction mixture was filtered and concentrated under reduced pressure to give a residue. The crude product was purified by preparative HPLC, and BCY13582 (2.5 mg, 0.30 μmol, 43% yield, 96% purity) was obtained as a white solid. Calculated MW: 8096.43, observed m/z: 1351.1 ($[M+6H]^{6+}$), 1158.5 ($[M+7H]^{7+}$)

Example 4: Synthesis of BCY13583

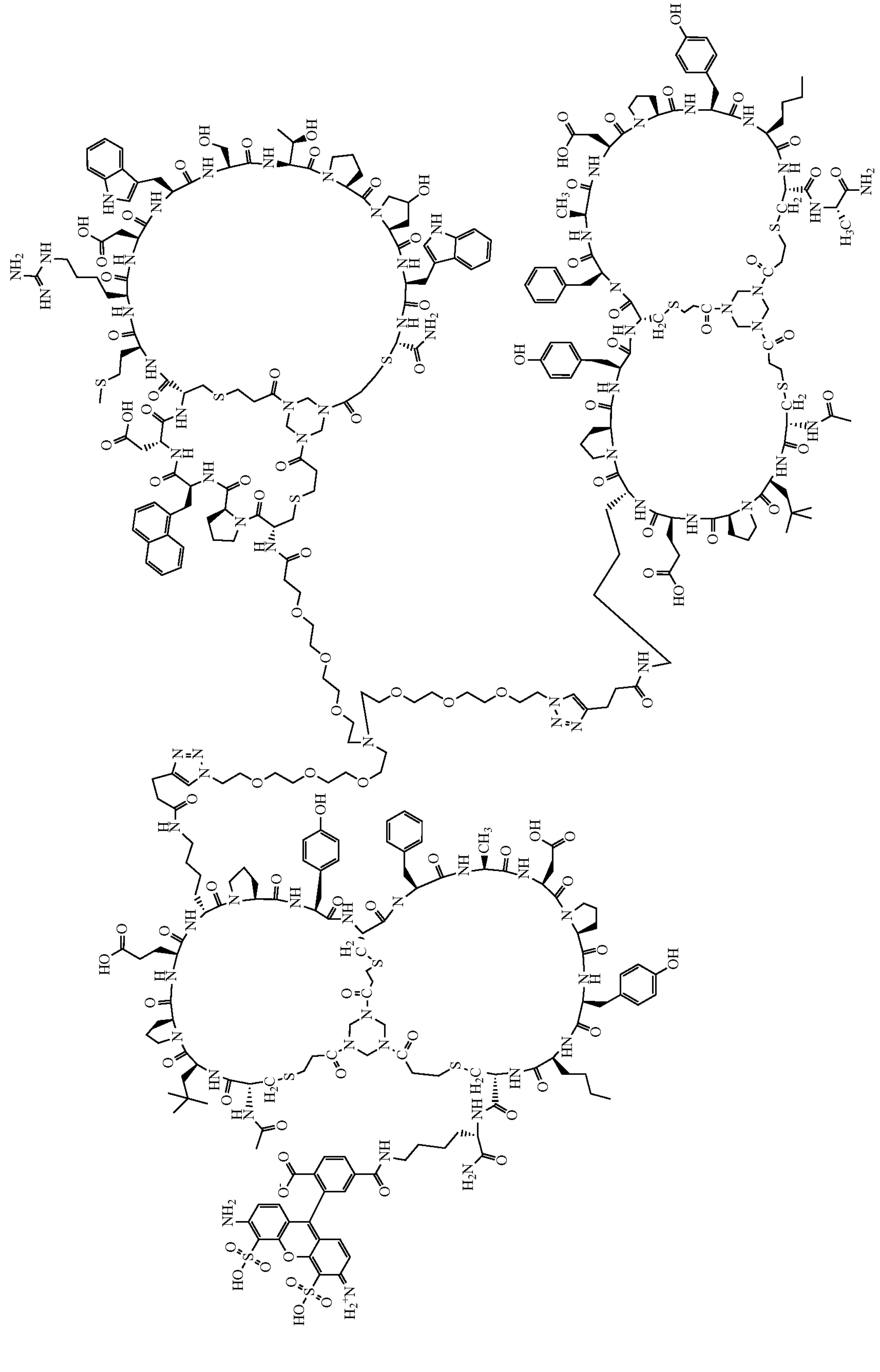
BCY13583

Procedure for preparation of BCY13583

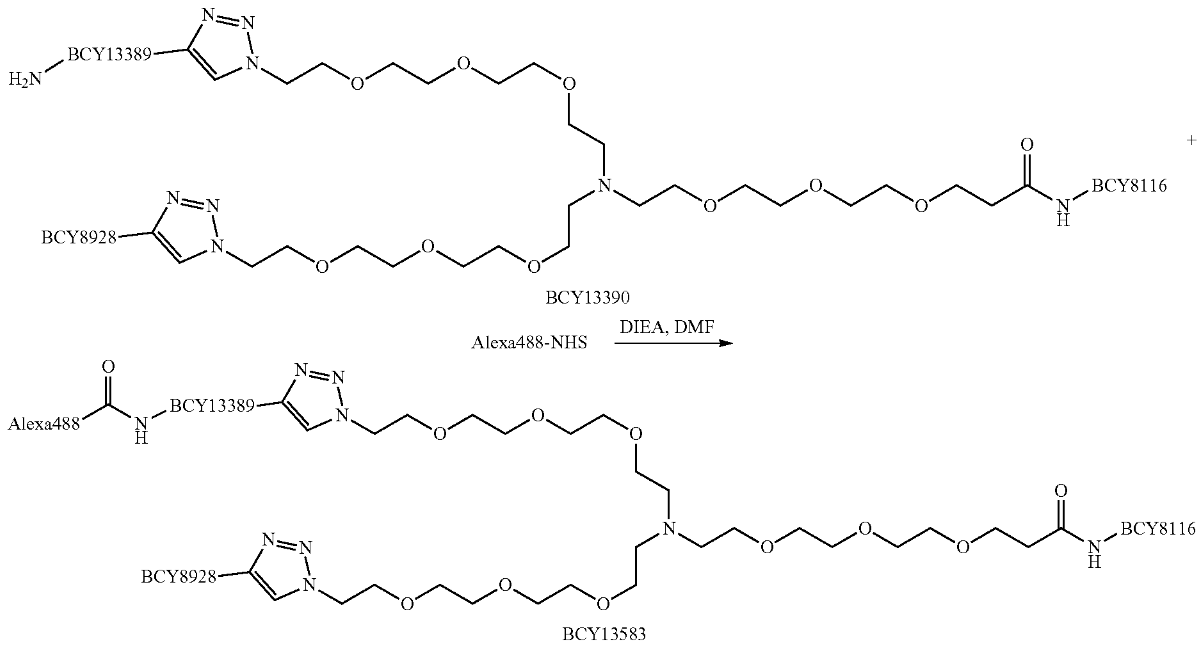

BCY13390

BCY13583

A mixture of BCY13390 (15.0 mg, 2.06 μmol, 1.0 eq) and Alexa Fluor® 488 NHS ester (2.5 mg, 4.12 μmol, 2.0 eq) was dissolved in DMF (0.5 mL). DIEA (2.6 mg, 20.63 μmol, 3.6 μL, 10 eq) was then added dropwise. The reaction mixture was stirred at 25° C. for 1 hr. LC-MS showed BCY13390 remained, and one main peak with desired m/z was detected. Additional Alexa Fluor® 488 NHS ester (2.0 mg, 3.09 μmol, 1.5 eq) was added to the reaction mixture, and the reaction mixture was stirred at 25° C. for one additional hour. HPLC showed BCY13390 was consumed completely. The reaction mixture was filtered and concentrated under reduced pressure to give a residue. The crude product was purified by preparative HPLC, and BCY13583 (5 mg, 0.61 μmol, 29% yield, 95% purity) was obtained as a red solid. Calculated MW: 7787.9, observed m/z: 1948.8 ($[M+4H+H_2O]^{4+}$), 1558.6 ($[M+5H+H2O]^{5+}$), 1299.1 ($[M+7H+H2O]^{7+}$).

Example 5: Synthesis of BCY13628

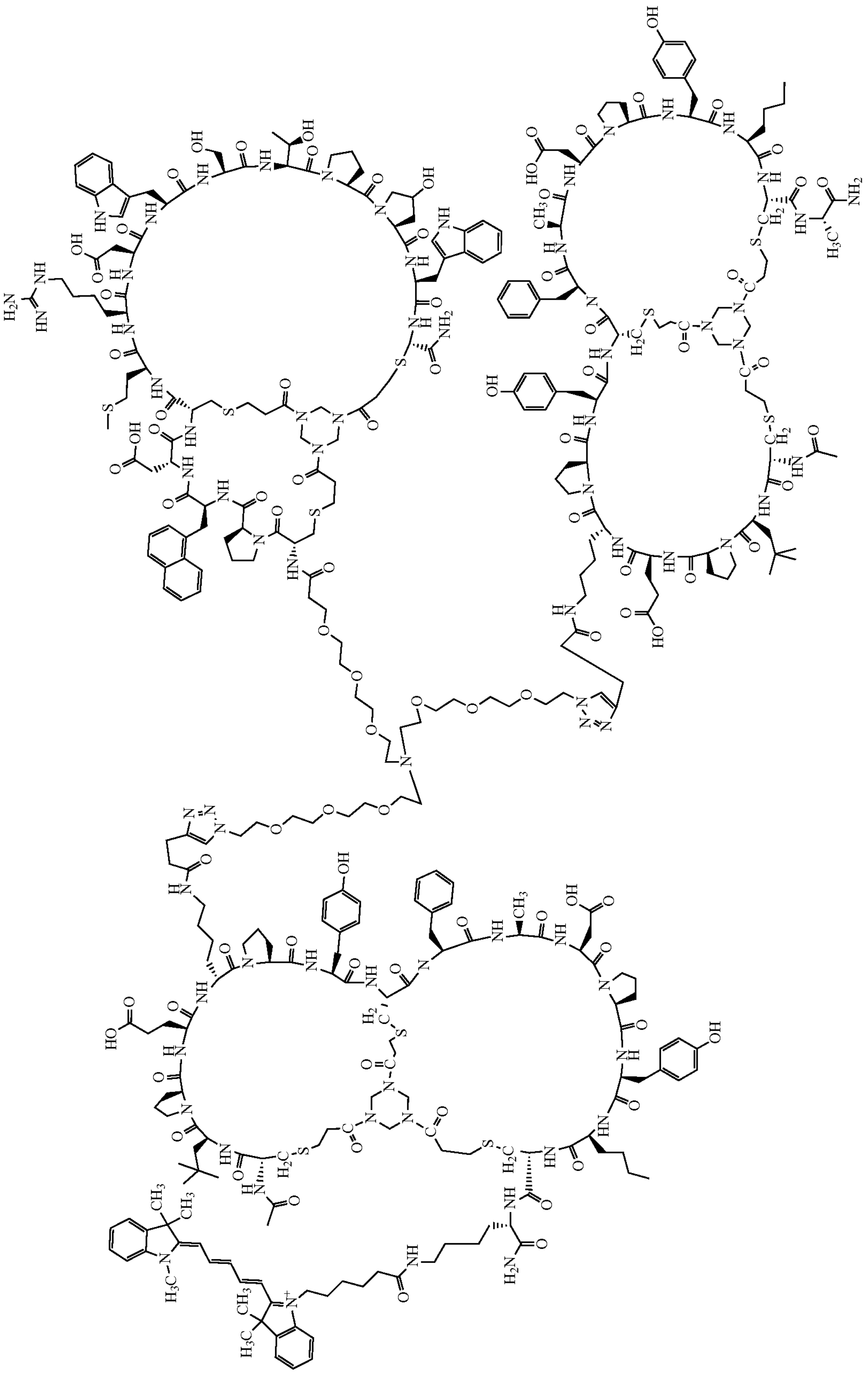
BCY13628

Procedure for Preparation of BCY13628

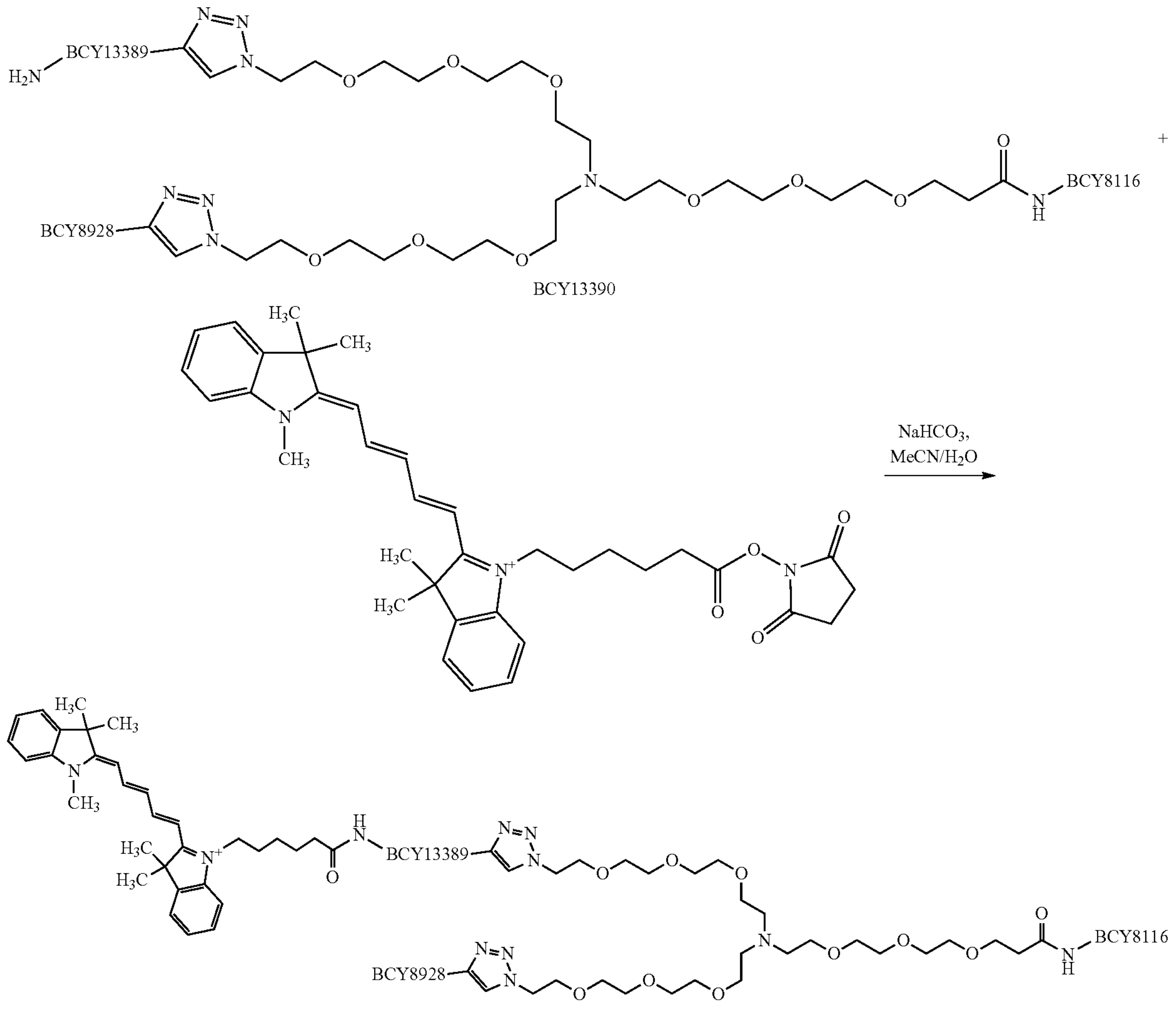

BCY13390

BCY13628

A mixture of BCY13390 (5.6 mg, 0.77 μmol, 1.0 eq) and cyanine 5 NHS ester (0.5 mg, 0.85 μmol, 1.1 eq) was dissolved in MeCN/$H_2O$ (1:1, 2 mL). The pH of this solution was adjusted to 8 by dropwise addition of 1.0 M $NaHCO_3$. The reaction mixture was stirred at 25° C. for 0.5 hr. LC-MS showed BCY13390 was consumed completely and one main peak with desired m/z was detected. The reaction mixture was filtered and concentrated under reduced pressure to give a residue. The crude product was purified by preparative HPLC, and BCY13628 (2.9 mg, 0.36 μmol, 46% yield, 95% purity) was obtained as a blue solid. Calculated MW: 7736.06, observed m/z: 1289.9 ($[M+6H]^{6+}$), 1105.5 ($[M+7H]^{7+}$).

Example 6: Synthesis of BCY15155

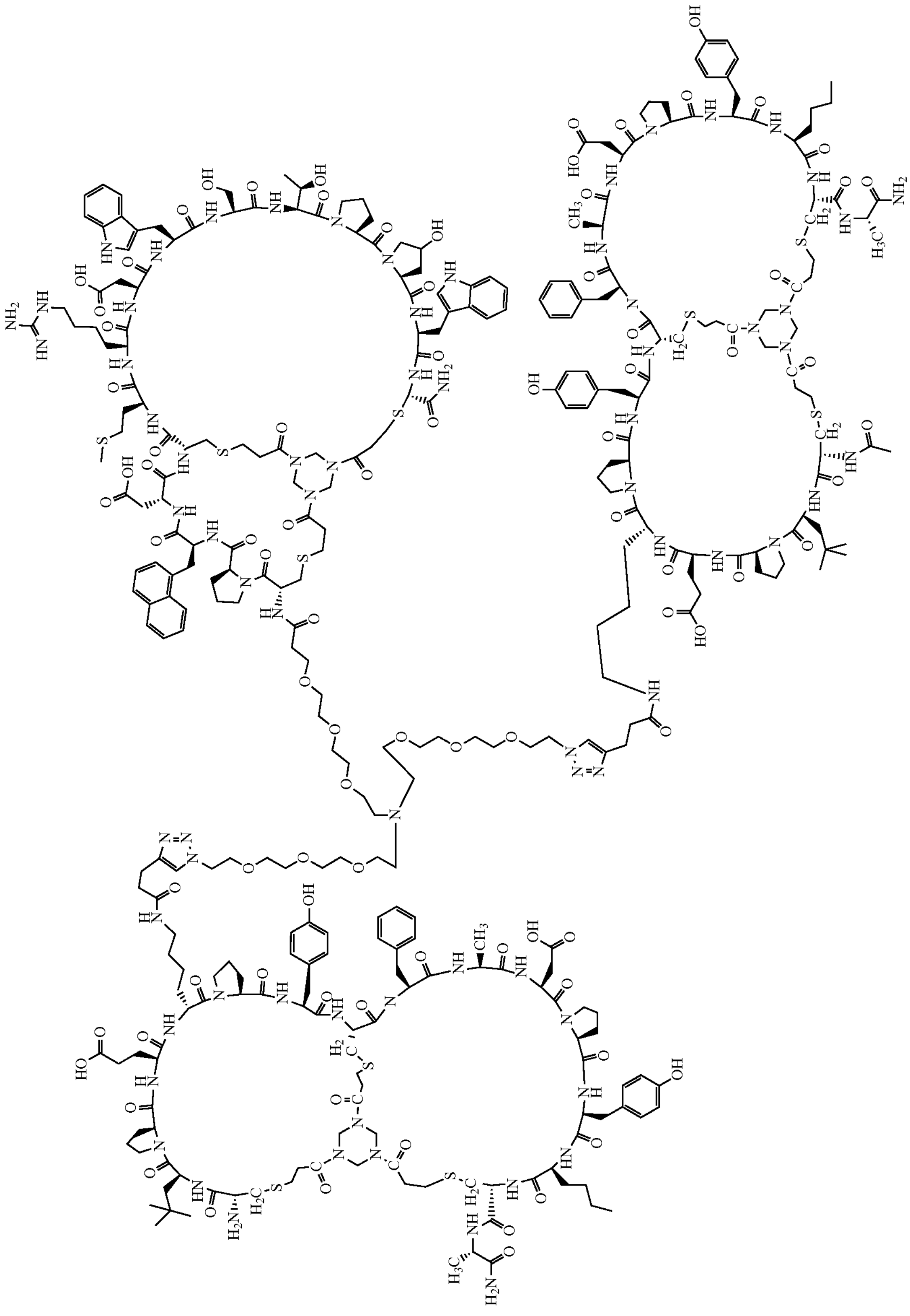
BCY15155

Procedure for Preparation of BCY15155

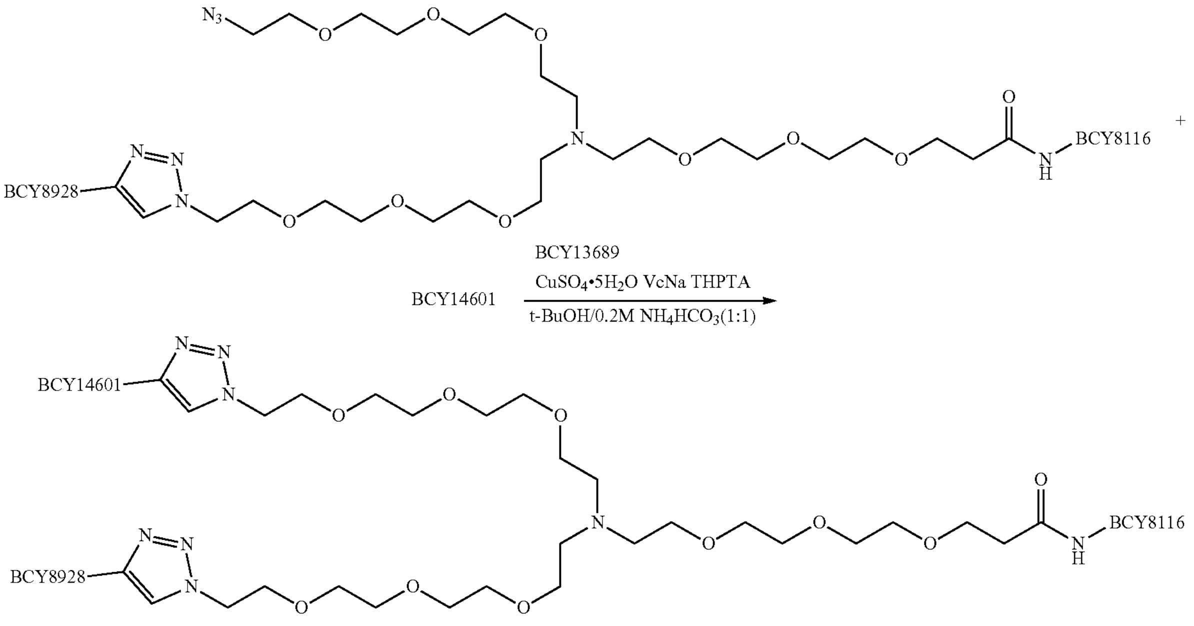

BCY15155

A mixture of BCY13689 (25.0 mg, 5.00 μmol, 1.0 eq), BCY14601 (13.0 mg, 6.01 μmol, 1.2 eq), and THPTA (2.0 mg, 5.00 μmol, 1.0 eq) was dissolved in t-BuOH/0.2 M $NH_4HCO_3$ (1:1, 0.5 mL, pre-degassed and purged with $N_2$), and then $CuSO_4$ (0.4 M, 12.5 μL, 1.0 eq) and Vc (3.5 mg, 20.02 μmol, 4.0 eq) were added under $N_2$. The pH of this solution was adjusted to 8, and the solution turned light yellow. The reaction mixture was stirred at 25° C. for 2 hr under $N_2$ atmosphere. LC-MS showed BCY13689 was consumed completely, some BCY14601 remained and one main peak with desired m/z was detected. The reaction mixture was filtered and concentrated under reduced pressure to give a residue. The crude product was purified by preparative HPLC, and BCY15155 (19.7 mg, 2.41 μmol, 36% yield, 97% purity) was obtained as a white solid. Calculated MW: 7171.3, observed m/z: 1434.7 ($[M+5H]^{5+}$), 1196.2 ($[M+6H]^{6+}$).

Example 7: Synthesis of BCY14602

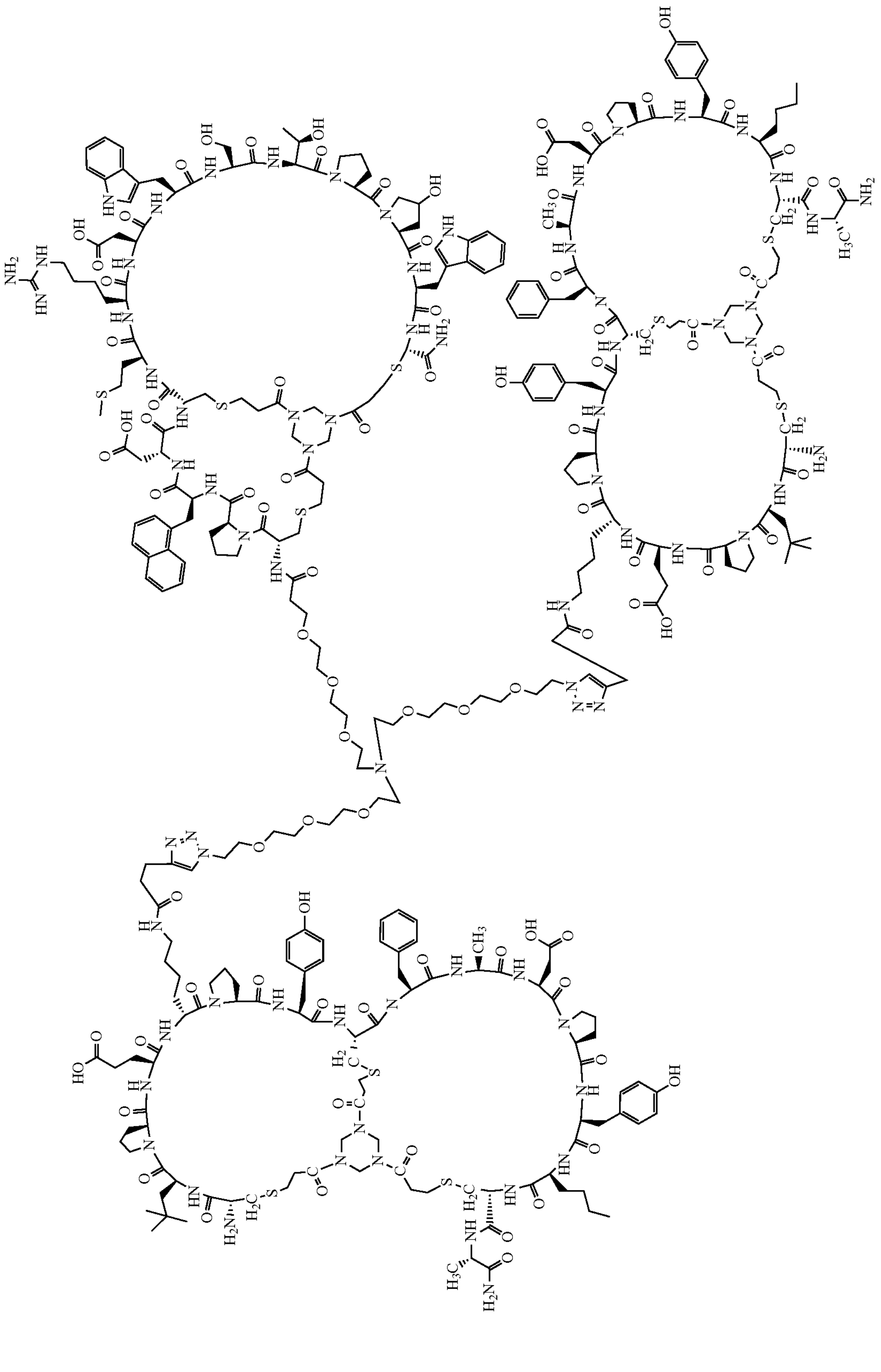
BCY14602

Procedure for Preparation of BCY14602

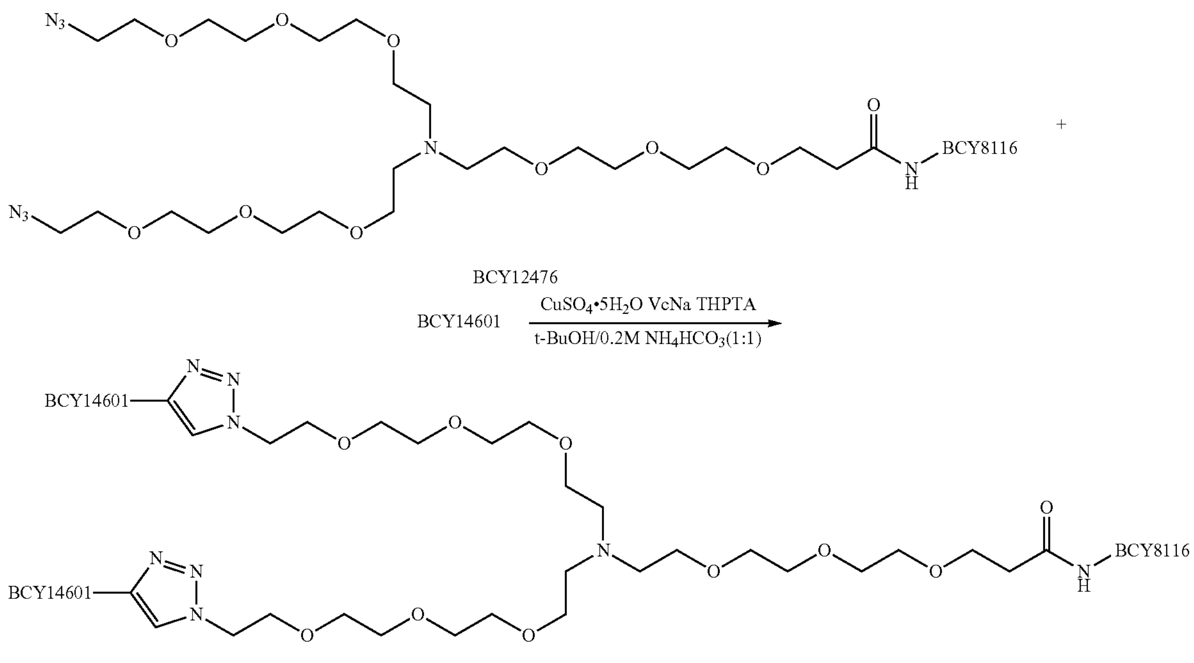

BCY14602

A mixture of BCY12476 (100.0 mg, 36.00 μmol, 1.0 eq), BCY14601 (158.0 mg, 72.63 μmol, 2.04 eq), and THPTA (15.6 mg, 36.00 μmol, 1.0 eq) was dissolved in t-BuOH/0.2 M $NH_4HCO_3$ (1:1, 2 mL, pre-degassed and purged with $N_2$), and then $CuSO_4$ (0.4 M, 89.0 μL, 1.0 eq) and VcNa (28.5 mg, 143.98 μmol, 4.0 eq) were added under $N_2$. The pH of this solution was adjusted to 8, and the solution turned light yellow. THPTA and VcNa were replenished twice, and overall the solution was stirred at 25° C. for 48 hr under $N_2$ atmosphere. LC-MS showed BCY12476 was consumed completely, BCY14601 remained and one main peak with desired m/z was detected. Some byproduct was also detected. The reaction mixture was filtered and concentrated under reduced pressure to give a residue. The crude product was purified by preparative HPLC, and BCY14602 (45.2 mg, 5.51 μmol, 15% yield, 86% purity) was obtained as a white solid. Calculated MW: 7129.2, observed m/z: 1426.6 ($[M+5H]^{5+}$), 1189.1 ($[M+6H]^{6+}$).

Analytical Data

The following heterotandem bicyclic peptide complexes of the invention were analysed using mass spectrometry and HPLC. HPLC setup was as follows:

Mobile Phase: A: 0.1% TFA in $H_2O$ B: 0.1% TFA in ACN

Flow: 1.0 ml/min

Column: Gemini-NX C18 5 um 110 A 150*4.6 mm

Instrument: Agilent 1200 HPLC-BE (1-614)

Gradients used are 30-60% B over 20 minutes and the data was generated as follows:

| Complex ID | Analytical Data - Mass Spectrometry | HPLC Retention Time (min) |
|---|---|---|
| BCY11863 | MW: 7213.32, observed m/z: 1444.0 ([M/5 + H]+) | 10.649 |

Biological Data

1. CD137 Reporter Assay Co-Culture with Tumor Cells

Culture medium, referred to as R1 media, is prepared by adding 1% FBS to RPMI-1640 (component of Promega kit CS196005). Serial dilutions of test articles in R1 are prepared in a sterile 96 well-plate. Add 25 μL per well of test articles or R1 (as a background control) to designated wells in a white cell culture plate. Tumor cells* are harvested and resuspended at a concentration of 400,000 cells/mL in R1 media. Twenty five (25) μL/well of tumor cells are added to the white cell culture plate. Jurkat cells (Promega kit CS196005, 0.5 mL) are thawed in the water bath and then added to 5 ml pre-warmed R1 media. Twenty five (25) μL/well of Jurkat cells are then added to the white cell culture plate. Incubate the cells and test articles for 6 h at 37° C., 5% $CO_2$. At the end of 6 h, add 75 L/well Bio-Glo™ reagent (Promega) and incubate for 10 min before reading luminescence in a plate reader (Clariostar, BMG). The fold change relative to cells alone (Jurkat cells+Cell line used in co-culture) is calculated and plotted in GraphPad Prism as log (agonist) vs response to determine $EC_{50}$ (nM) and Fold Induction over background (Max).

The tumor cell type used in co-culture is NCI-H292, CT26 #7, MC38 #13, HT1376, NCI-H322 and T47D which has been shown to express Nectin-4.

Data presented in FIG. 1A shows that the Nectin-4/CD137 heterotandem (BCY11863) induces strong CD137 activation in a CD137 reporter assay and the activation is dependent on the binding of the heterotandem to CD137. BCY11617, a molecule in which CD137 bicyclic peptide is comprised of all D-amino acids which abrogates binding does not induce CD137 agonism.

A summary of the $EC_{50}$ (nM) induced by heterotandem bicyclic peptide complexes BCY11863 and close analogues in a CD137 reporter assay in co-culture with a Nectin-4-expressing tumor cell line is reported in Table 1 below and visualized in FIG. 1B. This data demonstrates the potential of BCY11863 to induce CD137 agonism in coculture with cell lines that have a range of Nectin-4 expression.

TABLE 1

EC50 (nM) of Fold induction over background induced by Nectin-4/CD137 heterotandem bicyclic peptide complexes in a CD137 reporter assay

| Complex ID | Tumor cell line Species | Cell Line used in Coculture | Arithmetic mean $EC_{50}$ (nM) |
|---|---|---|---|
| BCY11863 | mouse | CT26#7 | 0.14 ± 0.07 |
| BCY11863 | mouse | MC38#13 | 0.31 ± 0.26 |
| BCY11863 | human | NCI-H292 | 0.28 ± 0.20 |
| BCY11863 | human | HT1376 | 0.52 ± 0.30 |
| BCY11863 | human | NCI-H322 | 0.33 ± 0.21 |
| BCY11863 | human | T47D | 0.42 ± 0.24 |
| BCY11863 | human | MDA-MB-468 | 0.23 ± 0.01 |
| BCY13582 | human | HT1376 | 0.58 ± 0.27 |
| BCY13582 | human | MDA-MB-468 | 0.34 ± 0.02 |
| BCY13583 | human | HT1376 | 1.7 ± 0.9 |
| BCY13583 | human | MDA-MB-468 | 0.84 ± 0.07 |

2. Human PBMC Co-Culture (Cytokine Release) Assay

Human and mouse tumor cell lines were cultured according to suppliers' recommendations. Frozen PBMCs from healthy human donors were thawed and washed one time in room temperature PBS, and then resuspended in R10 medium. 100 µl of PBMCs (1,000,000 PBMCs/ml) and 100 µl of tumor cells (100,000 tumor cells/ml) (Effector: Target cell ratio (E:T) 10:1) were plated in each well of a 96 well flat bottom plate for the co-culture assay. 100 ng/ml of soluble anti-CD3 mAb (clone OKT3) was added to the culture on day 0 to stimulate human PBMCs. Test, control compounds, or vehicle controls were diluted in R10 media and 50 µL was added to respective wells to bring the final volume per well to 250 µL. Plates were covered with a breathable film and incubated in a humidified chamber at 37° C. with 5% $CO_2$ for three days. Supernatants were collected 48 hours after stimulation, and human IL-2 and IFNγ were detected by Luminex. Briefly, the standards and samples were added to black 96 well plate. Microparticle cocktail (provided in Luminex kit, R&D Systems) was added and shaken for 2 hours at room temperature. The plate was washed 3 times using magnetic holder. Biotin cocktail was then added to the plate and shaken for 1 hour at RT. The plate was washed 3 times using magnetic holder. Streptavidin cocktail was added to the plate and shaken for 30 minutes at RT. The plates were washed 3 times using magnetic holder, resuspended in 100 µL of wash buffer, shaken for 2 minutes at RT, and read using the Luminex 2000. Raw data were analyzed using built-in Luminex software to generate standard curves and interpolate protein concentrations, all other data analyses and graphing were performed using Excel and Prism software. Data represents studies with 3-5 independent donor PBMCs tested in technical triplicates.

Data presented in FIGS. 2A and 2B demonstrate that the Nectin-4/ CD137 heterotandem (BCY11863) induces robust IL-2 and IFN-γ cytokine secretion in a PBMC-4T1 co-culture assay. BCY11617 is a negative control that binds Nectin-4 but does not bind CD137.

A summary of the $EC_{50}$ (nM) and maximum IFN-γ cytokine secretion (pg/ml) induced by selected Nectin-4/CD137 heterotandem bicyclic peptide complexes in Human PBMC co-culture (cytokine release) assay is reported in Table 2 below and visualized in FIG. 2C. This demonstrates the potential of BCY11863 to induce cytokine secretion in the presence of a number of different tumor cell lines expressing Nectin-4.

TABLE 2

$EC_{50}$ of IFN-γ cytokine secretion induced by selected Nectin-4/CD137 heterotandem bicyclic peptide complexes in Human PBMC-4T1 co-culture (cytokine release) assay

| Cell Line | IL-2 (nM) | IFNy (nM) | No. of Donors |
|---|---|---|---|
| MC38 # 13 (mouse) | 0.25 ± 0.08 | 0.17 ± 0.11 | 4 |
| 4T1-D02 (mouse) | 0.16 ± 0.22 | 0.04 ± 0.04 | 4 |
| HT1376 (human) | 0.39 ± 0.29 | 0.23 ± 0.15 | 5 |
| T-47D (human) | 0.20 ± 0.07 | 0.08 ± 0.06 | 3 |
| H322 (human) | 0.84 ± 0.15 | 0.85 ± 0.66 | 3 |
| BCY11863 | 4T1-Parental (Nectin4-) | No induction up to 100 nM | |

3. Pharmacokinetics of the Nectin-4/ CD137 Heterotandem BCY11863 in SD Rats

Male SD Rats were dosed with the Nectin-4/ CD137 heterotandem BCY11863 formulated in 25 mM Histidine HCl, 10% sucrose pH 7 by IV bolus, IV infusion (15 minutes) or subcutaneously. Serial bleeding (about 80 µL blood/time point) was performed via submandibular or saphenous vein at each time point. All blood samples were immediately transferred into prechilled microcentrifuge tubes containing 2 µL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 µL of the supernatant samples were directly injected for LC-MS/MS analysis using an Orbitrap Q Exactive in positive ion mode to determine the concentrations of analyte. Plasma concentration versus time data were analyzed by non-compartmental approaches using the Phoenix WinNonlin 6.3 software program. C0, CI, Vdss, T½, AUC(0-last), AUC(0-inf), MRT(0-last), MRT(0-inf) and graphs of plasma concentration versus time profile were reported. The pharmacokinetic parameters from the experiment are as shown in Table 3:

TABLE 3

| Pharmacokinetic Parameters in SD Rats | | | | | | |
|---|---|---|---|---|---|---|
| Compound | Dose (mg/kg) | Dosing Route | T½ (h) | Vdss (L/kg) | Clp (ml/min/kg) | % F |
| BCY11863 | 1.9 | IV Bolus | 4.1 | 1.6 | 7.7 | — |
| | 3.2 | IV Inf (15 min) | 3.1 | 1.3 | 9.3 | — |
| | 6.3 | SC | 2.5 | — | — | 95% |

Data in Table 3 above and FIG. 5 shows that BCY11863 is a low clearance molecule with volume of distribution larger than plasma volume. In addition, the bioavailability from SC dosing of BCY11863 is high in rats.

TABLE 4

| Pharmacokinetic Parameters of BCY11863 and potential metabolites in SD Rat PK study following 100 mg/kg dose administered by IV administration | | | | | |
|---|---|---|---|---|---|
| Analytes | Cmax (ng/mL) | AUC (ng · h/mL) | T½ (h) | Vdss (L/kg) | Clp (ml/min/kg) |
| BCY11863 | 279540 | 129863 | 5.4 | 2.3 | 13 |
| BCY15155 | 2854 | 1296 | 3.1 | — | — |
| BCY14602 | — | — | — | — | — |

Data in Table 4 and FIG. 14 shows that <1% of BCY11863 gets metabolized to BCY15155 upon IV administration of BCY11863 to SD rats. No significant conversion to BCY14602 is noted during the first 24 h of the study.

4. Pharmacokinetics of the Nectin-4/ CD137 Heterotandem BCY11863 in Cynomolgus Monkey Non-naïve Cynomolgus Monkeys were dosed via intravenous infusion (15 or 30 min) into the cephalic vein with 1 mg/kg of the Nectin-4/ CD137 heterotandem BCY11863 formulated in 25 mM Histidine HCl, 10% sucrose pH 7. Serial bleeding (about 1.2 ml blood/time point) was performed from a peripheral vessel from restrained, non-sedated animals at each time point into a commercially available tube containing potassium (K2) EDTA*$2H_2O$ (0.85-1.15 mg) on wet ice and processed for plasma. Samples were centrifuged (3,000×g for 10 minutes at 2 to 8° C.) immediately after collection. 0.1 mL plasma was transferred into labelled polypropylene micro-centrifuge tubes. 5-fold of the precipitant including internal standard 100 ng/ml Labetalol & 100 ng/ml dexamethasone & 100 ng/ml tolbutamide & 100 ng/ml Verapamil & 100 ng/ml Glyburide & 100 ng/ml Celecoxib in MeOH was immediately added into the plasma, mixed well and centrifuged at 12,000 rpm for 10 minutes at 2 to 8° C. Samples of supernatant were transferred into the pre-labeled polypropylene microcentrifuge tubes, and frozen over dry ice. The samples were stored at-60° C. or below until LC-MS/MS analysis. An aliquot of 40 μL calibration standard, quality control, single blank and double blank samples were added to the 1.5 ml tube. Each sample (except the double blank) was quenched with 200 μL IS1 respectively (double blank sample was quenched with 200 μL MeOH with 0.5% tritonX-100), and then the mixture was vortex-mixed well (at least 15 s) with vortexer and centrifuged for 15 min at 12000 g, 4° C. A 10 μL supernatant was injected for LC-MS/MS analysis using an Orbitrap Q Exactive in positive ion mode to determine the concentrations of analyte. Plasma concentration versus time data were analyzed by non-compartmental approaches using the Phoenix WinNonlin 6.3 software program. C0, CI, Vdss, T½, AUC(0-last), AUC(0-inf), MRT(0-last), MRT(0-inf) and graphs of plasma concentration versus time profile were reported. The pharmacokinetic parameters for two bispecific compounds are as shown in Table 5.

TABLE 5

| Pharmacokinetic Parameters in cynomolgous monkey | | | | | |
|---|---|---|---|---|---|
| Compound | Dose (mg/kg) | Route | $T_{1/2}$ (h) | Clp (ml/min/kg) | Vdss (L/kg) |
| BCY11863 | 0.93 | IV infusion (30 min) | 5.3 | 3.3 | 0.62 |
| | 0.97 | IV infusion (15 min) | 4.5 | 4.8 | 0.91 |
| | 9.4 | IV infusion (15 min) | 8.9 | 3.9 | 1.1 |

FIG. 3 shows the plasma concentration vs time curve of BCY11863 from a 2 mg/kg IV dose in SD Rat (n=3) and 1 mg/kg IV infusion in cynomolgus monkey (n=2). BCY11863 has a volume of distribution at steady state (Vdss) of 1.6 L/kg and a clearance of 7.7 mL/min/kg in rats which results in a terminal half life of 4.1 h. BCY11863 has a volume of distribution at steady state (Vdss) of 0.62 L/kg and a clearance of 3.3 mL/min/kg in cyno which results in a terminal half life of 5.3 h. Subsequent studies are consistent with these results. The PK parameters from the IV study in cyno indicates that this is a low plasma clearance molecule with volume of distribution similar to total body water.

5. Pharmacokinetics of the Nectin-4/ CD137 Heterotandem BCY11863 in CD1 Mice

6 Male CD-1 mice were dosed with 15 mg/kg of the Nectin-4/ CD137 heterotandem BCY11863 formulated in 25 mM Histidine HCl, 10% sucrose pH 7 via intraperitoneal or intravenous administration. Serial bleeding (about 80 μL blood/time point) was performed via submandibular or saphenous vein at each time point. All blood samples were immediately transferred into prechilled microcentrifuge tubes containing 2 μL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 μL of the supernatant samples were directly injected for LC-MS/MS analysis using an Orbitrap Q Exactive in positive ion mode to determine the concentrations of analyte. Plasma concentration versus time data were analyzed by non-compartmental approaches using the Phoenix WinNonlin 6.3 software program. C0, CI, Vdss, T½, AUC(0-last), AUC(0-inf), MRT(0-last), MRT(0-inf) and graphs of plasma concentration versus time profile were reported.

FIG. 9 shows the plasma concentration vs time curves of BCY11863 from a 15 mg/kg IP dose in CD1 mice (n=3) and the terminal plasma half life for BCY11863.

TABLE 6

| Pharmacokinetic Parameters in CD-1 Mice | | | | | | |
|---|---|---|---|---|---|---|
| Compound | Dose (mg/kg) | Dosing Route | T½ (h) | Vdss (L/kg) | Clp (ml/min/kg) | % F |
| BCY11863 | 5.6 | IV Bolus | 2.6 | 1.6 | 9.7 | |
| | 0.96 | IV Bolus | 1.7 | 2.9 | 21 | |

TABLE 6-continued

| Pharmacokinetic Parameters in CD-1 Mice | | | | | | |
|---|---|---|---|---|---|---|
| Compound | Dose (mg/kg) | Dosing Route | T½ (h) | Vdss (L/kg) | Clp (ml/min/kg) | % F |
| | 12 | IV Bolus | 2.6 | 2.5 | 17 | |
| | 32 | IV Bolus | 2.4 | 2.1 | 16 | |
| | 15.5 | IP | 2.5 | — | — | 100 |

Data in FIG. 9 and Table 6 above shows BCY11863 can be dosed as IV bolus and IP in mice. The bioavailability from IP dosing of BCY11863 is high in mice. The PK parameters from the IV study indicates that this is a low clearance molecule with volume of distribution larger than plasma volume.

6. Anti-Tumor Activity of BCY11863 in a Syngeneic Nectin-4 Overexpressing MC38 Tumor Model (MC38#13)

6-8 weeks old C57BL/6J-hCD137 female mice were inoculated in the flank with $1\times10^6$ syngeneic Nectin-4 overexpressing MC38 cells (MC38#13). When tumors reached 72 $mm^3$ size on average, mice were randomized to receive vehicle or BCY11863 (intraperitoneal administration). BCY11863 was administered (n=6 mice/treatment cohort) at either 1 mg/kg or 10 mg/kg either daily (QD) or every three days (Q3D). QD dosed mice received 16 doses of BCY11863 and Q3D dosed mice received 10 doses of BCY11863. Tumor growth was monitored by caliper measurements until day 69 after treatment initiation. The results of this experiment may be seen in FIG. 4 where significant reduction ($p<0.05$, 2-way ANOVA with Dunnett's test for multiple comparisons) of tumor growth was observed in 2 treatment cohorts by day 7 and by day 14 all treatment groups were significantly different from the vehicle group. By day 48, 22 out of 24 BCY11863-treated animals had responded to the treatment completely and had no palpable tumors remaining.

Based on the circulating plasma half-life of BCY11863 in mice after IP injection (2.5 h), plasma trough levels will be close to 0 after both BCY11863 doses (1 and 10 mg/kg) and dosing intervals (QD and Q3D) thus demonstrating that less than continuous plasma exposure of BCY11863 from intermittent dosing is sufficient to lead to significant anti-tumor activity leading to durable complete responses.

7. BCY11863 Treatment Leads to an Immunogenic Memory to Nectin-4 Overexpressing MC38 Tumor Model On day 69, 5 animals that had responded completely to BCY11863 treatment were re-inoculated with $1\times10^6$ MC38#13-cells. A cohort of 5 naïve C57BL/6J-hCD137 female mice were inoculated with $1\times10^6$ MC38#13-cells as a control. The results of this experiment may be seen in FIG. 5 where all 5 inoculated naïve C57BL/6J-hCD137 female mice grew tumors by day 13 after inoculation whereas none of the inoculated complete responder mice developed tumors. This demonstrates that animals that achieved a complete antitumor response as a result of BCY11863 treatment have developed immunogenic memory.

8. BCY11863 Demonstrates Anti-Tumor Activity in a Syngeneic Nectin-4 Overexpressing CT26 Tumor Model (CT26#7)

6-8 weeks old BALB/c-hCD137 female mice were inoculated in the flank with $3\times10^5$ syngeneic Nectin-4 overexpressing CT26 cells (CT26#7). When tumors reached around 70 $mm^3$ size on average, mice were randomized to receive vehicle or 5 mg/kg BCY11863 intraperitoneally every three days (6 doses total). Tumor growth was monitored by caliper measurements until day 14 after treatment initiation. The results of this experiment may be seen in FIG. 6 where BCY11863 treatment significantly ($p<0.0001$, Student's t-test) reduced the tumor growth from day 7 forward.

Based on the circulating plasma half-life of BCY11863 in mice at IP injection (2.5 h), plasma exposure will not be continuous throughout the dosing period demonstrating that less than continuous plasma exposure of BCY11863 is sufficient to lead to significant anti-tumor activity.

9. Total T Cells and CD8+ T Cells Increase in CT26#7 Tumor Tissue 1 h After the Last (6th) Q3D dose of BCY11863

1 hour after the last vehicle or BCY11863 dose the CD26#7 bearing mice were sacrificed and tumors were harvested, processed for single cell suspensions and stained for flow cytometry analysis for total T cells (CD45+CD3+), CD8+ T cells (CD45+CD3+CD8+), CD4+ T cells (CD45+CD3+CD4+) and regulatory T cells (Tregs; CD45+CD3+CD4+Foxp3+). The results of this experiment may be seen in FIG. 7 where it can be seen that BCY11863 treatment led to significant increase of total T cells ($p<0.0001$, Student's t-test) and CD8+ T cells ($p<0.0001$, Student's t-test) as well as to a significant increase in the CD8+ T cell/Treg ratio ($p<0.05$, Student's t-test).

This demonstrates that treatment with BCY11863 can lead to an increased level of T-cells locally in the tumor tissue after intermittent dosing.

10. Pharmacokinetic Profiles of BCY11863 in Plasma and Tumor Tissue of CT26#7 Syngeneic Tumor Bearing Animals After a Single Intravenous (iv) Administration of 5 mg/kg of BCY11863

6-8 weeks old BALB/c female mice were inoculated in the flank with $3\times10^5$ syngeneic Nectin-4 overexpressing CT26 cells (CT26#7). When tumors reached around 400 $mm^3$ size on average, mice were randomized to receive a single intravenous dose of vehicle or 5 mg/kg BCY11863. A cohort of mice (n=3/ timepoint) were sacrificed at 0.25, 0.5, 1, 2, 4, 8 and 24 h timepoints and harvested plasma and tumor tissue were analyzed for BCY11863. For tumor BCY11863 content analysis, tumor homogenate was prepared by homogenizing tumor tissue with 10 volumes (w:v) of homogenizing solution (MeOH/15 mM PBS (1:2, v:v)). 40 μL of sample was quenched with 200 μL IS1 and the mixture was mixed by vortexing for 10 min at 800 rpm and centrifuged for 15 min at 3220 g at 4° C. The supernatant was transfer to another clean 96-well plate and centrifuged for 5 min at 3220 g at 4° C., and 10.0 μL of supernatant was then injected for LC-MS/MS analysis using an Orbitrap Q Exactive in positive ion mode to determine the concentrations of analyte. For plasma BCY11863 content analysis, blood samples were collected in K2-EDTA tubes and immediately processed to plasma by centrifugation at approximately 4° C., 3000 g. 40 μL of plasma sample was quenched with 200 μL IS1 and the mixture was mixed by vortexing for 10 min at 800 rpm and centrifuged for 15 min at 3220 g at 4° C. The supernatant was transferred to another clean 96-well plate and centrifuged for 5 min at 3220 g at 4° C., and 10.0 μL of supernatant was then injected for LC-MS/MS analysis using an Orbitrap Q Exactive in positive ion mode to determine the concentrations of analyte.

The results of this experiment are shown in FIG. 8 where it can be seen that BCY11863 was retained in the tumor tissue after the plasma BCY11863 is eliminated from circulation as indicated by the difference of BCY11863 plasma $T_{1/2}$ (1.65 h) and tumor $T_{1/2}$ (13.4 h).

11. Binding of BCY11863 to Nectin-4 and CD137 Across Four Preclinical Species

The binding of BCY11863 to its primary target Nectin-4 and CD137 was characterized using surface plasmon resonance (SPR).

(a) Nectin-4

BCY11863 binds to cyno, rat, mouse and human Nectin-4 with $K_D$ between 5-27 nM as measured by direct binding to the extracellular domain that has been biotinylated and captured on a streptavidin sensor chip surface.

TABLE 7

Binding affinities of BCY11863 to Biotinylated-Nectin-4 extracellular domain: SPR data

| SPR $K_D$ (nM) | Assay Type | Human (25° C.) | Human (37° C.) | NHP (25° C.) | Rat (25° C.) | Mouse (25° C.) |
|---|---|---|---|---|---|---|
| BCY11863 | Direct Binding | 5.0 ± 2.1 n = 7 | 5.2 ± 1.1 n = 9 | 27 ± 15 n = 9 | 15 ± 1 n = 6 | 4.6 ± 2.1 n = 9 |

To understand whether the binding of BCY11863 to Nectin-4 was altered in the context of the ternary complex, i.e. when also bound to CD137, a multicomponent SPR binding assay was developed. BCY11863 was first captured to human CD137 immobilized on the SPR chip surface and then Nectin-4 from different species were passed over the chip to determine their affinities to the captured BCY11863 (see FIG. 10C). The affinities to Nectin-4 were generally maintained in the presence of CD137 binding as shown below:

TABLE 8

Binding affinities of BCY11863 to Nectin-4 extracellular domain using biotinylated human CD137 as capture reagent

| SPR $K_D$ (nM) | Assay Type | Human | NHP | Rat | Mouse |
|---|---|---|---|---|---|
| BCY11863 | Sandwich Assay | 12 ± 2 n = 4 | 28 ± 5 n = 3 | 25 ± 2 n = 3 | 6.7 ± 1.7 n = 3 |

(b) CD137

Direct binding of BCY11863 to surface bound CD137 cannot be measured accurately by SPR because of avidity resulting from two CD137 binding bicycles in BCY11863 which leads to extremely slow $k_{off}$ (See FIG. 10B). In addition, biotinylation of cyno CD137 abrogates binding of BCY11863, likely due to modification of a lysine on the cyno protein that is important for BCY11863 binding. Hence, a BCY11863 analogue containing a C-terminal biotinylated lysine (BCY13582) was tested in SPR to determine cross species specificity of BCY11863. BCY13582 was captured to the sensor chip using a reversible biotin capture kit and the affinities to Nectin-4 from different species were determined. Both strategies showed that these BCY11863 analogs bound to human and cyno CD137 with $K_D$<10 nM and had negligible binding to both mouse and rat CD137.

TABLE 9

Binding affinities of biotinylated BCY11863 analogues to CD137 extracellular domain: SPR data

| SPR $K_D$ (nM) | Assay Type | Human | NHP | Rat | Mouse |
|---|---|---|---|---|---|
| BCY13582 | Direct Binding | 8.4 ± 4.2 n = 3 | 4.23 n = 1 | NB n = 1 | NB n = 1 |

To understand whether the binding of BCY11863 to CD137 was altered in the context of the ternary complex, i.e. when also bound to Nectin-4, a dual binding SPR binding assay was developed. BCY11863 was first captured to human Nectin-4 immobilized on the SPR chip surface and then soluble CD137 from different species were passed over the chip to determine their affinities to the captured BCY11863 (see FIG. 10D). The affinities to CD137 were generally maintained in the presence of Nectin-4 binding as shown below:

TABLE 10

Binding affinities of BCY11863 to CD137 ECD using biotinylated human Nectin-4 as capture reagent

| SPR $K_D$ (nM) | Assay Type | Human | NHP | Rat | Mouse |
|---|---|---|---|---|---|
| BCY11863 | Dual Binding | 6.3 ± 0.7 n = 4 | 18 ± 6 n = 3 | NB n = 2 | NB n = 2 |

FIG. 10A shows one example sensorgram which demonstrates that BCY11863 binds to Nectin-4 (human) with an affinity of 4.1 nM. FIG. 10B shows the sensorgram that BCY11863 binds to CD137 (human) with high affinity. Due to the presence of 2 CD137 binding bicycles in BCY11863, the off rate from immobilized CD137 protein is very slow and the reported $K_D$ may be an overestimation (FIG. 10B). FIG. 10C shows BCY11863 binds to Nectin-4 while the CD137 arms are bound to CD137 protein immobilized on the chip to form a ternary complex. FIG. 10D shows BCY11863 binds to CD137 while the Nectin-4 binding arm is bound to Nectin-4 protein immobilized on the chip to form a ternary complex. FIG. 10E demonstrates the ability of BCY13582 immobilized on SPR chip to bind human CD137.

12. Selectivity of BCY11863 for Nectin-4 and CD137

Nectin-4 Paralogue screening: Binding of BCY11863 was assessed using SPR against Nectin-1 (2880-N1, R&D Systems), Nectin-2 (2229-N2, R&D Systems), Nectin-3 (3064-N3, R&D Systems), Nectin-like-1 (3678-S4-050, R&D Systems), Nectin-like-2 (3519-S4-050, R&D Systems), Nectin-like-3 (4290-S4-050, R&D Systems), Nectin-like-4 (4164-S4, R&D Systems) and Nectin-like-5 (2530-CD-050, R&D Systems) by labelling them with biotin and immobilizing them on a streptavidin surface. BCY11863 did not show any binding to these targets up to a concentration of 5000 nM.

CD137 Paralogue screening: Binding of streptavidin captured BCY13582 (biotinylated-BCY11863) was assessed using SPR against soluble TNF family receptors OX40 and CD40. BCY13582 did not bind to these targets up to a concentration of 100 nM.

Retrogenix microarray screening: Retrogenix's cell microarray technology was used to screen for specific off-target binding interactions of a biotinylated BCY11863 known as BCY13582.

Investigation of the levels of binding of the test peptide to fixed, untransfected HEK293 cells, and to cells over-expressing Nectin-4 and CD137 (TNFRSF9), showed 1 μM of the test peptide to be a suitable screening concentration. Under these conditions, the test peptide was screened for binding against human HEK293 cells, individually expressing 5484 full-length human plasma membrane proteins and secreted proteins. This revealed 9 primary hits, including Nectin-4 and CD137.

Each primary hit was re-expressed, along with two control receptors (TGFBR2 and EGFR), and re-tested with 1 μM BCY13582 test peptide, 1 μM BCY13582 test peptide in the presence of 100 μM BCY11863, and other positive and negative control treatments (FIG. 4). After removing non-specific, non-reproducible and non-significant hits, there remained three specific interactions for the test peptide. These were untethered and tethered forms of Nectin-4, and CD137—the primary targets.

No specific off-target interactions were identified for BCY13582, indicating high specificity for its primary targets.

13. Anti-Tumor Activity of BCY11863 in a Syngeneic Nectin-4 Overexpressing MC38 Tumor Model (MC38#13) on Dosing on Twice a Week at 5 mg/kg at 0, 24 h and 10 mg/kg at 0 h 6-8 week old female C57BL/6J-hCD137 mice [B-hTNFRSF9 (CD137) mice; Biocytogen] were implanted subcutaneously with $1\times10^6$ MC38#13 (MC38 cells engineered to overexpress murine Nectin-4) cells. Mice were randomized into treatment groups (n=6/ cohort) when average tumor volumes reached around 95 $mm^3$ and were treated with a weekly dose of vehicle (25 mM histidine, 10% sucrose, pH7) or 10 mg/kg BCY11863 with two different dosing schedules for two dosing cycles (5 mg/kg BCY11863 at 0 h and 24 h on D0 and D7, or 10 mg/kg at 0 h on D0 and D7). All treatments were administered intravenously (IV). Tumor growth was monitored until Day 15 from treatment initiation.

BCY11863 leads to significant anti-tumor activity with both dosing schedules, but the dose schedule with 5 mg/kg dosing at 0 h and 24 h was superior to 10 mg/kg dosing at 0 h when complete responses were analyzed on day 15 after treatment initiation (FIG. 12). 5 mg/kg BCY11863 at 0 h and 24 h on D0 and D7 dosing led to 4 out of 6 complete tumor responses whereas 10 mg/kg BCY11863 at 0 h on D0 and D7 dosing led to one out of 6 complete tumor responses. These data together with the BCY11863 mouse plasma PK data indicate that maintaining a BCY11863 plasma exposure at the level produced by 5 mg/kg 0 h and 24 h dosing in a weekly cycle produces close to complete anti-tumor response in the MC38#13 tumor model.

14. Anti-Tumor Activity of BCY11863 in a Syngeneic Nectin-4 Overexpressing MC38 Tumor Model (MC38#13)

At 3 weekly doses of 3, 10 and 30 mg/kg with dose fractionated weekly, biweekly and daily 6-8 week old female C57BL/6J-hCD137 mice [B-hTNFRSF9 (CD137) mice; Biocytogen] were implanted subcutaneously with $1\times10^6$ MC38#13 (MC38 cells engineered to overexpress murine Nectin-4) cells. Mice were randomized into treatment groups (n=6/ cohort) when average tumor volumes reached around 107 $mm^3$ and were treated with 21 daily doses of vehicle (25 mM histidine, 10% sucrose, pH7). BCY11863 treatment was done at three different total dose levels (3, 10 and 30 mg/kg total weekly dose) fractionated in three different schedules (QD: daily; BIW: twice a week or QW: weekly). Different BCY11863 treatment cohorts received either 21 daily doses (0.43, 1.4 or 4.3 mg/kg), 6 twice weekly doses (1.5, 5 or 15 mg/kg) or 3 weekly doses (3, 10 or 30 mg/kg). All treatments were administered intravenously (IV). Tumor growth was monitored until tumor reached volumes over 2000 $mm^3$ or until 31 days after treatment initiation. Complete responders (animals with no palpable tumors) were followed until D52.

BCY11863 leads to significant anti-tumor activity with many of the dosing schedules the BIW dosing schedule being the most efficacious schedule, the 5 mg/kg BIW dose in particular. This is demonstrated by the number of complete responder animals on day 52. On day 52 after treatment initiation, 15/18 mice treated BIW with BCY11863 were complete responders, 12/18 mice treated QD with BCY11863 were complete responders and 6/18 mice treated QW with BCY11863 were complete responders. 5 mg/kg BIW dosing lead to 100% complete response rate with 6/6 CRs (FIG. 13). These data together with the BCY11863 mouse plasma PK data indicate that continuous BCY11863 plasma exposure is not needed for anti-tumor response to BCY11863 in the MC38#13 tumor model.

The invention claimed is:

1. A method of synthesizing compound BCY11863:

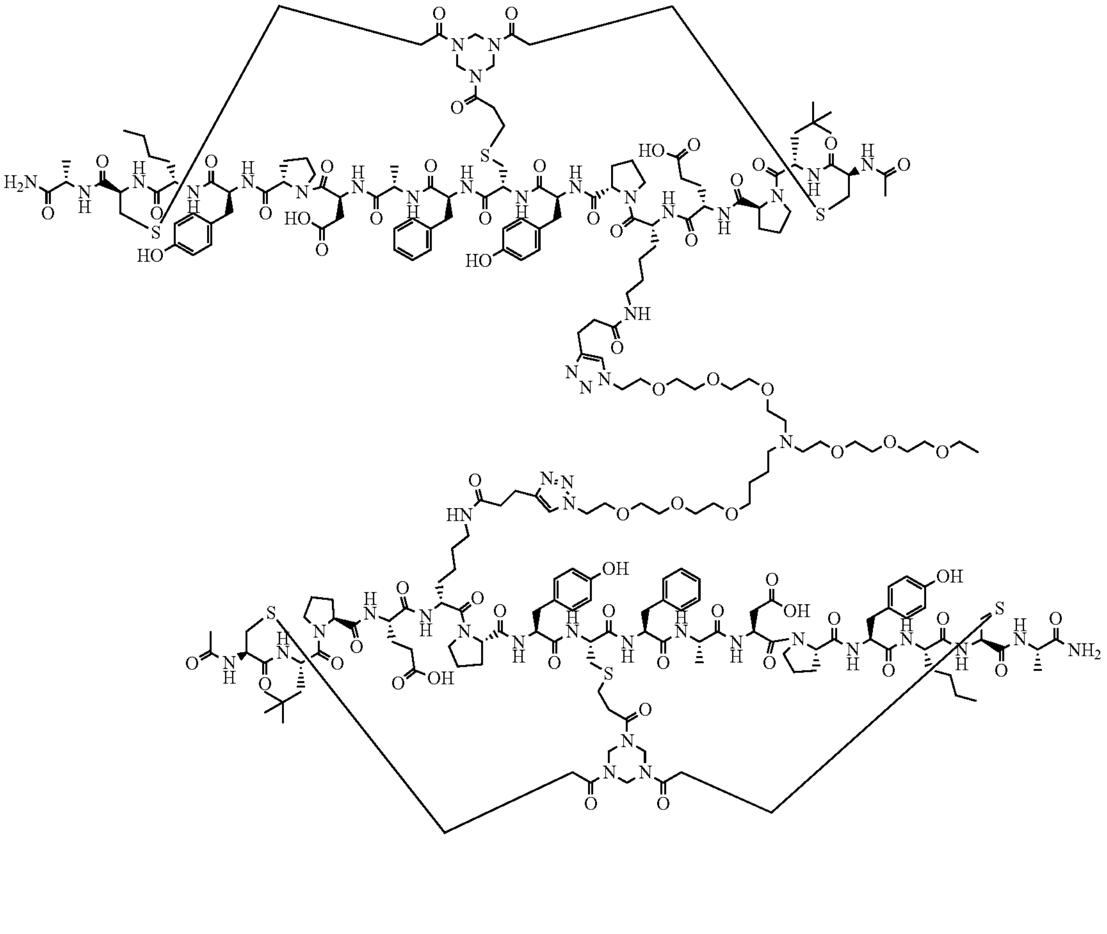

-continued

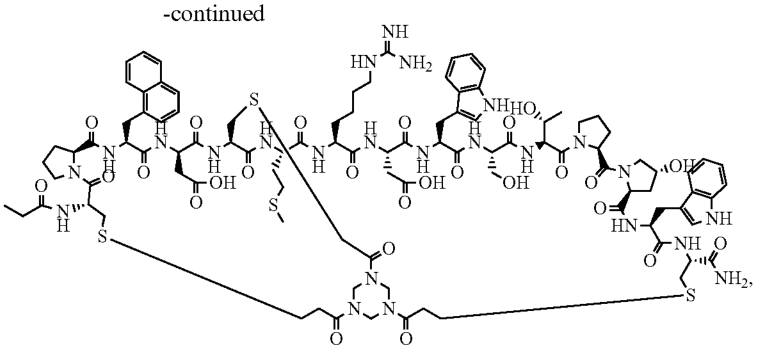

BCY00011863 or a salt thereof, comprising:

a step of reacting compound BCY12476 or a salt thereof with BCY8928 or a salt thereof;

wherein BCY12476 is a compound of formula:

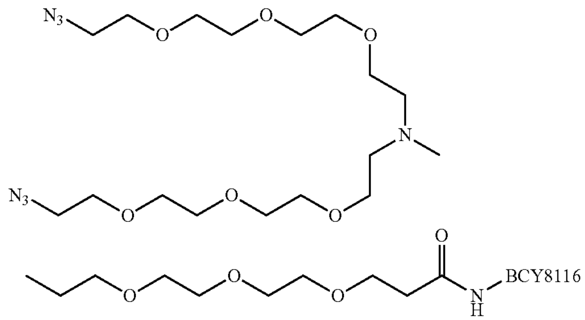

BCY12476 wherein BCY8116 is a peptide ligand which comprises a polypeptide having amino acid sequence:

(SEQ ID NO: 1)
$C_i$P[1Nal][dD]$C_{ii}$M[HArg]DWSTP[HyP]W$C_{iii}$, wherein the three reactive cysteine groups ($C_i$, $C_{ii}$ and $C_{iii}$) are separated by two loop sequences, and wherein the peptide ligand further comprises a molecular scaffold which is 1,1',1"-(1,3,5-triazinane-1,3,5-triyl) triprop-2-en-1-one (TATA) and which forms covalent bonds with the reactive cysteine groups of the polypeptide such that two polypeptide loops are formed on the molecular scaffold; or a salt thereof;

wherein BCY8928 is a peptide ligand which comprises a polypeptide having amino acid sequence:

(SEQ ID NO: 2)
Ac-$C_i$[tBuAla]PE[D-Lys(PYA)]PY$C_{ii}$FADPY[Nle]$C_{iii}$-A, wherein the three reactive cysteine groups ($C_i$, $C_{ii}$ and $C_{iii}$) are separated by two loop sequences, and wherein the peptide ligand further comprises a molecular scaffold which is 1,1',1"-(1,3,5-triazinane-1,3,5-triyl) triprop-2-en-1-one (TATA) and which forms covalent bonds with the reactive cysteine groups of the polypeptide such that two polypeptide loops are formed on the molecular scaffold, or a salt thereof, wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

2. The method of claim 1, further comprising:

a step of reacting BCY8116, or a salt thereof, with an N-(acid-PEG3)-N-bis(PEG3-azide) linker of formula:

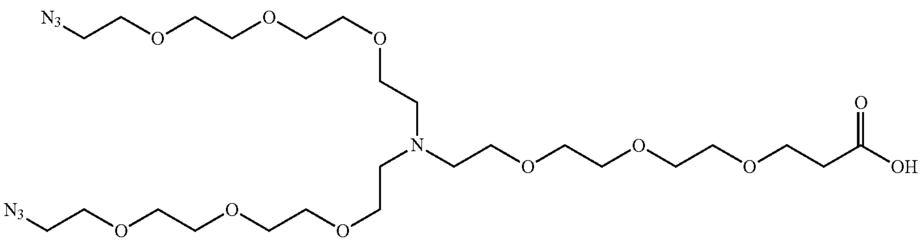 [SMILES: [N-]=[N+]=NCCOCCOCCOCCN(CCOCCOCCOCCN=[N+]=[N-])CCOCCOCCOCCC(=O)O]

or a salt thereof;

thereby forming compound BCY12476, or a salt thereof.

3. The method of claim 1, comprising reacting compound BCY12476 or a salt thereof, with BCY8928 or a salt thereof, in the presence of an azide-alkyne cycloaddition catalyst.

4. The method of claim 3, wherein the azide-alkyne cycloaddition catalyst comprises $CuSO_4$.

5. The method of claim 1, comprising reacting compound BCY12476 or a salt thereof, with BCY8928 or a salt thereof, in the presence of sodium ascorbate (VcNa).

6. The method of claim 1, comprising reacting compound BCY12476 or a salt thereof, with BCY8928 or a salt thereof, in the presence of Tris((1-hydroxy-propyl-1H-1,2,3-triazol-4-yl)methyl)amine (THPTA).

7. The method of claim 1, comprising reacting compound BCY12476 or a salt thereof, with BCY8928 or a salt thereof, in the presence of t-BuOH, $H_2O$, and/or $NH_4HCO_3$.

8. The method of claim 1, comprising reacting compound BCY12476 or a salt thereof, with BCY8928 or a salt thereof, at about pH 8.

9. The method of claim 1, comprising reacting compound BCY12476 or a salt thereof, with BCY8928 or a salt thereof, under an inert atmosphere.

10. The method of claim 1, comprising reacting compound BCY12476 or a salt thereof, with BCY8928 or a salt thereof, at about 40° C.

11. The method of claim 1, comprising reacting compound BCY12476 or a salt thereof, with BCY8928 or a salt thereof, in a reaction mixture comprising $CuSO_4$, sodium ascorbate (VcNa), Tris((1-hydroxy-propyl-1H-1,2,3-triazol-4-yl)methyl)amine (THPTA), t-BuOH, $H_2O$, and $NH_4HCO_3$;

wherein the reaction mixture is at about pH 8;

wherein the method is carried out under an $N_2$ atmosphere; and wherein the method is carried out at about 40° C.

12. The method of claim 1, further comprising purifying compound BCY11863 or a salt thereof by HPLC.

13. The method of claim 1, wherein said method is a method of providing a trifluoroacetate (TFA) salt of compound BCY11863.

14. The method of claim 2, comprising reacting BCY8116 or a salt thereof, with the N-(acid-$PEG_3$)-N-bis($PEG_3$-azide) linker in the presence of a coupling agent.

15. The method of claim 2, comprising reacting BCY8116 or a salt thereof, with the N-(acid-$PEG_3$)-N-bis($PEG_3$-azide) linker in the presence of a base.

16. The method of claim 2, comprising reacting BCY8116 or a salt thereof, with the N-(acid-$PEG_3$)-N-bis($PEG_3$-azide) linker, in the presence of a solvent.

17. The method of claim 2, comprising reacting BCY8116 or a salt thereof, with the N-(acid-$PEG_3$)-N-bis($PEG_3$-azide) linker, at about 40° C.

18. The method of claim 2, further comprising purifying compound BCY12476 or a salt thereof by HPLC.

19. The method of claim 2, comprising reacting BCY8116 or a salt thereof, with the N-(acid-$PEG_3$)-N-bis($PEG_3$-azide) linker in a reaction mixture comprising Hexafluorophosphate Azabenzotriazole Tetramethyl Uronium (HATU), N,N-diisopropylethylamine (DIEA), and Dimethylformamide (DMF);

wherein the method is carried out at about 40° C.

20. A method of synthesizing compound BCY11863, or a salt thereof, the method comprising following reaction steps:

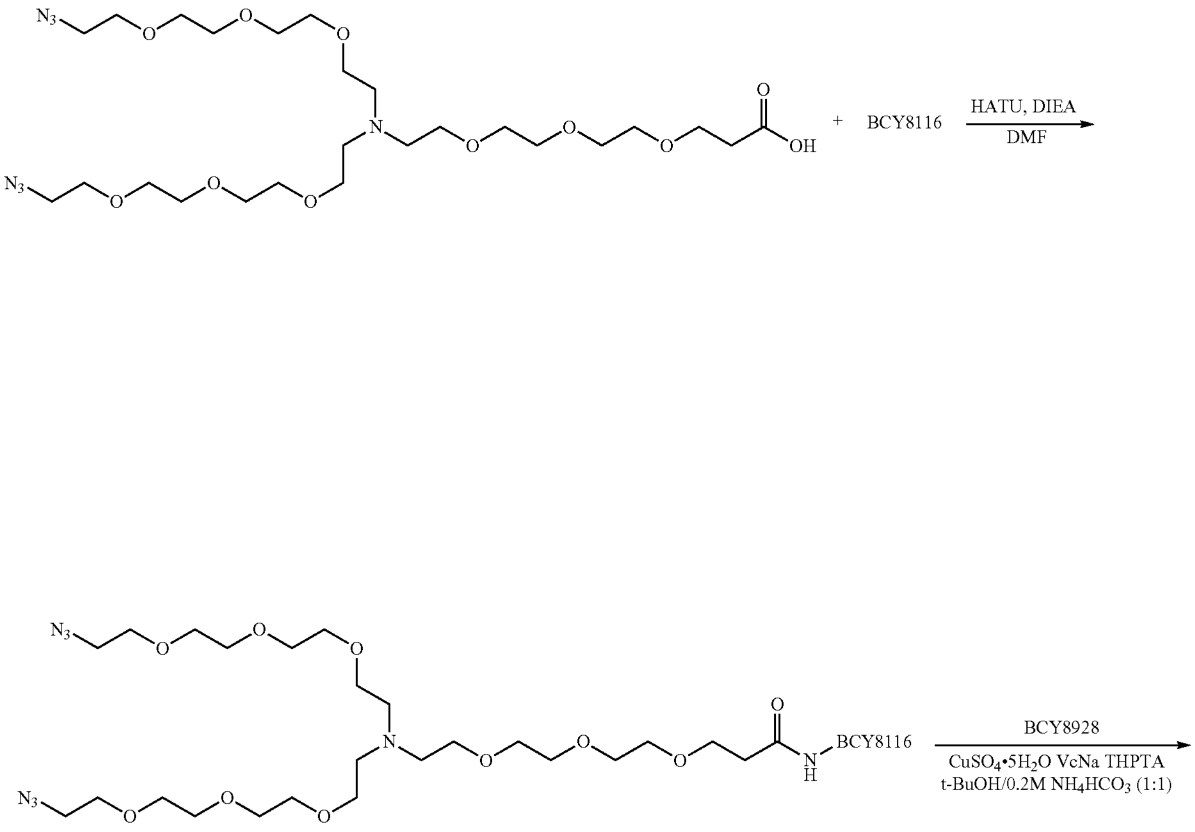

BCY12476

-continued
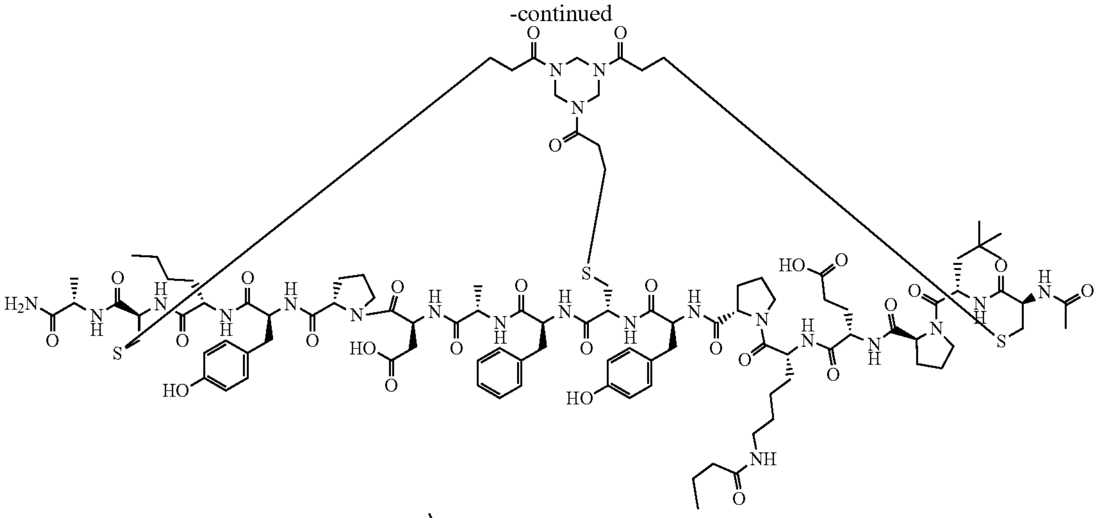
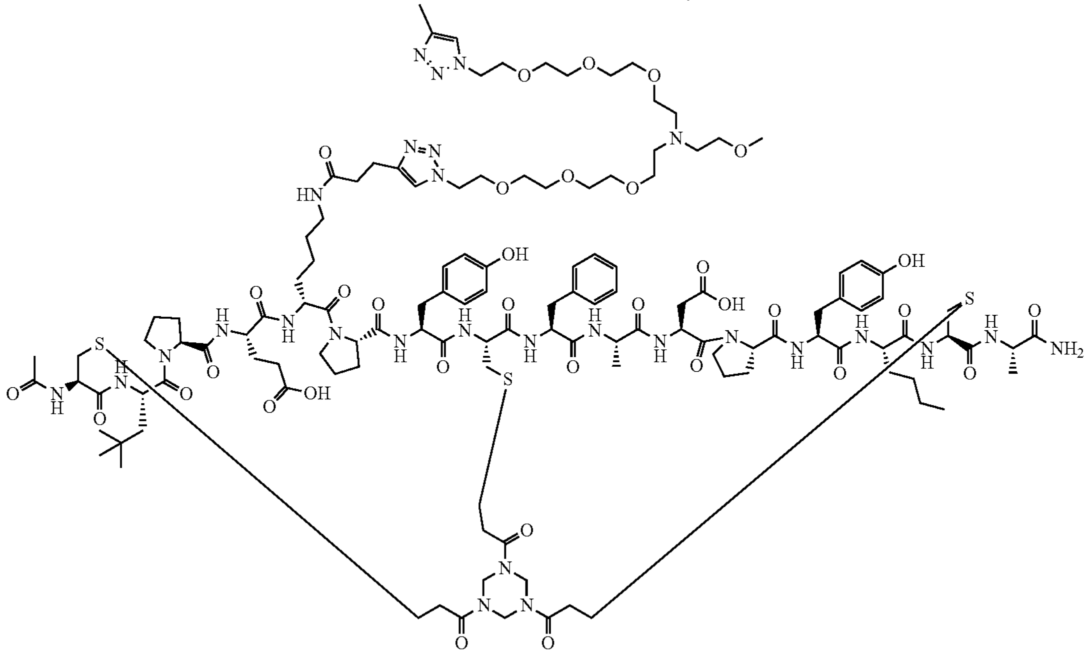
BCY00011863
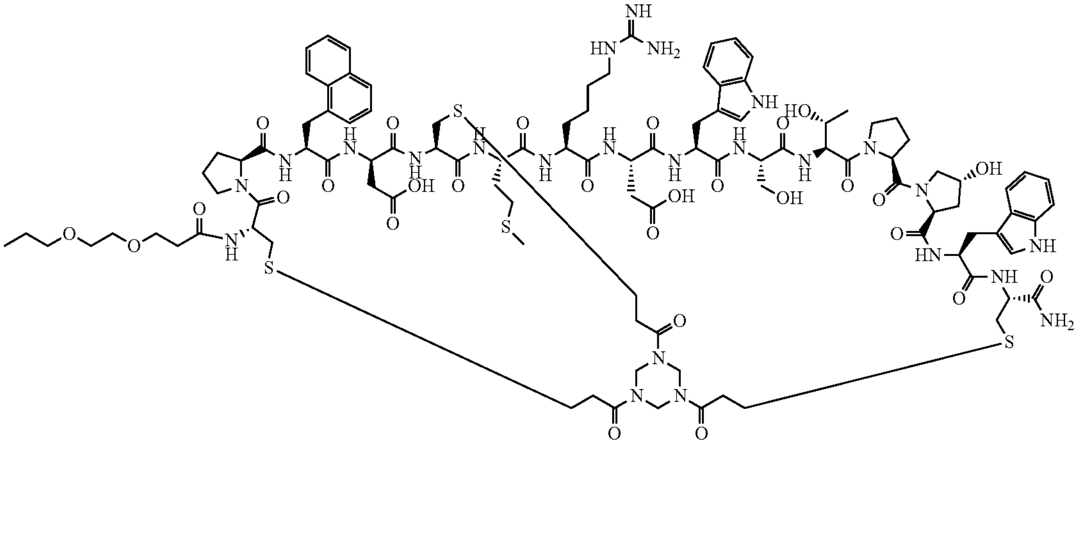 [SMILES: CCCOCCOCCC(=O)N[C@H]1CSCCC(=O)N2CN3CN(C2)C(=O)CCSC[C@H](NC(=O)[C@@H](CC(=O)O)NC(=O)[C@H](Cc2cccc4ccccc24)NC(=O)[C@@H]2CCCN2C1=O)C(=O)N[C@@H](CCSC)C(=O)N[C@@H](CCCCNC(=N)N)C(=O)N[C@@H](CC(=O)O)C(=O)N[C@@H](Cc1c[nH]c2ccccc12)C(=O)N[C@@H](CO)C(=O)N[C@@H]([C@@H](C)O)C(=O)N1CCC[C@H]1C(=O)N1C[C@H](O)C[C@H]1C(=O)N[C@@H](Cc1c[nH]c2ccccc12)C(=O)N[C@H](C(N)=O)CSCCC3=O]

wherein BCY8116 is a peptide ligand which comprises a polypeptide having amino acid sequence:

(SEQ ID NO: 1)
$C_i$P[1Nal][dD]$C_{ii}$M[HArg]DWSTP[HyP]W$C_{iii}$, wherein the three reactive cysteine groups ($C_i$, $C_{ii}$ and $C_{iii}$) are separated by two loop sequences, and wherein the peptide ligand further comprises a molecular scaffold which is 1,1',1"-(1,3,5-triazinane-1,3,5-triyl) triprop-2-en-1-one (TATA) and which forms covalent bonds with the reactive cysteine groups of the polypeptide such that two polypeptide loops are formed on the molecular scaffold; or a salt thereof;

wherein BCY8928 is a peptide ligand which comprises a polypeptide having amino acid sequence:

(SEQ ID NO: 2)
Ac-$C_i$[tBuAla]PE[D-Lys(PYA)]PY$C_{ii}$FADPY[Nle]$C_{iii}$-A, wherein the three reactive cysteine groups ($C_i$, $C_{ii}$ and $C_{iii}$) are separated by two loop sequences, and wherein the peptide ligand further comprises a molecular scaffold which is 1,1',1"-(1,3,5-triazinane-1,3,5-triyl) triprop-2-en-1-one (TATA) and which forms covalent bonds with the reactive cysteine groups of the polypeptide such that two polypeptide loops are formed on the molecular scaffold; or a salt thereof, wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

21. A compound, which is compound BCY12476:

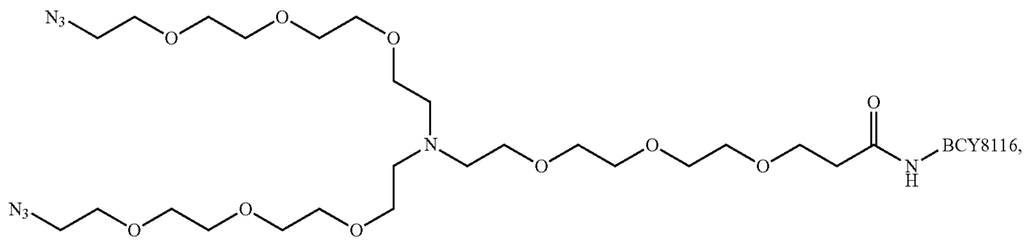

BCY12476 or a salt thereof, wherein BCY8116 is a peptide ligand which comprises a polypeptide having amino acid sequence:

(SEQ ID NO: 1)
$C_i$P[1Nal][dD]$C_{ii}$M[HArg]DWSTP[HyP]W$C_{iii}$, wherein the three reactive cysteine groups ($C_i$, $C_{ii}$ and $C_{iii}$) are separated by two loop sequences, and wherein the peptide ligand further comprises a molecular scaffold which is 1,1',1"-(1,3,5-triazinane-1,3,5-triyl) triprop-2-en-1-one (TATA) and which forms covalent bonds with the reactive cysteine groups of the polypeptide such that two polypeptide loops are formed on the molecular scaffold; or a salt thereof;

wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

* * * * *

SEQUENCE LISTING

```
Sequence total quantity: 8
SEQ ID NO: 1            moltype = AA  length = 15
FEATURE                 Location/Qualifiers
REGION                  1..15
                        note = Synthetic Peptide
SITE                    3
                        note = Xaa - Xaa is 1Nal
SITE                    7
                        note = Xaa - Xaa is HArg
SITE                    13
                        note = Xaa - Xaa is HyP
source                  1..15
                        mol_type = protein
                        organism = synthetic construct
SEQUENCE: 1
CPXDCMXDWS TPXWC                                                   15

SEQ ID NO: 2            moltype = AA  length = 16
FEATURE                 Location/Qualifiers
REGION                  1..16
                        note = Synthetic Peptide
SITE                    2
                        note = Xaa - Xaa is tBuAla
```

-continued

```
SITE                    5
                        note = Xaa - Xaa is D-Lys(PYA)
SITE                    14
                        note = Xaa - Xaa is Nle
source                  1..16
                        mol_type = protein
                        organism = synthetic construct
SEQUENCE: 2
CXPEXPYCFA DPYXCA                                                  16

SEQ ID NO: 3            moltype = AA  length = 16
FEATURE                 Location/Qualifiers
REGION                  1..16
                        note = Synthetic Peptide
SITE                    2
                        note = Xaa - Xaa is tBuAla
SITE                    5
                        note = Xaa - Xaa is D-Lys(PYA)
SITE                    14
                        note = Xaa - Xaa is Nle
source                  1..16
                        mol_type = protein
                        organism = synthetic construct
SEQUENCE: 3
CXPEXPYCFA DPYXCA                                                  16

SEQ ID NO: 4            moltype = AA  length = 16
FEATURE                 Location/Qualifiers
REGION                  1..16
                        note = Synthetic Peptide
SITE                    2
                        note = Xaa - Xaa is tBuAla
SITE                    5
                        note = Xaa - Xaa is D-Lys(PYA)
SITE                    14
                        note = Xaa - Xaa is Nle
source                  1..16
                        mol_type = protein
                        organism = synthetic construct
SEQUENCE: 4
CXPEXPYCFA DPYXCK                                                  16

SEQ ID NO: 5            moltype = AA  length = 15
FEATURE                 Location/Qualifiers
REGION                  1..15
                        note = Synthetic Peptide
SITE                    3
                        note = Xaa - Xaa is 1Nal
SITE                    7
                        note = Xaa - Xaa is HArg
SITE                    13
                        note = Xaa - Xaa is HyP
source                  1..15
                        mol_type = protein
                        organism = synthetic construct
SEQUENCE: 5
CPXDCMXDWS TPXWC                                                   15

SEQ ID NO: 6            moltype = AA  length = 16
FEATURE                 Location/Qualifiers
REGION                  1..16
                        note = Synthetic Peptide
SITE                    2
                        note = Xaa - Xaa is tBuAla
SITE                    5
                        note = Xaa - Xaa is D-Lys(PYA)
SITE                    14
                        note = Xaa - Xaa is Nle
source                  1..16
                        mol_type = protein
                        organism = synthetic construct
SEQUENCE: 6
CXPEXPYCFA DPYXCA                                                  16

SEQ ID NO: 7            moltype = AA  length = 16
FEATURE                 Location/Qualifiers
REGION                  1..16
                        note = Synthetic Peptide
SITE                    2
```

-continued

| | |
|---|---|
| | note = Xaa - Xaa is tBuAla |
| SITE | 5 |
| | note = Xaa - Xaa is D-Lys(PYA) |
| SITE | 14 |
| | note = Xaa - Xaa is Nle |
| source | 1..16 |
| | mol_type = protein |
| | organism = synthetic construct |
| SEQUENCE: 7 | |
| CXPEXPYCFA DPYXCA | 16 |
| | |
| SEQ ID NO: 8 | moltype = AA length = 16 |
| FEATURE | Location/Qualifiers |
| REGION | 1..16 |
| | note = Synthetic Peptide |
| SITE | 2 |
| | note = Xaa - Xaa is tBuAla |
| SITE | 5 |
| | note = Xaa - Xaa is D-Lys(PYA) |
| SITE | 14 |
| | note = Xaa - Xaa is Nle |
| source | 1..16 |
| | mol_type = protein |
| | organism = synthetic construct |
| SEQUENCE: 8 | |
| CXPEXPYCFA DPYXCK | 16 |